(12) United States Patent
Ribich et al.

(10) Patent No.: US 11,786,533 B2
(45) Date of Patent: Oct. 17, 2023

(54) USE OF EZH2 INHIBITORS FOR TREATING CANCER

(71) Applicant: Epizyme, Inc., Cambridge, MA (US)

(72) Inventors: Scott Ribich, Lexington, MA (US); Michael Thomenius, Rockland, MA (US)

(73) Assignee: Epizyme, Inc., Cambridge, MA (US)

( * ) Notice: Subject to any disclaimer, the term of this patent is extended or adjusted under 35 U.S.C. 154(b) by 587 days.

(21) Appl. No.: 16/306,182

(22) PCT Filed: Jun. 1, 2017

(86) PCT No.: PCT/US2017/035391
§ 371 (c)(1),
(2) Date: Nov. 30, 2018

(87) PCT Pub. No.: WO2017/210395
PCT Pub. Date: Dec. 7, 2017

(65) Prior Publication Data
US 2022/0288085 A1    Sep. 15, 2022

Related U.S. Application Data

(60) Provisional application No. 62/344,338, filed on Jun. 1, 2016.

(51) Int. Cl.
*A61K 31/5377* (2006.01)
*A61K 35/04* (2006.01)
*A61P 35/04* (2006.01)
*A61K 9/00* (2006.01)

(52) U.S. Cl.
CPC ........ *A61K 31/5377* (2013.01); *A61K 9/0019* (2013.01); *A61K 9/0053* (2013.01); *A61P 35/04* (2018.01)

(58) Field of Classification Search
CPC ........................... A61K 31/5377; A61P 35/04
USPC ...................................................... 514/228.8
See application file for complete search history.

(56) References Cited

U.S. PATENT DOCUMENTS

| 8,410,088 B2 * | 4/2013 | Kuntz | A61K 31/5377 |
| | | | 544/131 |
| 9,175,331 B2 * | 11/2015 | Kuntz | C12Q 1/48 |
| 9,394,283 B2 * | 7/2016 | Kuntz | A61K 31/5377 |
| 2012/0071418 A1 | 3/2012 | Copeland et al. | |
| 2013/0303555 A1 | 11/2013 | Copeland et al. | |
| 2013/0309250 A1 | 11/2013 | Cogswell et al. | |
| 2015/0051163 A1 * | 2/2015 | Keilhack | C07D 405/12 |
| | | | 514/171 |
| 2015/0065503 A1 | 3/2015 | Kuntz et al. | |
| 2015/0283142 A1 * | 10/2015 | Stern | C07D 401/12 |
| | | | 424/1.49 |
| 2015/0313906 A1 * | 11/2015 | Creasy | A61K 31/4355 |
| | | | 514/253.09 |
| 2015/0320754 A1 | 11/2015 | Kutok et al. | |
| 2016/0176882 A1 | 6/2016 | Chan et al. | |
| 2020/0163945 A1 | 5/2020 | Daigle et al. | |

FOREIGN PATENT DOCUMENTS

| WO | WO 2012/034132 A2 | 3/2012 |
| WO | WO 2012/118812 A2 | 9/2012 |
| WO | WO 2012/142504 A1 | 10/2012 |
| WO | WO 2012/142513 A1 | 10/2012 |
| WO | WO 2013/138361 A1 | 9/2013 |
| WO | 2013155464 | * 10/2013 |
| WO | WO 2013/155317 A1 | 10/2013 |
| WO | WO 2013/155464 A1 | 10/2013 |
| WO | 2014062720 | * 4/2014 |
| WO | WO 2014/062720 A2 | 4/2014 |
| WO | WO 2014/062732 A1 | 4/2014 |
| WO | WO 2014/062733 A2 | 4/2014 |
| WO | WO 2014/100646 A1 | 6/2014 |
| WO | WO 2014/100665 A1 | 6/2014 |
| WO | WO 2014/144747 A1 | 9/2014 |
| WO | WO 2014/165422 A1 | 10/2014 |
| WO | WO 2014/172044 A1 | 10/2014 |
| WO | WO 2015/010049 A1 | 1/2015 |
| WO | WO 2015/010078 A2 | 1/2015 |
| WO | WO 2015/057859 A1 | 4/2015 |
| WO | WO 2015/058125 A1 | 4/2015 |
| WO | WO 2015/085325 A1 | 6/2015 |
| WO | 2015195848 | * 12/2015 |
| WO | WO 2015/195848 A1 | 12/2015 |
| WO | WO 2015/200650 A9 | 12/2015 |
| WO | WO 2016/061507 A1 | 4/2016 |
| WO | WO 2016/081523 A1 | 5/2016 |

(Continued)

OTHER PUBLICATIONS

Garapaty-Rao, S. et al. (Nov. 2013) "Identification of EZH2 and EZH1 Small Molecule Inhibitors with Selective Impact on Diffuse Large B Cell Lymphoma Cell Growth" Chem Biol, 20:1329-1339.
Italiano, A. et al. (2018) "Tazemetostat, an EZH2 inhibitor, in relapsed or refractory B-cell non-Hodgkin lymphoma and advanced solid tumours: a first-in-human, open-label, phase 1 study" Lancet Oncology, 19(5):649-659.
Knutson, S.K. et al. (2012) "A Selective Inhibitor of EZH2 Blocks H3K27 Methylation and Kills Mutant Lymphoma Cells" Nat Chem Biol, 8:890-896.
Mahmoud, F. et al. (Apr. 22, 2016) "Role of EZH2 histone methyltransferase in melanoma progression and metastasis" Cancer Biol Ther, 17(6):579-591.

(Continued)

*Primary Examiner* — Niloofar Rahman
(74) *Attorney, Agent, or Firm* — Dechert LLP; Andrea L. C. Reid; Peter Diez

(57) ABSTRACT

The disclosure provides a method for treating cancer in a subject in need thereof comprising administering to the subject: (a) a therapeutically effective amount of an EZH2 inhibitor and (b) a therapeutically effective amount of an immune checkpoint inhibitor. In certain embodiments of the methods of the disclosure, the EZH2 inhibitor is tazemetostat.

15 Claims, No Drawings

(56) References Cited

FOREIGN PATENT DOCUMENTS

| WO | WO 2016/172199 A1 | 10/2016 |
| WO | WO 2016/201328 A1 | 12/2016 |
| WO | WO 2017/023671 A1 | 2/2017 |
| WO | WO 2017/035234 A1 | 3/2017 |
| WO | WO 2017/053930 A2 | 3/2017 |
| WO | WO 2017/062495 A2 | 4/2017 |
| WO | WO 2017/079757 A1 | 5/2017 |
| WO | WO 2017/100362 A2 | 6/2017 |
| WO | WO 2017/132518 A1 | 8/2017 |
| WO | WO 2017/139404 A1 | 8/2017 |
| WO | WO 2017/210395 A1 | 12/2017 |
| WO | WO-2017218953 A1 | 12/2017 |
| WO | WO-2018102687 A2 | 6/2018 |
| WO | WO-2018144798 A1 | 8/2018 |
| WO | WO-2018183885 A1 | 10/2018 |
| WO | WO-2018223030 A1 | 12/2018 |

OTHER PUBLICATIONS

Peng et al. (Oct. 26, 2015) "Epigenetic silencing of $T_H1$-type chemokines shapes tumour immunity and immunotherapy" Nature, 527:249-253.

Prokopuk, L. et al. (2018) "Pharmacological inhibition of EZH2 disrupts the female germline epigenome" Clin Epigenetics, 10:33, https://doi.org/10.1186/s13148-018-0465-4; 12 pages.

Qi, W. et al. (2012) "Selective inhibition of Ezh2 by a small molecule inhibitor blocks tumor cells proliferation" Proc Natl Acad Sci USA, 109(52):21360-21365.

Terranova-Barberio, M. et al. (May 2016) "Epigenetic modifiers in immunotherapy: a focus on checkpoint inhibitors" Immunotherapy, 8(6):705-719.

Varambally, S. et al. (2002) "The Poly comb Group Protein EZH2 is Involved in Progression of Prostate Cancer" Nature, 419:624-629.

Zou, W. et al. (Mar. 2, 2016) "PD-L1 (B7-H1) andPD-1 pathway blockade for cancer therapy: Mechanisms, response biomarkers, and combinations" Sci Transl Med, 8:1-14.

\* cited by examiner

USE OF EZH2 INHIBITORS FOR TREATING CANCER

RELATED APPLICATIONS

This application is a U.S. National Phase application, filed under 35 U.S.C. § 371, of International Application No. PCT/US2017/035391, filed on Jun. 1, 2017, which claims priority to, and the benefit of, U.S. Provisional Application No. 62/344,338, filed on Jun. 1, 2016, the entire contents of each of which are incorporated herein by reference in their entireties.

SUMMARY

The present disclosure provides strategies, treatment modalities, methods, combinations, and compositions for the treatment of diseases, e.g., proliferative diseases. Some aspects of the present disclosure are based on the recognition that combining treatment modalities or strategies employing an epigenetic modulator, e.g., an EZH2 inhibitor, with those employing an immune checkpoint inhibitor results in an advantageous combination therapy approach for treating certain diseases, e.g., certain proliferative diseases. The strategies, treatment modalities, methods, combinations, and compositions provided herein are useful for modulating epigenetic modifications in a target cell or tissue, e.g., a cancer cell or a tumor in a subject, and for improving the immune system response of a subject to the target cell or tissue.

Some aspects of the disclosure provide methods for treating cancer in a subject in need thereof comprising administering to the subject: (a) a therapeutically effective amount of an EZH2 inhibitor and (b) a therapeutically effective amount of an immune checkpoint inhibitor.

Some aspects of the present disclosure provide methods comprising administering an EZH2 inhibitor to a subject who is already receiving an immune checkpoint inhibitor, e.g., as part of an ongoing treatment strategy for a proliferative disease that the subject has been diagnosed with. In some embodiments, the EZH2 inhibitor is administered to the subject already receiving the immune checkpoint inhibitor based on the recognition that the proliferative disease in the subject is sensitive to treatment with the EZH2 inhibitor, or to a combination of the EZH2 inhibitor and the immune checkpoint inhibitor.

Some aspects of the present disclosure provide methods comprising administering an immune checkpoint inhibitor to a subject who is already receiving an EZH2 inhibitor, e.g., as part of an ongoing treatment strategy for a proliferative disease that the subject has been diagnosed with. In some embodiments, the immune checkpoint inhibitor is administered to the subject already receiving the EZH2 inhibitor based on the recognition that the proliferative disease in the subject is sensitive to treatment with the immune checkpoint inhibitor, or to a combination of the EZH2 inhibitor and the immune checkpoint inhibitor.

Some aspects of this disclosure provide methods of administering (a) a therapeutically effective amount of an EZH2 inhibitor and (b) a therapeutically effective amount of an immune checkpoint inhibitor to a subject in need thereof, e.g., to a subject having or diagnosed with a proliferative disease, based on the recognition that the disease in the subject is sensitive to combined treatment with the EZH2 inhibitor and the immune checkpoint inhibitor. In some embodiments, the disease in the subject is not sensitive to treatment with the EZH2 inhibitor and/or the immune checkpoint inhibitor alone.

Some aspects of this disclosure provide methods for treating a disease in a subject, e.g., a proliferative disease, by administering (a) an EZH2 inhibitor and (b) an immune checkpoint inhibitor to the subject, wherein the disease cannot effectively be treated or a clinically desirable endpoint cannot be reached by administering the EZH2 inhibitor alone or by administering the immune checkpoint inhibitor alone. In some embodiments, the method comprises administering an EZH2 inhibitor and/or an immune checkpoint inhibitor to the subject at a dosage that is lower than the minimal effective dose for administering the EZH2 inhibitor alone or the minimal effective dose for administering the immune checkpoint inhibitor alone. In some embodiments, administering both inhibitors at such sub-minimal dosages is useful to avoid side effects associated with administering the agents at higher dosages, while still achieving a clinical desirable outcome.

Some aspects of the disclosure provide combinations and compositions comprising (a) a therapeutically effective amount of an EZH2 inhibitor and (b) a therapeutically effective amount of an immune checkpoint inhibitor.

In some embodiments, EZH2 inhibitors of the disclosure comprise a compound of Formula (Ig) or a pharmaceutically acceptable salt thereof:

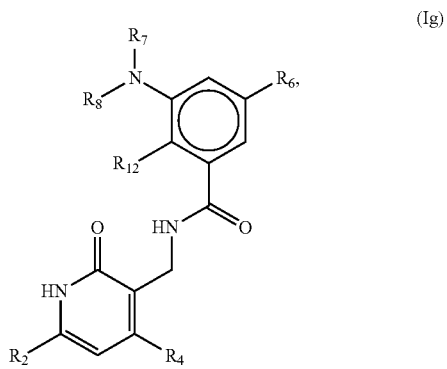

(Ig)

wherein $R_2$, $R_4$ and $R_{12}$ are each, independently $C_{1-6}$ alkyl; $R_6$ is $C_6$-$C_{10}$ aryl or 5- or 6-membered heteroaryl, each of which is optionally substituted with one or more -$Q_2$-$T_2$, wherein $Q_2$ is a bond or $C_1$-$C_3$ alkyl linker optionally substituted with halo, cyano, hydroxyl or $C_1$-$C_6$ alkoxy, and $T_2$ is H, halo, cyano, —$OR_a$, —$NR_aR_b$, —$(NR_aR_bR_c)^+A^-$, —$C(O)R_a$, —$C(O)OR_a$, —$C(O)NR_aR_b$, —$NR_bC(O)R_a$, —$NR_bC(O)OR_a$, —$S(O)_2R_a$, —$S(O)_2NR_aR_b$, or $R_{S2}$, in which each of $R_a$, $R_b$, and $R_c$, independently is H or $R_{S3}$, $A^-$ is a pharmaceutically acceptable anion, each of $R_{S2}$ and $R_{S3}$, independently, is $C_1$-$C_6$ alkyl, $C_3$-$C_8$ cycloalkyl, $C_6$-$C_{10}$ aryl, 4 to 12-membered heterocycloalkyl, or 5- or 6-membered heteroaryl, or $R_a$ and $R_b$, together with the N atom to which they are attached, form a 4 to 12-membered heterocycloalkyl ring having 0 or 1 additional heteroatom, and each of $R_{S2}$, $R_{S3}$, and the 4 to 12-membered heterocycloalkyl ring formed by $R_a$ and $R_b$, is optionally substituted with one or more -$Q_3$-$T_3$, wherein $Q_3$ is a bond or $C_1$-$C_3$ alkyl linker each optionally substituted with halo, cyano, hydroxyl or $C_1$-$C_6$ alkoxy, and $T_3$ is selected from the group consisting of halo, cyano, $C_1$-$C_6$ alkyl, $C_3$-$C_8$ cycloalkyl, $C_6$-$C_{10}$ aryl, 4 to 12-membered heterocycloalkyl, 5- or 6-membered heteroaryl, $OR_d$, $COOR_d$, —$S(O)_2R_d$, —$NR_dR_e$, and —$C(O)NR_dR_e$, each of $R_d$ and $R_e$ independently being H or $C_1$-$C_6$ alkyl, or -$Q_3$-$T_3$ is oxo; or any two neighboring -$Q_2$-$T_2$, together with the atoms to which they are attached form a 5- or 6-membered ring optionally containing 1-4 heteroatoms selected from N, O and S and optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl;

$R_7$ is -$Q_4$-$T_4$, in which $Q_4$ is a bond, $C_1$-$C_4$ alkyl linker, or $C_2$-$C_4$ alkenyl linker, each linker optionally substituted with halo, cyano, hydroxyl or $C_1$-$C_6$ alkoxy, and $T_4$ is H, halo, cyano, $NR_fR_g$, —$OR_f$, —$C(O)R_f$, —$C(O)OR_f$, —$C(O)NR_fR_g$, —$C(O)NR_fOR_g$, —$NR_fC(O)R_g$, —$S(O)_2R_f$, or $R_{S4}$, in which each of $R_f$ and $R_g$, independently is H or $R_{S5}$, each of $R_{S4}$ and $R_{S5}$, independently is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 12-membered heterocycloalkyl, or 5- or 6-membered heteroaryl, and each of $R_{S4}$ and $R_{S5}$ is optionally substituted with one or more -$Q_5$-$T_5$, wherein $Q_5$ is a bond, C(O), C(O)$NR_k$, $NR_k$C(O), S(O)$_2$, or $C_1$-$C_3$ alkyl linker, $R_k$ being H or $C_1$-$C_6$ alkyl, and $T_5$ is H, halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, 5- or 6-membered heteroaryl, or $S(O)_qR_q$ in which q is 0, 1, or 2 and $R_q$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 12-membered heterocycloalkyl, or 5- or 6-membered heteroaryl, and $T_5$ is optionally substituted with one or more substituents selected from the group consisting of halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl except when $T_5$ is H, halo, hydroxyl, or cyano; or -$Q_5$-$T_5$ is oxo; and $R_8$ is H, halo, hydroxyl, COOH, cyano, $R_{S6}$, $OR_{S6}$, or $COOR_{S6}$, in which $R_{S6}$ is $C_1$-$C_6$ alkyl, $C_2$-$C_6$ alkenyl, $C_2$-$C_6$ alkynyl, $C_3$-$C_8$ cycloalkyl, 4 to 12-membered heterocycloalkyl, amino, mono-$C_1$-$C_6$ alkylamino, or di-$C_1$-$C_6$ alkylamino, and $R_{S6}$ is optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, and di-$C_1$-$C_6$ alkylamino; or $R_7$ and $R_8$, together with the N atom to which they are attached, form a 4 to 11-membered heterocycloalkyl ring having 0 to 2 additional heteroatoms, and the 4 to 11-membered heterocycloalkyl ring formed by $R_7$ and $R_8$ is optionally substituted with one or more -$Q_6$-$T_6$, wherein $Q_6$ is a bond, C(O), C(O)$NR_m$, $NR_m$C(O), S(O)$_2$, or $C_1$-$C_3$ alkyl linker, $R_m$ being H or $C_1$-$C_6$ alkyl, and $T_6$ is H, halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, 5- or 6-membered heteroaryl, or $S(O)_pR_p$ in which p is 0, 1, or 2 and $R_p$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 12-membered heterocycloalkyl, or 5- or 6-membered heteroaryl, and $T_6$ is optionally substituted with one or more substituents selected from the group consisting of halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl except when $T_6$ is H, halo, hydroxyl, or cyano; or -$Q_6$-$T_6$ is oxo.

In certain embodiments of Formula (Ig), $R_6$ is $C_6$-$C_{10}$ aryl or 5- or 6-membered heteroaryl, each of which is optionally, independently substituted with one or more -$Q_2$-$T_2$, wherein $Q_2$ is a bond or $C_1$-$C_3$ alkyl linker, and $T_2$ is H, halo, cyano, —$OR_a$, —$NR_aR_b$, —$(NR_aR_bR_c)^+A^-$, —$C(O)NR_aR_b$, —$NR_bC(O)R_a$, —$S(O)_2R_a$, or $R_{S2}$, in which each of $R_a$ and $R_b$, independently is H or $R_{S3}$, each of $R_{S2}$ and $R_{S3}$, independently, is $C_1$-$C_6$ alkyl, or $R_a$ and $R_b$, together with the N atom to which they are attached, form a 4 to 7-membered heterocycloalkyl ring having 0 or 1 additional heteroatom, and each of $R_{S2}$, $R_{S3}$, and the 4 to 7-membered heterocycloalkyl ring formed by $R_a$ and $R_b$, is optionally, independently substituted with one or more -$Q_3$-$T_3$, wherein $Q_3$ is a bond or $C_1$-$C_3$ alkyl linker and $T_3$ is selected from the group consisting of halo, $C_1$-$C_6$ alkyl, 4 to 7-membered heterocycloalkyl, $OR_d$, —$S(O)_2R_d$, and —$NR_dR_e$, each of $R_d$ and $R_e$ independently being H or $C_1$-$C_6$ alkyl, or -$Q_3$-$T_3$ is oxo; or any two neighboring -$Q_2$-$T_2$, together with the atoms to which they are attached form a 5- or 6-membered ring optionally containing 1-4 heteroatoms selected from N, O and S.

In some embodiments, EZH2 inhibitors of the disclosure comprise a compound of Formula (II) or a pharmaceutically acceptable salt thereof:

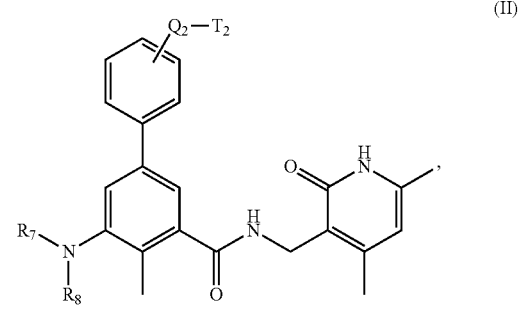

(II)

wherein $Q_2$ is a bond or methyl linker, $T_2$ is H, halo, —$OR_a$, —$NR_aR_b$, —$(NR_aR_bR_c)^+A^-$, or —$S(O)_2NR_aR_b$, $R_7$ is piperidinyl, tetrahydropyran, cyclopentyl, or cyclohexyl, each optionally substituted with one -$Q_5$-$T_5$ and $R_8$ is ethyl.

In some embodiments, EZH2 inhibitors of the disclosure comprise a compound of Formula (IIa) or a pharmaceutically acceptable salt thereof:

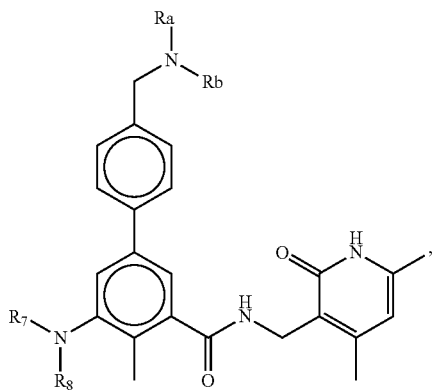

(IIa)

wherein
each of $R_a$ and $R_b$, independently is H or $R_{S3}$, $R_{S3}$ being $C_1$-$C_6$ alkyl, $C_3$-$C_8$ cycloalkyl, $C_6$-$C_{10}$ aryl, 4 to 12-membered heterocycloalkyl, or 5- or 6-membered heteroaryl, or $R_a$ and $R_b$, together with the N atom to which they are attached, form a 4 to 12-membered heterocycloalkyl ring having 0 or 1 additional heteroatom, and each of $R_{S3}$ and the 4 to 12-membered heterocycloalkyl ring formed by $R_a$ and $R_b$, is optionally substituted with one or more -$Q_3$-$T_3$, wherein $Q_3$ is a bond or $C_1$-$C_3$ alkyl linker each optionally substituted with halo, cyano, hydroxyl or $C_1$-$C_6$ alkoxy, and $T_3$ is selected from the group consisting of halo, cyano, $C_1$-$C_6$ alkyl, $C_3$-$C_8$ cycloalkyl, $C_6$-$C_{10}$ aryl, 4 to 12-membered heterocycloalkyl, 5- or 6-membered heteroaryl, $OR_d$, $COOR_d$, —$S(O)_2R_d$, —$NR_dR_e$, and —$C(O)NR_dR_e$, each of $R_d$ and $R_e$ independently being H or $C_1$-$C_6$ alkyl, or -$Q_3$-$T_3$ is oxo;

$R_7$ is -$Q_4$-$T_4$, in which $Q_4$ is a bond, $C_1$-$C_4$ alkyl linker, or $C_2$-$C_4$ alkenyl linker, each linker optionally substituted with halo, cyano, hydroxyl or $C_1$-$C_6$ alkoxy, and $T_4$ is H, halo, cyano, $NR_fR_g$, —$OR_f$, —$C(O)R_f$, —$C(O)OR_f$, —$C(O)NR_fR_g$, —$C(O)NR_fOR_g$, —$NR_fC(O)R_g$, —$S(O)_2R_f$, or $R_{S4}$, in which each of $R_f$ and $R_g$, independently is H or $R_{S5}$, each of $R_{S4}$ and $R_{S5}$, independently is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 7-membered heterocycloalkyl, or 5- or 6-membered heteroaryl, and each of $R_{S4}$ and $R_{S5}$ is optionally substituted with one or more -$Q_5$-$T_5$, wherein $Q_5$ is a bond, C(O), C(O)$NR_k$, $NR_k$C(O), S(O)$_2$, or $C_1$-$C_3$ alkyl linker, $R_k$ being H or $C_1$-$C_6$ alkyl, and $T_5$ is H, halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 7-membered heterocycloalkyl, 5- or 6-membered heteroaryl, or S(O)$_qR_q$ in which q is 0, 1, or 2 and $R_q$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 7-membered heterocycloalkyl, or 5- or 6-membered heteroaryl, and $T_5$ is optionally substituted with one or more substituents selected from the group consisting of halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 7-membered heterocycloalkyl, and 5- or 6-membered heteroaryl except when $T_5$ is H, halo, hydroxyl, or cyano; or -$Q_5$-$T_5$ is oxo; provided that $R_7$ is not H; and $R_8$ is H, halo, hydroxyl, COOH, cyano, $R_{S6}$, $OR_{S6}$, or $COOR_{S6}$, in which $R_{S6}$ is $C_1$-$C_6$ alkyl, $C_2$-$C_6$ alkenyl, $C_2$-$C_6$ alkynyl, amino, mono-$C_1$-$C_6$ alkylamino, or di-$C_1$-$C_6$ alkylamino, and $R_{S6}$ is optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, and di-$C_1$-$C_6$ alkylamino; or $R_7$ and $R_8$, together with the N atom to which they are attached, form a 4 to 11-membered heterocycloalkyl ring which has 0 to 2 additional heteroatoms and is optionally substituted with one or more -$Q_6$-$T_6$, wherein $Q_6$ is a bond, C(O), C(O)$NR_m$, $NR_m$C(O), S(O)$_2$, or $C_1$-$C_3$ alkyl linker, $R_m$ being H or $C_1$-$C_6$ alkyl, and $T_6$ is H, halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 7-membered heterocycloalkyl, 5- or 6-membered heteroaryl, or S(O)$_pR_p$ in which p is 0, 1, or 2 and $R_p$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 7-membered heterocycloalkyl, or 5- or 6-membered heteroaryl, and $T_6$ is optionally substituted with one or more substituents selected from the group consisting of halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 7-membered heterocycloalkyl, and 5- or 6-membered heteroaryl except when $T_6$ is H, halo, hydroxyl, or cyano; or -$Q_6$-$T_6$ is oxo.

In certain embodiments of Formula (IIa), $R_a$ and $R_b$, together with the N atom to which they are attached, form a 4 to 7-membered heterocycloalkyl ring having 0 or 1 additional heteroatoms to the N atom and the ring is optionally substituted with one or more -$Q_3$-$T_3$, wherein the heterocycloalkyl is azetidinyl, pyrrolidinyl, imidazolidinyl, pyrazolidinyl, oxazolidinyl, isoxazolidinyl, triazolidinyl, piperidinyl, 1,2,3,6-tetrahydropyridinyl, piperazinyl, or morpholinyl.

In certain embodiments of Formula (IIa), $R_7$ is $C_3$-$C_8$ cycloalkyl or 4 to 7-membered heterocycloalkyl, each optionally substituted with one or more -$Q_5$-$T_5$.

In certain embodiments of Formula (IIa), $R_7$ is piperidinyl, tetrahydropyran, tetrahydro-2H-thiopyranyl, cyclopentyl, cyclohexyl, pyrrolidinyl, or cycloheptyl, each optionally substituted with one or more -$Q_5$-$T_5$.

In certain embodiments of Formula (IIa), $R_8$ is H or $C_1$-$C_6$ alkyl which is optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, and di-$C_1$-$C_6$ alkylamino.

In some embodiments, EZH2 inhibitors of the disclosure comprise a compound is selected from

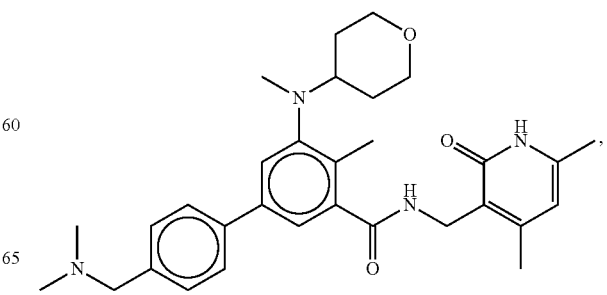

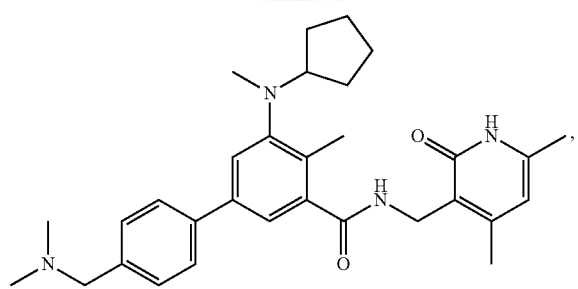
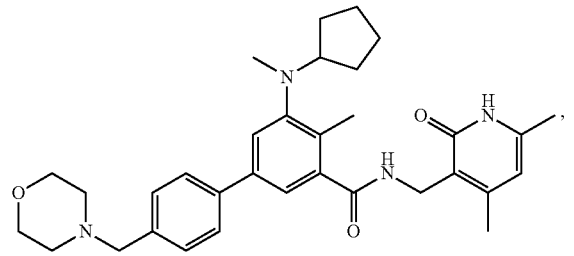
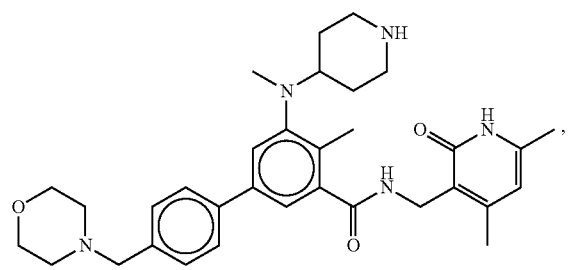
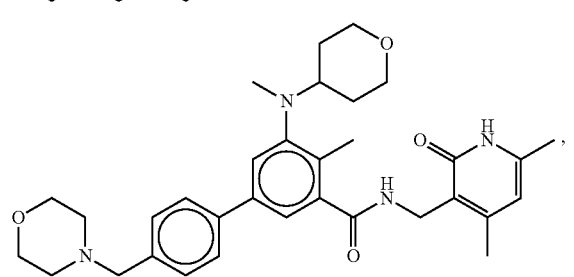
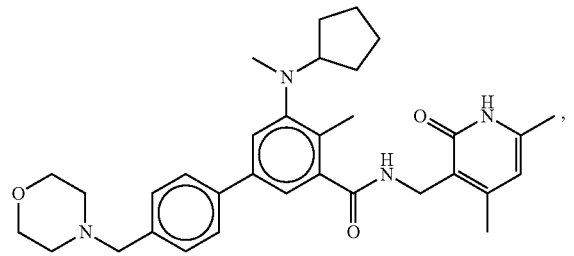
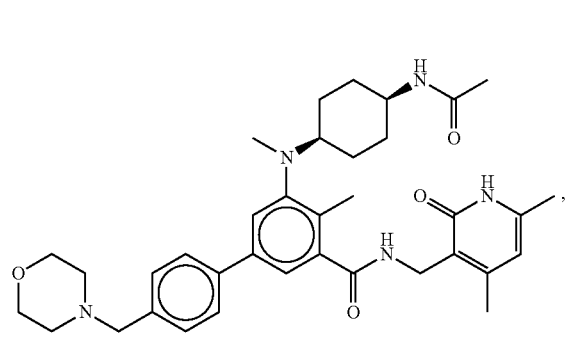
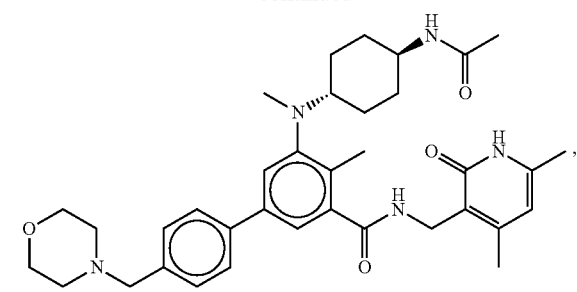
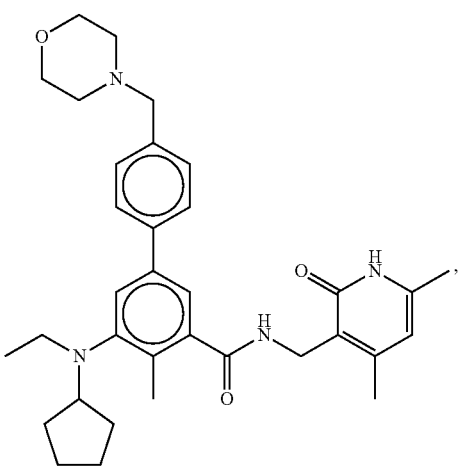
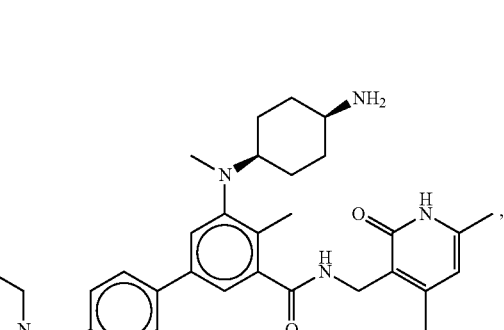
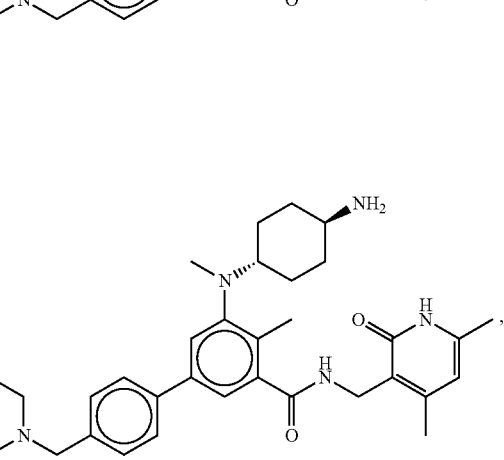

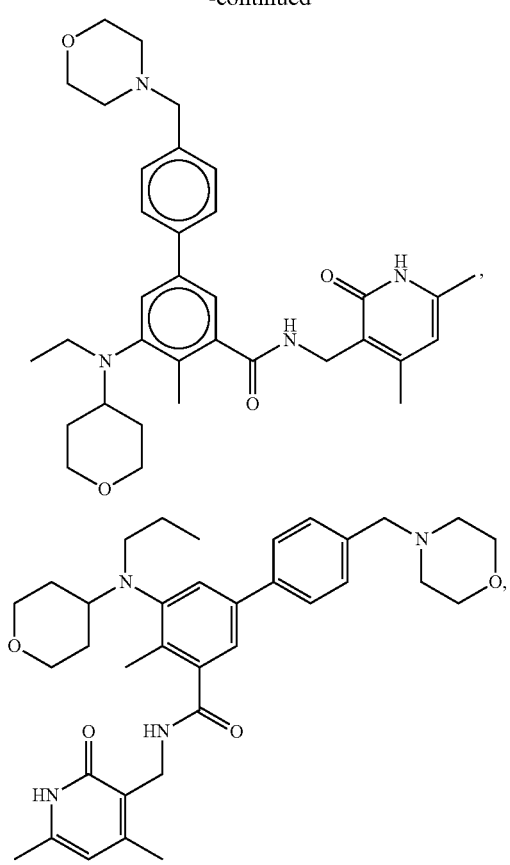
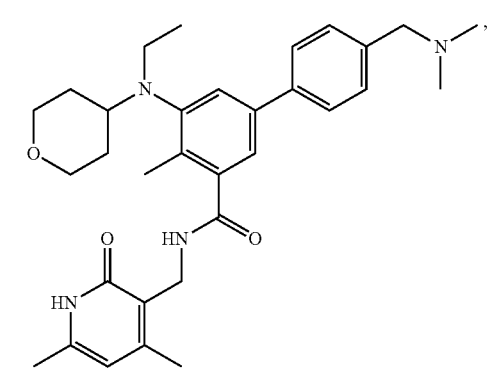
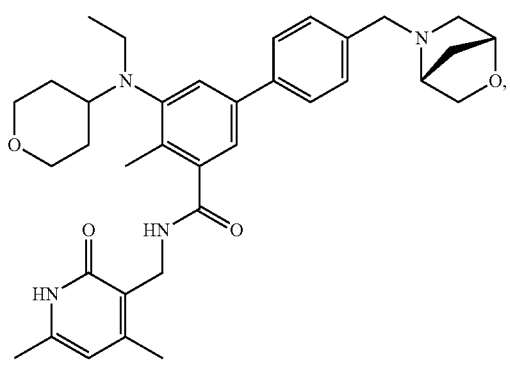
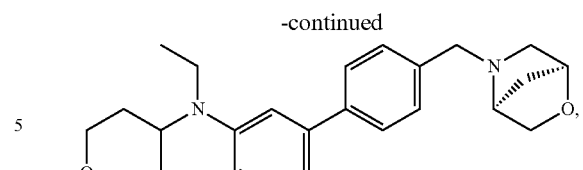
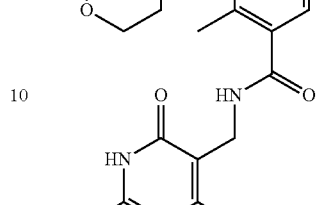
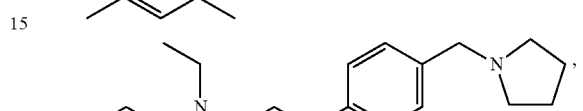
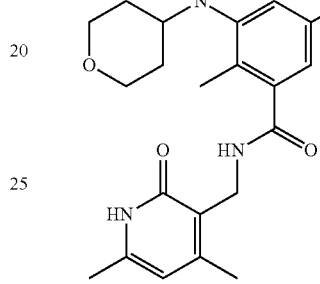
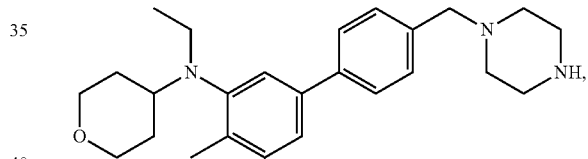
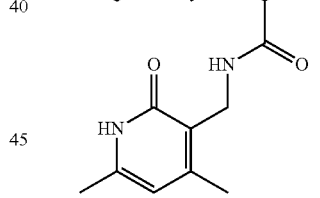
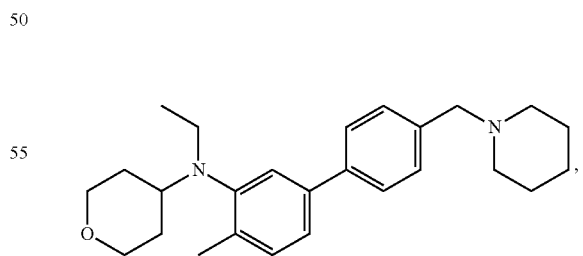
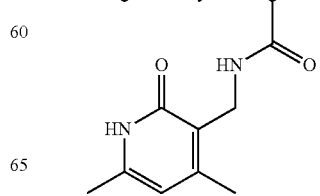

11
-continued
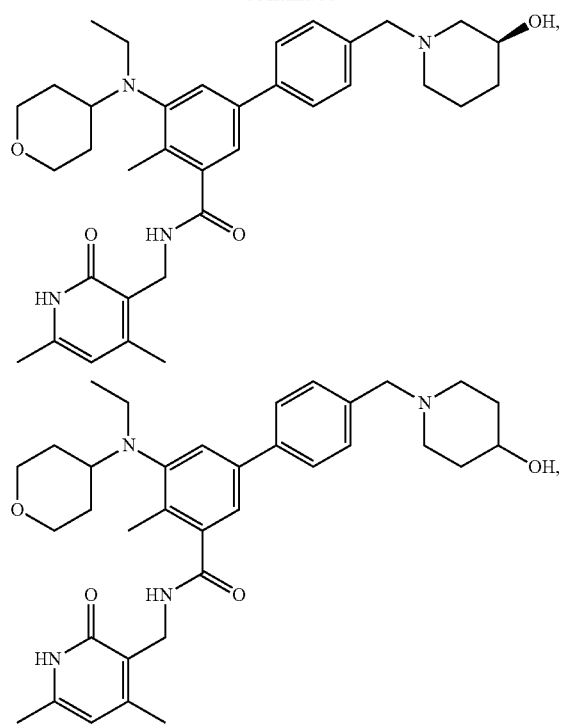
12
-continued
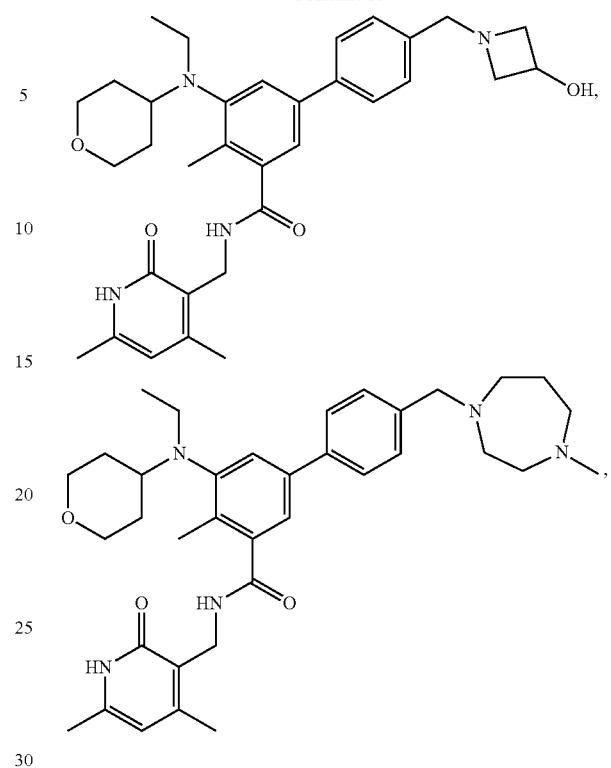
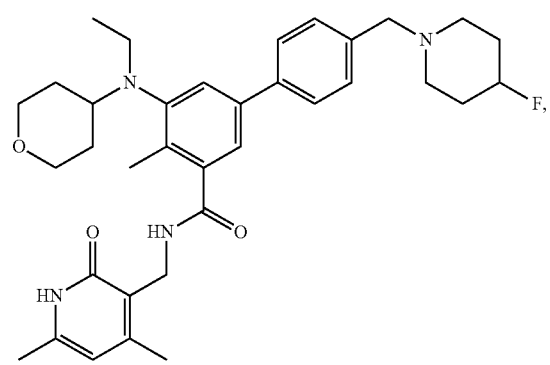
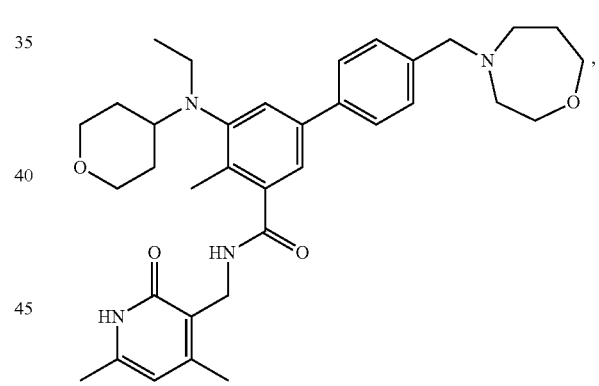
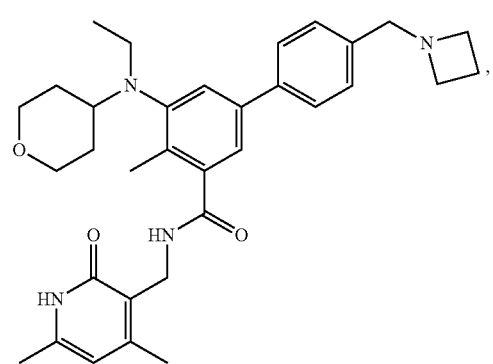
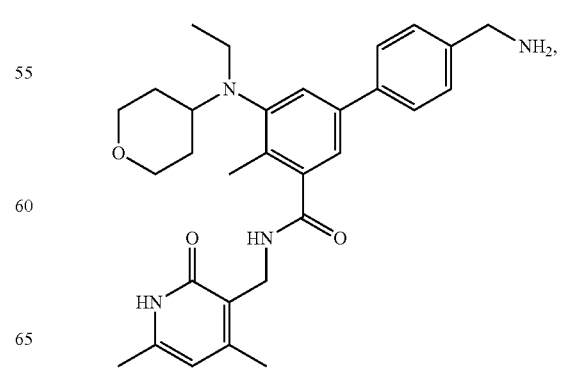

-continued
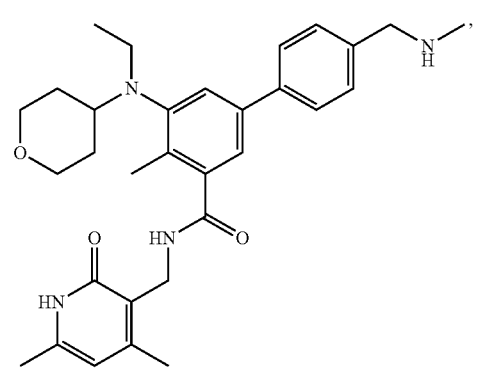
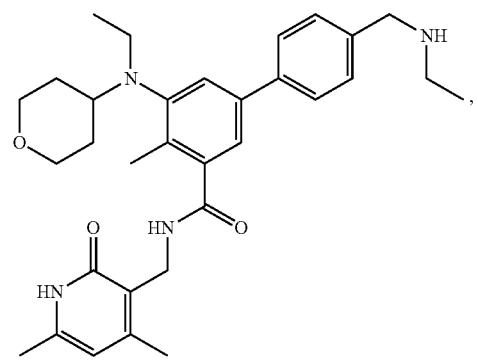
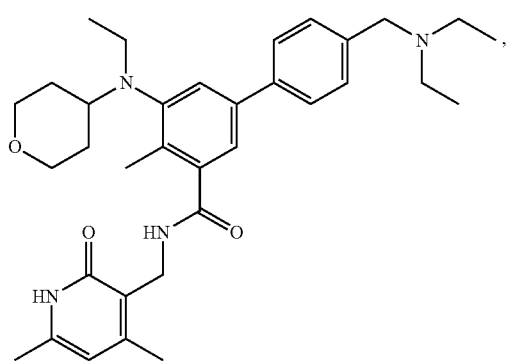
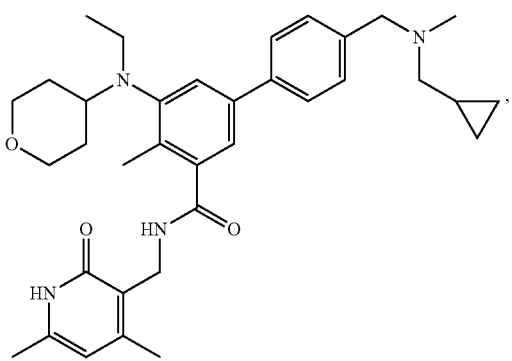
-continued
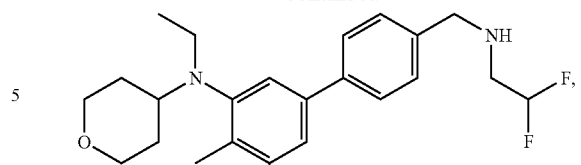
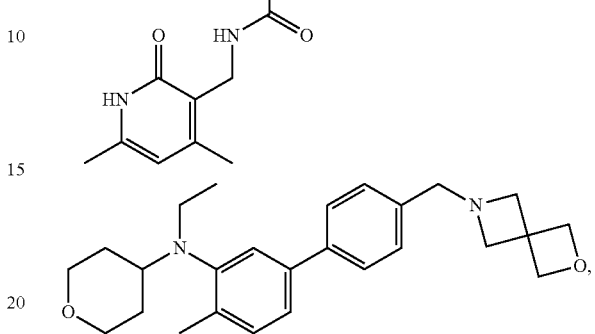
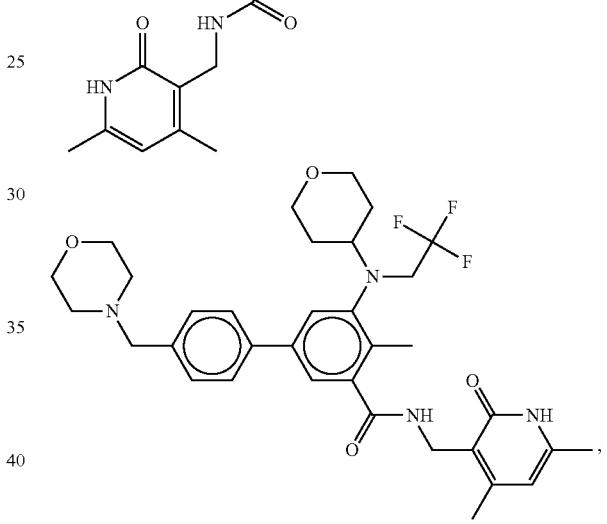
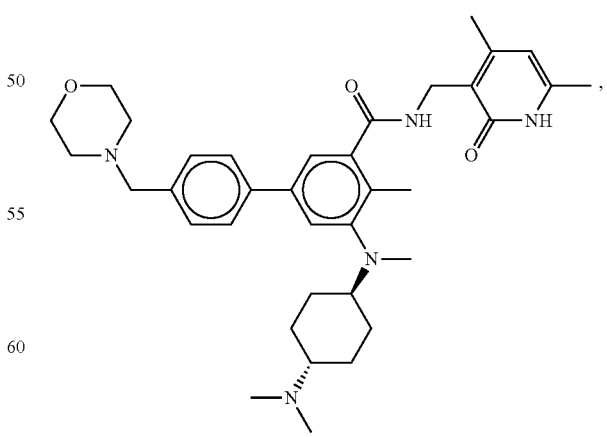
and a pharmaceutically acceptable salt thereof.

In some embodiments, EZH2 inhibitors of the disclosure comprise

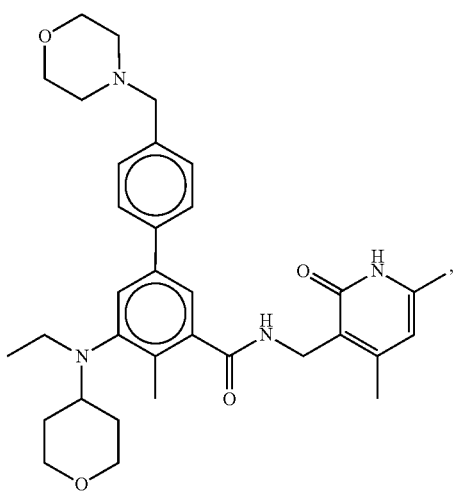

(tazemetostat, EPZ-6438)

or a pharmaceutically-acceptable salt thereof.

In some embodiments, the EZH2 inhibitor is tazemetostat. In some embodiments, the EZH2 inhibitor is the hydrobromide salt of tazemetostat. In some embodiments, the EZH2 inhibitor is the hydrochloride salt of tazemetostat.

In some embodiments, an immune checkpoint inhibitor of the disclosure is a CTLA4 inhibitor. In some embodiments, an immune checkpoint inhibitor of the disclosure targets, binds, or inhibits CTLA4. Exemplary suitable CTLA4 inhibitors of the disclosure include Ipilimumab, Ticilimumab, AGEN-1884 or a combination thereof.

In some embodiments, an immune checkpoint inhibitor of the disclosure is a PD-1 inhibitor. In some embodiments, an immune checkpoint inhibitor of the disclosure targets, binds, or inhibits PD-1 and/or PD-L1. Exemplary suitable PD-1 and/or PD-L1 inhibitors include Nivolumab, Pembrolizumab, Atezolizumab, Durvalumab, Avelumab, BMS-936559, AMP-224, MEDI-0680, TSR-042, BGB-108, STI-1014, KY-1003, ALN-PDL, BGB-A317, KD-033, REGN-2810, PDR-001, SHR-1210, MGD-013, PF-06801591, CX-072 or a combination thereof. In certain embodiments, the immune checkpoint inhibitor comprises Atezolizumab. In certain embodiments, the immune checkpoint inhibitor comprises Nivolumab. In certain embodiments, the immune checkpoint inhibitor comprises Pembrolizumab.

In some embodiments, an immune checkpoint inhibitor of the disclosure is an LAG3 inhibitor. In some embodiments, an immune checkpoint inhibitor of the disclosure targets, binds, or inhibits LAG3. Exemplary suitable LAG3 inhibitors include IMP-731, LAG-525, BMS-986016, GSK-2831781 or a combination thereof.

In some embodiments, an immune checkpoint inhibitor of the disclosure is an B7-H3 inhibitor. In some embodiments, an immune checkpoint inhibitor of the disclosure targets, binds, or inhibits B7-H3. Exemplary suitable B7-H3 inhibitors include Enoblituzumab, 1241-8H9, DS-5573 or a combination thereof.

In some embodiments, an immune checkpoint inhibitor of the disclosure is a Tim3 inhibitor. In some embodiments, an immune checkpoint inhibitor of the disclosure targets, binds, or inhibits Tim3. Exemplary suitable Tim3 inhibitors include MBG-453.

Those of ordinary skill in the art will understand that the exemplary immune checkpoint inhibitors provided herein are non-limiting examples, and are not meant to limit the scope of the present disclosure. Additional suitable immune checkpoint inhibitors will be apparent to the skilled artisan based on the present disclosure and the general knowledge in the art. The disclosure is not limited in this respect.

In some embodiments, the EZH2 inhibitor is a small molecule drug, e.g., tazemetostat, or a pharmaceutically acceptable salt thereof. In some embodiments, the immune checkpoint inhibitor is a peptide, or protein, e.g., a monoclonal antibody, e.g., Nivolumab, Pembrolizumab, Atezolizumab, Durvalumab, or Avelumab. Based on the different bioavailability and pharmacokinetics of small molecule drugs and therapeutic peptides or proteins, the EZH2 inhibitor and the immune checkpoint inhibitor are, in some embodiments, administered via different routes and/or according to different administration schedules.

For example, in some embodiments, the EZH2 inhibitor is a small molecule drug (e.g., tazemetostat or a tazemetostat salt) that is administered daily (e.g., once a day, twice a day, three times a day, and so on) while the immune checkpoint inhibitor is a monoclonal antibody (e.g., Nivolumab, Pembrolizumab, Atezolizumab, Durvalumab, or Avelumab) that is administered at longer time intervals (e.g., once every two days, once every three days, once a week, once every two weeks, once every three weeks, once a month, and so on).

In certain embodiments of the methods of the disclosure, the EZH2 inhibitor and the immune checkpoint inhibitor are administered sequentially. For example, the EZH2 inhibitor may be administered before the immune checkpoint inhibitor. Alternatively, the immune checkpoint inhibitor may be administered before the EZH2 inhibitor. In some embodiments, the EZH2 inhibitor and the immune checkpoint inhibitor are administered in temporal proximity, e.g., one is administrated within one day, 12 hours, 6 hours, 3 hours, 2 hours, 1 hour, 30 minutes, 15 minutes, or 10 minutes before or after administration of the other. In certain embodiments of the methods of the disclosure, the EZH2 inhibitor and the immune checkpoint inhibitor are administered simultaneously. In some embodiments, the administration schedules of the EZH2 inhibitor and the immune checkpoint inhibitor overlap. In some embodiments, the treatment period of the EZH2 inhibitor and the immune checkpoint inhibitor are the same, e.g., about four weeks, about five weeks, about six weeks, about seven weeks, about eight weeks, about ten weeks, about twelve weeks, about fourteen weeks, about sixteen weeks, about eighteen weeks, or about 20 weeks. In some embodiments, the treatment period of the EZH2 inhibitor is longer than the treatment period of the immune checkpoint inhibitor, or vice versa.

A therapeutically effective amount of a pharmaceutical agent provided herein, e.g., of an EZH2 inhibitor or an immune checkpoint inhibitor is, generally, an amount of the agent that is effective in treating, ameliorating, or preventing an identified disease or condition, or to exhibit a clinically desirable effect, e.g., a detectable therapeutic or inhibitory effect. In some embodiments, the effective amount is provided as weight of the pharmaceutical agent, e.g., of an EZH2 inhibitor or an immune checkpoint inhibitor provided herein, per body weight unit, e.g., per kg body weight of the subject being administered the pharmaceutical agent. In some embodiments, the effective amount is provided as a dose per day. Those of skill in the art will understand that an EZH2 inhibitor and/or an immune checkpoint inhibitor provided herein may be administered at a frequency other than once per day, e.g., twice per day, three times a day, once per week, once every two weeks, once every three weeks, once per month, etc., and that the effective daily dose can be determined by calculating the dose the patient receives per day, either cumulatively, where more than one dose is administered per day, or by dividing the total dose by the number of days in the dosage interval (e.g., by 2 where a dose is administered every two days, by 3 where a dose is administered every three days, etc.).

For example, in some embodiments, a therapeutically effective amount of an EZH2 inhibitor and/or of an immune checkpoint inhibitor provided herein is between 1 µg (EZH2 inhibitor)/kg (body weight of the subject) and 1000 mg/kg, inclusive of the endpoints. In some embodiments, a therapeutically effective amount of the EZH2 inhibitor is between 1 µg/kg and 1 mg/kg, 1 µg/kg and 10 mg/kg, 1 µg/kg and 25 mg/kg, 1 µg/kg and 50 mg/kg, 1 µg/kg and 100 mg/kg, 1 µg/kg and 250 mg/kg, 100 µg/kg and 50 mg/kg, 100 µg/kg and 500 mg/kg, 100 µg/kg and 1 mg/kg, 100 µg/kg and 10 mg/kg, 100 µg/kg and 25 mg/kg, 100 µg/kg and 50 mg/kg, 100 µg/kg and 100 mg/kg, 100 µg/kg and 250 mg/kg, 1000 µg/kg and 5 mg/kg, 1000 µg/kg and 10 mg/kg, 1000 µg/kg and 15 mg/kg, 1000 µg/kg and 20 mg/kg, 1000 µg/kg and 25 mg/kg, 1000 µg/kg and 50 mg/kg, 1000 µg/kg and 100 mg/kg, 1000 µg/kg and 250 mg/kg, 1000 µg/kg and 500 mg/kg, 1000 µg/kg and 1000 mg/kg, 2500 µg/kg and 5 mg/kg, 2500 µg/kg and 10 mg/kg, 2500 µg/kg and 15 mg/kg, 2500 µg/kg and 20 mg/kg, 2500 µg/kg and 25 mg/kg, 2500 µg/kg and 50 mg/kg, 2500 µg/kg and 100 mg/kg, 2500 µg/kg and 250 mg/kg, 2500 µg/kg and 500 mg/kg, 2500 µg/kg and 1000 mg/kg, 3000 µg/kg and 5 mg/kg, 5000 µg/kg and 10 mg/kg, 5000 µg/kg and 15 mg/kg, 5000 µg/kg and 20 mg/kg, 10000 µg/kg and 25 mg/kg, 10000 µg/kg and 50 mg/kg, 10000 µg/kg and 100 mg/kg, 10000 µg/kg and 250 mg/kg, 100000 µg/kg and 500 mg/kg, 5 µg/kg and 500 mg/kg, 10 µg/kg and 500 mg/kg, 50 µg/kg and 500 mg/kg, 100 µg/kg and 500 mg/kg, 250 µg/kg and 500 mg/kg, 500 µg/kg and 500 mg/kg, 1000 µg/kg and 500 mg/kg, 5 µg/kg and 100 mg/kg, 10 µg/kg and 100 mg/kg, 50 µg/kg and 100 mg/kg, 100 µg/kg and 100 mg/kg, 250 µg/kg and 100 mg/kg, 500 µg/kg and 100 mg/kg, 1000 µg/kg and 100 mg/kg, 5 µg/kg and 10 mg/kg, 10 µg/kg and 10 mg/kg, 50 µg/kg and 10 mg/kg, 100 µg/kg and 10 mg/kg, 250 µg/kg and 10 mg/kg, 500 µg/kg and 10 mg/kg, 750 µg/kg and 10 mg/kg, 1000 µg/kg and 10 mg/kg, 5 µg/kg and 1 mg/kg, 10 µg/kg and 1 mg/kg, 50 µg/kg and 1 mg/kg, 100 µg/kg and 1 mg/kg, 250 µg/kg and 1 mg/kg, 500 µg/kg and 1 mg/kg, 750 µg/kg and 1 mg/kg, and 750 µg/kg and 1.5 mg/kg inclusive of the endpoints. In some embodiments, a therapeutically effective amount of an EZH2 inhibitor and/or of an immune checkpoint inhibitor provided herein is between 1 µg (EZH2 inhibitor)/kg (body weight of the subject)/day and 1000 mg/kg/day, inclusive of the endpoints. In some embodiments, a therapeutically effective amount of the EZH2 inhibitor is between 1 µg/kg/day and 1 mg/kg/day, 1 µg/kg/day and 10 mg/kg/day, 1 µg/kg/day and 25 mg/kg/day, 1 µg/kg/day and 50 mg/kg/day, 1 µg/kg/day and 100 mg/kg/day, 1 µg/kg/day and 250 mg/kg/day, 100 µg/kg/day and 50 mg/kg/day, 100 µg/kg/day and 500 mg/kg/day, 100 µg/kg/day and 1 mg/kg/day, 100 µg/kg/day and 10 mg/kg/day, 100 µg/kg/day and 25 mg/kg/day, 100 µg/kg/day and 50 mg/kg/day, 100 µg/kg/day and 100 mg/kg/day, 100 µg/kg/day and 250 mg/kg/day, 1000 µg/kg/day and 5 mg/kg/day, 1000 µg/kg/day and 10 mg/kg/day, 1000 µg/kg/day and 15 mg/kg/day, 1000 µg/kg/day and 20 mg/kg/day, 1000 µg/kg/day and 25 mg/kg/day, 1000 µg/kg/day and 50 mg/kg/day, 1000 µg/kg/day and 100 mg/kg/day, 1000 µg/kg/day and 250 mg/kg/day, 1000 µg/kg/day and 500 mg/kg/day, 1000 µg/kg/day and 1000 mg/kg/day, 2500 µg/kg/day and 5 mg/kg/day, 2500 µg/kg/day and 10 mg/kg/day, 2500 µg/kg/day and 15 mg/kg/day, 2500 µg/kg/day and 20 mg/kg/day, 2500 µg/kg/day and 25 mg/kg/day, 2500 µg/kg/day and 50 mg/kg/day, 2500 µg/kg/day and 100 mg/kg/day, 2500 µg/kg/day and 250 mg/kg/day, 2500 µg/kg/day and 500 mg/kg/day, 2500 µg/kg/day and 1000 mg/kg/day, 3000 µg/kg/day and 5 mg/kg/day, 5000 µg/kg/day and 10 mg/kg/day, 5000 µg/kg/day and 15 mg/kg/day, 5000 µg/kg/day and 20 mg/kg/day, 10000 µg/kg/day and 25 mg/kg/day, 10000 µg/kg/day and 50 mg/kg/day, 10000 µg/kg/day and 100 mg/kg/day, 10000 µg/kg/day and 250 mg/kg/day, 100000 µg/kg/day and 500 mg/kg/day, 5 µg/kg/day and 500 mg/kg/day, 10 µg/kg/day and 500 mg/kg/day, 50 µg/kg/day and 500 mg/kg/day, 100 µg/kg/day and 500 mg/kg/day, 250 µg/kg/day and 500 mg/kg/day, 500 µg/kg/day and 500 mg/kg/day, 1000 µg/kg/day and 500 mg/kg/day, 5 µg/kg/day and 100 mg/kg/day, 10 µg/kg/day and 100 mg/kg/day, 50 µg/kg/day and 100 mg/kg/day, 100 µg/kg/day and 100 mg/kg/day, 250 µg/kg/day and 100 mg/kg/day, 500 µg/kg/day and 100 mg/kg/day, 1000 µg/kg/day and 100 mg/kg/day, 5 µg/kg/day and 10 mg/kg/day, 10 µg/kg/day and 10 mg/kg/day, 50 µg/kg/day and 10 mg/kg/day, 100 µg/kg/day and 10 mg/kg/day, 250 µg/kg/day and 10 mg/kg/day, 500 µg/kg/day and 10 mg/kg/day, 750 µg/kg/day and 10 mg/kg/day, and 1000 µg/kg/day, 10 mg/kg/day, 5 µg/kg/day and 1 mg/kg/day, 10 µg/kg/day and 1 mg/kg/day, 50 µg/kg/day and 1 mg/kg/day, 100 µg/kg/day and 1 mg/kg/day, 250 µg/kg/day and 1 mg/kg/day, 500 µg/kg/day and 1 mg/kg/day, 750 µg/kg/day and 1 mg/kg/day, and 750 µg/kg/day and 1.5 mg/kg/day, inclusive of the endpoints. In some embodiments, an effective amount of an EZH2 inhibitor and/or of an immune checkpoint inhibitor provided herein is about 1 µg/kg, about 2 µg/kg, about 2.5 µg/kg, about 5 µg/kg, about 10 µg/kg, about 20 µg/kg, about 25 µg/kg, about 50 µg/kg, about 100 µg/kg, about 200 µg/kg, about 250 µg/kg, about 500 µg/kg, about 1 mg/kg, about 2 mg/kg, about 2.5 mg/kg, about 5 mg/kg, about 10 mg/kg, about 20 mg/kg, about 25 mg/kg, about 50 mg/kg, about 100 mg/kg, about 200 mg/kg, about 250 mg/kg, about 500 mg/kg, or about 1000 mg/kg. In some embodiments, an effective amount of an EZH2 inhibitor and/or of an immune checkpoint inhibitor provided herein is about 1 µg/kg/day, about 2 µg/kg/day, about 2.5 µg/kg/day, about 5 µg/kg/day, about 10 µg/kg/day, about 20 µg/kg/day, about 25 µg/kg/day, about 50 µg/kg/day, about 100 µg/kg/day, about 200 µg/kg/day, about 250 µg/kg/day, about 500 µg/kg/day, about 1 mg/kg/day, about 2 mg/kg/day, about 2.5 mg/kg/day, about 5 mg/kg/day, about 10 mg/kg/day, about 20 mg/kg/day, about 25 mg/kg/day, about 50 mg/kg/day, about 100 mg/kg/day, about 200 mg/kg/day, about 250 mg/kg/day, about 500 mg/kg/day, or about 1000 mg/kg/day. The disclosure embraces methods and treatment strategies using any combination of EZH2 inhibitors and immune checkpoint inhibitors provided herein at any dosage, combination of dosages, administration routes, and dosage intervals, provided herein. For example, in some embodiments, the EZH2 inhibitor (e.g., tazemetostat) is administered at a dosage of about 10 mg/kg per day by administration twice a day, and the immune checkpoint inhibitor (e.g., a monoclonal antibody, such as, for example, Nivolumab, Pembrolizumab, Atezolizumab, Durvalumab, or Avelumab) is administered at a dosage of 500 µg/kg/day and 1 mg/kg/day by administration once every three weeks.

In some embodiments, the EZH2 inhibitor and/or the immune checkpoint inhibitor is administered in a solid or liquid formulation, e.g., in a pill, a tablet, a solution, or a suspension. In some embodiments, a therapeutically effective amount of the EZH2 inhibitor and/or of the immune checkpoint inhibitor, e.g., an effective amount as provided herein, is administered to a subject in a formulation volume between 1 µL and 500 mL, inclusive of the endpoints. In some embodiments, a therapeutically effective amount of the EZH2 inhibitor and/or of the immune checkpoint inhibitor, e.g., an effective amount as provided herein is administered in a formulation volume between 1 mL and 500 mL, 1 mL and 200 mL, 1 mL and 20 mL, 1 mL and 10 mL, 1 mL and 5 mL, 0.5 mL and 5 mL, 0.5 mL and 2 mL, 0.1 mL and 1 mL, or 0.1 mL and 0.5 mL, inclusive of the endpoints. In some embodiments where the EZH2 inhibitor and the immune checkpoint inhibitor are administered in separate formulations to the subject, any combination of such volumes may be used. For example, the EZH2 inhibitor may be administrated orally in a 100 mL suspension, and the checkpoint inhibitor may be administrated by injection of a 1 mL liquid formulation.

In certain embodiments, the EZH2 inhibitor and/or the immune checkpoint inhibitor is administered systemically. In some embodiments, the EZH2 inhibitor and/or the immune checkpoint inhibitor is administered via an oral or a parenteral route. In some embodiments, the EZH2 inhibitor and the immune checkpoint inhibitor are administered via different routes, e.g., one is administered orally and the other parenterally. In certain embodiments, the EZH2 inhibitor is administered orally, e.g., formulated as a capsule, tablet, suspension, or solution for oral administration. In certain embodiments, the immune checkpoint inhibitor is administered via a parenteral route. In some embodiments, the EZH2 inhibitor may be formulated as a solid or liquid, e.g., as a pill, tablet, solution, or suspension, for oral administration and the immune checkpoint inhibitor is formulated as a liquid, e.g., a solution or suspension, for parenteral administration, e.g., for intravenous injection.

In certain embodiments of the methods of this disclosure, the EZH2 inhibitor is administered twice a day at a dosage of 800 mg and the immune checkpoint inhibitor is administered once every three weeks at a dosage of 1200 mg. In certain aspects, the EZH2 inhibitor is a small molecule drug and the immune checkpoint inhibitor is a monoclonal antibody. In certain aspects, the EZH2 inhibitor is administered orally. In certain aspects, the EZH2 inhibitor is administered orally and the immune checkpoint inhibitor is administered parenterally. In certain aspects, the immune checkpoint inhibitor comprises a PD-L1 inhibitor. In certain aspects, the immune checkpoint inhibitor comprises Atezolizumab. In certain aspects, the immune checkpoint inhibitor comprises Nivolumab. In certain aspects, the immune checkpoint inhibitor comprises Pembrolizumab.

It will be understood that the effective amounts, formulation volumes, and administration routes provided herein are non-limiting examples of some embodiments within the scope of this disclosure. Additional suitable amounts and administration routes will be apparent to the person of ordinary skill in the art based on this disclosure and the general knowledge in the art. The present disclosure is not limited in this respect. In some embodiments, the subject being administered the EZH2 inhibitor and the immune checkpoint inhibitor has or is diagnosed with a proliferative disease. In some embodiments, the proliferative disease is a malignant proliferative disease, e.g., a cancer. In some embodiments, a cancer that can be treated by the methods of the disclosure or with the compositions, strategies, treatment modalities, methods, combinations, and compositions of the disclosure comprises or is derived from a stem cell or a progenitor cell.

In some embodiments, cancers that can be treated by the methods of the disclosure or with the compositions, strategies, treatment modalities, methods, combinations, and compositions of the disclosure comprise or are derived from an immune cell. In some embodiments, the cancer is a form of lymphoma, e.g., a B-cell lymphoma, Non-Hodgkins Lymphoma or Diffuse Large B-cell Lymphoma (DLBCL).

In some embodiments, cancers that can be treated by the methods of the disclosure or with the compositions, strategies, treatment modalities, methods, combinations, and compositions of the disclosure comprise or are derived adrenocortical carcinoma, AIDS-related cancers, AIDS-related lymphoma, anal cancer, anorectal cancer, cancer of the anal canal, appendix cancer, childhood cerebellar astrocytoma, childhood cerebral astrocytoma, basal cell carcinoma, skin cancer (non-melanoma), biliary cancer, extrahepatic bile duct cancer, intrahepatic bile duct cancer, bladder cancer, urinary bladder cancer, bone and joint cancer, osteosarcoma and malignant fibrous histiocytoma, brain cancer, brain tumor, brain stem glioma, cerebellar astrocytoma, cerebral astrocytoma/malignant glioma, ependymoma, medulloblastoma, supratentorial primitive neuroectodermal tumors, visual pathway and hypothalamic glioma, breast cancer, bronchial adenomas/carcinoids, carcinoid tumor, gastrointestinal, nervous system cancer, nervous system lymphoma, central nervous system cancer, central nervous system lymphoma, cervical cancer, childhood cancers, chronic lymphocytic leukemia, chronic myelogenous leukemia, chronic myeloproliferative disorders, colon cancer, colorectal cancer, cutaneous T-cell lymphoma, lymphoid neoplasm, mycosis fungoides, Sezary Syndrome, endometrial cancer, esophageal cancer, extracranial germ cell tumor, extragonadal germ cell tumor, extrahepatic bile duct cancer, eye cancer, intraocular melanoma, retinoblastoma, gallbladder cancer, gastric (stomach) cancer, gastrointestinal carcinoid tumor, gastrointestinal stromal tumor (GIST), germ cell tumor, ovarian germ cell tumor, gestational trophoblastic tumor glioma, head and neck cancer, hepatocellular (liver) cancer, Hodgkin lymphoma, hypopharyngeal cancer, intraocular melanoma, ocular cancer, islet cell tumors (endocrine pancreas), Kaposi Sarcoma, kidney cancer, renal cancer, kidney cancer, laryngeal cancer, acute lymphoblastic leukemia, acute myeloid leukemia, chronic lymphocytic leukemia, chronic myelogenous leukemia, hairy cell leukemia, lip and oral cavity cancer, liver cancer, lung cancer, non-small cell lung cancer, small cell lung cancer, AIDS-related lymphoma, non-Hodgkin lymphoma, primary central nervous system lymphoma, Waldenstroem macroglobulinemia, melanoma, intraocular (eye) melanoma, merkel cell carcinoma, mesothelioma malignant, mesothelioma, metastatic squamous neck cancer, mouth cancer, cancer of the tongue, multiple endocrine neoplasia syndrome, mycosis fungoides, myelodysplastic syndromes, myelodysplastic/myeloproliferative diseases, chronic myelogenous leukemia, acute myeloid leukemia, multiple myeloma, chronic myeloproliferative disorders, nasopharyngeal cancer, neuroblastoma, oral cancer, oral cavity cancer, oropharyngeal cancer, ovarian cancer, ovarian epithelial cancer, ovarian low malignant potential tumor, pancreatic cancer, islet cell pancreatic cancer, paranasal sinus and nasal cavity cancer, parathyroid cancer, penile cancer, pharyngeal cancer, pheochromocytoma, pineoblastoma and supratentorial primitive neuroectodermal tumors, pituitary tumor, plasma cell neoplasm/multiple myeloma, pleuropulmonary blastoma, prostate cancer, rectal cancer, renal pelvis and ureter, transitional cell cancer, retinoblastoma, rhabdomyosarcoma, salivary gland cancer, ewing family of sarcoma tumors, Kaposi Sarcoma, soft tissue sarcoma, synovial sarcoma, uterine cancer, uterine sarcoma, skin cancer (non-melanoma), skin cancer (melanoma), merkel cell skin carcinoma, small intestine cancer, soft tissue sarcoma, squamous cell carcinoma, stomach (gastric) cancer, supratentorial primitive neuroectodermal tumors, testicular cancer, throat cancer, thymoma, thymoma and thymic carcinoma, thyroid cancer, transitional cell cancer of the renal pelvis and ureter and other urinary organs, gestational trophoblastic tumor, urethral cancer, endometrial uterine cancer, uterine sarcoma, uterine corpus cancer, vaginal cancer, vulvar cancer, or Wilm's Tumor.

In some embodiments, a cancer that can be treated with the strategies, treatment modalities, methods, combinations, and compositions of the disclosure comprise a solid tumor. In some embodiments, a cancer that can be treated with the strategies, treatment modalities, methods, combinations, and compositions of the disclosure comprises or is derived from a cell of epithelial origin. In some embodiments, cancers that can be treated with the strategies, treatment modalities, methods, combinations, and compositions of the disclosure are primary tumors. In some embodiments, cancers that can be treated with the strategies, treatment modalities, methods, combinations, and compositions of the disclosure are secondary tumors. In some embodiments, the cancer is metastatic.

In certain embodiments of the methods of the disclosure, the subject being administered the EZH2 inhibitor and the immune checkpoint inhibitor has been diagnosed with cancer. In some embodiments, the subject is an adult. In some embodiments, the subject is a pediatric subject. In some embodiments, the subject is a human.

In certain embodiments, the subject is an adult, and the therapeutically effective amount of tazemetostat is about 100 mg to about 1600 mg. In certain embodiments, the subject is an adult, and the therapeutically effective amount of tazemetostat is about 100 mg, 200 mg, 400 mg, 800 mg, or about 1600 mg. In certain embodiments, the subject is an adult, and the therapeutically effective amount of tazemetostat is about 800 mg, e.g., 800 mg/day administered at a dose of 400 mg orally twice a day.

In certain embodiments, the subject is pediatric, and the tazemetostat may be administered at a dose of between 230 mg/m$^2$ and 600 mg/m$^2$ twice per day (BID), inclusive of the endpoints. In certain embodiments, the subject is pediatric, and the tazemetostat is administered at a dose of between 230 mg/m$^2$ and 305 mg/m$^2$ twice per day (BID), inclusive of the endpoints. In certain embodiments, the subject is pediatric, and the tazemetostat is administered at a dose of 240 mg/m$^2$ twice per day (BID). In certain embodiments, the subject is pediatric, and the tazemetostat is administered at a dose of 300 mg/m$^2$ twice per day (BID). In certain embodiments, the subject is pediatric, and the tazemetostat is administered at a dose of about 60% of the area under the curve (AUC) at steady state (AUC$_{SS}$) following administration of 1600 mg twice a day to an adult subject. In certain embodiments, the subject is pediatric, and the tazemetostat is administered at a dose of about 600 mg/m$^2$ per day. In certain embodiments, the subject is pediatric, and the tazemetostat is administered at a dose of at least 600 mg/m$^2$ per day. In certain embodiments, the subject is pediatric, and the tazemetostat is administered at a dose of about 80% of the area under the curve (AUC) at steady state (AUC$_{SS}$) following administration of 800 mg twice a day to an adult subject. In certain embodiments, the subject is pediatric, and tazemetostat is administered at a dose of about 390 mg/m$^2$ twice per day (BID). In certain embodiments, the subject is pediatric, and the tazemetostat is administered at a dose of at least 390 mg/m$^2$ twice per day (BID). In certain embodiments, the subject is pediatric, and the tazemetostat is administered at a dose of between 300 mg/m$^2$ and 600 mg/m$^2$ twice per day (BID).

In some embodiments, e.g., in some embodiments where the subject is pediatric, the EZH2 inhibitor may be formulated as an oral suspension.

In certain embodiments, this disclosure provides a method of treating locally advanced or metastatic urothelial carcinoma (or any other form of cancer) in a subject in need thereof comprising administering to the subject a combination of tazemetostat at an oral dose of 800 mg twice per day and atezolizumab (TECENTRIQ™) at a dose of 1200 mg as an intravenous infusion over 60 minutes every 3 weeks (see, accessdata.fda.gov/drugsatfda_docs/label/2016/761034s0001b1.pdf, the contents of which are incorporated herein for additional information about atezolizumab).

In certain embodiments, this disclosure provides a method of treating Diffuse Large B-Cell Lymphoma (DLBCL) (or any other form of cancer) in a subject in need thereof comprising administering to the subject a combination of tazemetostat at an oral dose of 800 mg twice per day and atezolizumab (TECENTRIQ™) at a dose of 1200 mg as an intravenous infusion over 60 minutes every 3 weeks.

In certain embodiments, this disclosure provides a method of treating Non-Hodgkin's Lymphoma (or any other form of cancer) in a subject in need thereof comprising administering to the subject a combination of tazemetostat at an oral dose of 800 mg twice per day and atezolizumab (TECENTRIQ™) at a dose of 1200 mg as an intravenous infusion over 60 minutes every 3 weeks.

In certain embodiments, this disclosure provides a method of treating melanoma (or any other form of cancer) in a subject in need thereof comprising administering to the subject a combination of tazemetostat at an oral dose of 800 mg twice per day and nivolumab (OPTIVO™) at a dose of 3 mg/kg as an intravenous infusion over 60 minutes every 2 weeks (see, accessdata.fda.gov/drugsatfda_docs/label/2014/125554lb1.pdf, the contents of which are incorporated herein for additional information about nivolumab).

In certain embodiments, this disclosure provides a method of treating melanoma (or any other form of cancer) in a subject having a BRAF V600 mutation comprising administering to the subject a combination of tazemetostat at an oral dose of 800 mg twice per day and nivolumab (OPTIVO™) at a dose of 3 mg/kg as an intravenous infusion over 60 minutes every 2 weeks, and optionally, a BRAF inhibitor.

In certain embodiments, this disclosure provides a method of treating melanoma and disease progression following ipilimumab (or any other form of cancer) in a subject in need thereof comprising administering to the subject a combination of tazemetostat at an oral dose of 800 mg twice per day and pembrolizumab (KEYTRUDA™) at a dose of 2 mg/kg as an intravenous infusion over 30 minutes every 3 weeks (see, accessdata.fda.gov/drugsatfda_docs/label/2014/125514lb1.pdf, the contents of which are incorporated herein for additional information about pembrolizumab).

In certain embodiments, this disclosure provides a method of treating unresectable or metastatic melanoma and disease progression following ipilimumab (or any other form of cancer) in a subject having a BRAF V600 mutation comprising administering to the subject a combination of tazemetostat at an oral dose of 800 mg/kg twice per day and pembrolizumab (KEYTRUDA™) at a dose of 2 mg/kg as an intravenous infusion over 30 minutes every 3 weeks, and optionally, a BRAF inhibitor.

Unless otherwise defined, all technical and scientific terms used herein have the same meaning as commonly understood by one of ordinary skill in the art to which this disclosure belongs. In the specification, the singular forms also include the plural unless the context clearly dictates otherwise. All publications, patent applications, patents and other references mentioned herein are incorporated by reference. The references cited herein are not admitted to be prior art to the claimed invention. In the case of conflict, the present specification, including definitions, will control. In addition, the materials, methods and examples are illustrative only and are not intended to be limiting.

Other features and advantages of the invention will be apparent from the following detailed description and claims.

DETAILED DESCRIPTION

Some aspects of this disclosure provide methods, strategies, treatment modalities, compositions, and combinations for treating diseases, e.g., certain proliferative diseases. In some embodiments, the methods provided herein comprise administering a therapeutically-effective amount of an EZH2 inhibitor and a therapeutically effective amount of an immune checkpoint inhibitor to a subject in need thereof, e.g., a subject having a proliferative disease.

EZH2

EZH2 is a histone methyltransferase that is the catalytic subunit of the PRC2 complex which catalyzes the mono- through tri-methylation of lysine 27 on histone H3 (H3-K27). Histone H3-K27 trimethylation is a mechanism for suppressing transcription of specific genes that are proximal to the site of histone modification. This trimethylation is known to be a cancer marker with altered expression in cancer, such as prostate cancer (see, e.g., U.S. Patent Application Publication No. 2003/0175736; incorporated herein by reference in its entirety). Other studies provided evidence for a functional link between dysregulated EZH2 expression, transcriptional repression, and neoplastic transformation. Varambally et al. (2002) *Nature* 419(6907):624-9 Kleer et al. (2003) *Proc Natl Acad Sci USA* 100(20):11606-11.

Human EZH2 nucleic acids and polypeptides have previously been described. See, e.g., Chen et al. (1996) *Genomics* 38:30-7 [746 amino acids]; Swiss-Prot Accession No. Q15910 [746 amino acids]; GenBank Accession Nos. NM_004456 and NP_004447 (isoform a [751 amino acids]); and GenBank Accession Nos. NM_152998 and NP_694543 (isoform b [707 amino acids]), each of which is incorporated herein by reference in its entirety.

In some embodiments embraced by the scope of this disclosure, the subject being administered an EZH2 inhibitor and an immune checkpoint inhibitor expresses a wild-type EZH2 protein in the cells associated with the proliferative disease in the subject, e.g., in cancer cells in the subject. In some embodiments, the subject expresses a mutant EZH2 protein in the cells associated with the proliferative disease in the subject. In some embodiments, the mutant EZH2 protein comprises a gain-of-function mutation.

For purposes of this application, a Y641 mutant of human EZH2, and, equivalently, a Y641 mutant of EZH2, is to be understood to refer to a human EZH2 in which the amino acid residue corresponding to Y641 of wild-type human EZH2 is substituted by an amino acid residue other than tyrosine.

In some embodiments the amino acid sequence of a Y641 mutant of EZH2 differs from the amino acid sequence of wild-type human EZH2 only by substitution of a single amino acid residue corresponding to Y641 of wild-type human EZH2 by an amino acid residue other than tyrosine.

In some embodiments the amino acid sequence of a Y641 mutant of EZH2 differs from the amino acid sequence of wild-type human EZH2 only by substitution of phenylalanine (F) for the single amino acid residue corresponding to Y641 of wild-type human EZH2. The Y641 mutant of EZH2 according to this embodiment is referred to herein as a Y641F mutant or, equivalently, Y641F.

In some embodiments the amino acid sequence of a Y641 mutant of EZH2 differs from the amino acid sequence of wild-type human EZH2 only by substitution of histidine (H) for the single amino acid residue corresponding to Y641 of wild-type human EZH2. The Y641 mutant of EZH2 according to this embodiment is referred to herein as a Y641H mutant or, equivalently, Y641H.

In some embodiments the amino acid sequence of a Y641 mutant of EZH2 differs from the amino acid sequence of wild-type human EZH2 only by substitution of asparagine (N) for the single amino acid residue corresponding to Y641 of wild-type human EZH2. The Y641 mutant of EZH2 according to this embodiment is referred to herein as a Y641N mutant or, equivalently, Y641N.

In some embodiments the amino acid sequence of a Y641 mutant of EZH2 differs from the amino acid sequence of wild-type human EZH2 only by substitution of serine (S) for the single amino acid residue corresponding to Y641 of wild-type human EZH2. The Y641 mutant of EZH2 according to this embodiment is referred to herein as a Y641S mutant or, equivalently, Y641S.

In some embodiments the amino acid sequence of a Y641 mutant of EZH2 differs from the amino acid sequence of wild-type human EZH2 only by substitution of cysteine (C) for the single amino acid residue corresponding to Y641 of wild-type human EZH2. The Y641 mutant of EZH2 according to this embodiment is referred to herein as a Y641C mutant or, equivalently, Y641C.

In some embodiments the amino acid sequence of a A677 mutant of EZH2 differs from the amino acid sequence of wild-type human EZH2 only by substitution of a non-alanine amino acid, preferably glycine (G) for the single amino acid residue corresponding to A677 of wild-type human EZH2. The A677 mutant of EZH2 according to this embodiment is referred to herein as an A677 mutant, and preferably an A677G mutant or, equivalently, A677G.

In some embodiments the amino acid sequence of a A687 mutant of EZH2 differs from the amino acid sequence of wild-type human EZH2 only by substitution of a non-alanine amino acid, preferably valine (V) for the single amino acid residue corresponding to A687 of wild-type human EZH2. The A687 mutant of EZH2 according to this embodiment is referred to herein as an A687 mutant and preferably an A687V mutant or, equivalently, A687V.

In some embodiments the amino acid sequence of a R685 mutant of EZH2 differs from the amino acid sequence of wild-type human EZH2 only by substitution of a non-arginine amino acid, preferably histidine (H) or cysteine (C) for the single amino acid residue corresponding to R685 of wild-type human EZH2. The R685 mutant of EZH2 according to this embodiment is referred to herein as an R685 mutant and preferably an R685C mutant or an R685H mutant or, equivalently, R685H or R685C.

Cells heterozygous for EZH2 would be expected to display a malignant phenotype due to the efficient formation of H3-K27me1 by the WT enzyme and the efficient, subsequent transition of this progenitor species to H3-K27me2, and, especially, H3-K27me3, by the mutant enzyme form(s).

Some aspects of the disclosure provide methods for treating or alleviating a symptom of cancer or precancerous condition in a subject by administering to a subject expressing either a wild type or a mutant EZH2 a therapeutically effective amount of an EZH2 inhibitor and an immune checkpoint modulator as described herein. In certain embodiments, the EZH2 inhibitor is tazemetostat or a pharmaceutically acceptable salt thereof.

Some aspects of this disclosure provide methods for inhibiting in a subject conversion of H3-K27 to trimethylated H3-K27, while also inhibiting an immune checkpoint in the subject. The inhibition of the conversion from H3-K27 to trimethylated H3-K27 involves, in some embodiments, inhibiting in a subject conversion of unmethylated H3-K27 to monomethylated H3-K27, conversion of monomethylated H3-K27 to dimethylated H3-K27, conversion of dimethylated H3-K27 to trimethylated H3-K27, or any combination thereof, including, for example, conversion of monomethylated H3-K27 to dimethylated H3-K27 and conversion of dimethylated H3-K27 to trimethylated H3-K27. As used herein, unmethylated H3-K27 refers to histone H3 with no methyl group covalently linked to the amino group of lysine 27. As used herein, monomethylated H3-K27 refers to histone H3 with a single methyl group covalently linked to the amino group of lysine 27. Monomethylated H3-K27 is also referred to herein as H3-K27me1. As used herein, dimethylated H3-K27 refers to histone H3 with two methyl groups covalently linked to the amino group of lysine 27. Dimethylated H3-K27 is also referred to herein as H3-K27me2. As used herein, trimethylated H3-K27 refers to histone H3 with three methyl groups covalently linked to the amino group of lysine 27. Trimethylated H3-K27 is also referred to herein as H3-K27me3.

Histone H3 is a 136 amino acid long protein, the sequence of which is known. See, for example, GenBank Accession No. CAB02546, the content of which is incorporated herein by reference. As disclosed further herein, in addition to full-length histone H3, peptide fragments of histone H3 comprising the lysine residue corresponding to K27 of full-length histone H3 can be used as substrate for EZH2 (and likewise for mutant forms of EZH2) to assess conversion of H3-K27m1 to H3-K27m2 and conversion of H3-K27m2 to H3-K27m3. In some embodiments, such peptide fragment corresponds to amino acid residues 21-44 of histone H3.

EZH2 Inhibitors

Various small molecule EZH2 inhibitors have previously been described. Some non-limiting examples of EZH2 inhibitors that are suitable for use in the strategies, treatment modalities, methods, combinations, and compositions provided herein are those described in U.S. Pat. Nos. 8,410,088, 8,765,732, 9,090,562, 8,598,167, 8,962,620, US-2015/0065483, U.S. Pat. Nos. 9,206,157, 9,006,242, 9,089,575, US 2015-0352119, WO 2014/062733, US-2015/0065503, WO2015/057859, U.S. Pat. No. 8,536,179, WO 2011/140324, PCT/US2014/015706, published as WO/2014/124418, in PCT/US2013/025639, published as WO/2013/120104, and in U.S. Ser. No. 14/839,273, published as US 2015/0368229, the entire contents of each of which are incorporated herein by reference.

In some embodiments, an EZH2 inhibitor suitable for use in the strategies, treatment modalities, methods, combinations, and compositions described herein has the following Formula (I):

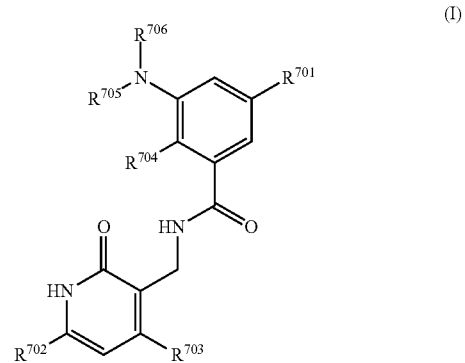

or a pharmaceutically acceptable salt thereof; wherein $R^{701}$ is H, F, $OR^{707}$, $NHR^{707}$, —(C≡C)—$(CH_2)_{n7}$—$R^{708}$, phenyl, 5- or 6-membered heteroaryl, $C_{3-8}$ cycloalkyl, or 4-7 membered heterocycloalkyl containing 1-3 heteroatoms, wherein the phenyl, 5- or 6-membered heteroaryl, $C_{3-8}$ cycloalkyl or 4-7 membered heterocycloalkyl each independently is optionally substituted with one or more groups selected from halo, $C_{1-3}$ alkyl, OH, O—$C_{1-6}$ alkyl, NH—$C_{1-6}$ alkyl, and, $C_{1-3}$ alkyl substituted with $C_{3-8}$ cycloalkyl or 4-7 membered heterocycloalkyl containing 1-3 heteroatoms, wherein each of the O—$C_{1-6}$ alkyl and NH—$C_{1-6}$ alkyl is optionally substituted with hydroxyl, O—$C_{1-3}$ alkyl or NH—$C_{1-3}$ alkyl, each of the O—$C_{1-3}$ alkyl and NH—$C_{1-3}$ alkyl being optionally further substituted with O—$C_{1-3}$ alkyl or NH—$C_{1-3}$ alkyl;

each of $R^{702}$ and $R^{703}$, independently is H, halo, $C_{1-4}$ alkyl, $C_{1-6}$ alkoxyl or $C_6$-$C_{10}$ aryloxy, each optionally substituted with one or more halo;

each of $R^{704}$ and $R^{705}$, independently is $C_{1-4}$ alkyl;

$R^{706}$ is cyclohexyl substituted by N($C_{1-4}$ alkyl)$_2$ wherein one or both of the $C_{1-4}$ alkyl is optionally substituted with $C_{1-6}$ alkoxy; or $R^{706}$ is tetrahydropyranyl;

$R^{707}$ is $C_{1-4}$ alkyl optionally substituted with one or more groups selected from hydroxyl, $C_{1-4}$ alkoxy, amino, mono- or di-$C_{1-4}$ alkylamino, $C_{3-8}$ cycloalkyl, and 4-7 membered heterocycloalkyl containing 1-3 heteroatoms, wherein the $C_{3-8}$ cycloalkyl or 4-7 membered heterocycloalkyl each independently is further optionally substituted with $C_{1-3}$ alkyl;

$R^{708}$ is $C_{1-4}$ alkyl optionally substituted with one or more groups selected from OH, halo, and $C_{1-4}$ alkoxy, 4-7 membered heterocycloalkyl containing 1-3 heteroatoms, or O—$C_{1-6}$ alkyl, wherein the 4-7 membered heterocycloalkyl can be optionally further substituted with OH or $C_{1-6}$ alkyl; and $n_7$ is 0, 1 or 2.

For example, $R^{706}$ is cyclohexyl substituted by N($C_{1-4}$ alkyl)$_2$ wherein one of the $C_{1-4}$ alkyl is unsubstituted and the other is substituted with methoxy.

For example, $R^{706}$ is

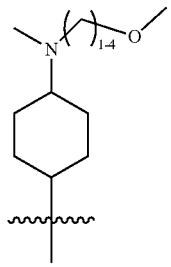

For example, the compound is of Formula II:

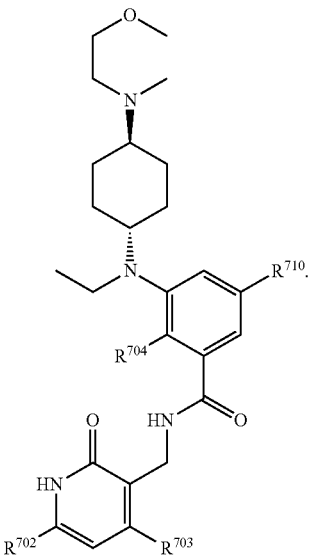

(II)

For example, $R^{702}$ is methyl or isopropyl and $R^{703}$ is methyl or methoxyl.

For example, $R^{704}$ is methyl.

For example, $R^{701}$ is $OR^{707}$ and $R^{707}$ is $C_{1-3}$ alkyl optionally substituted with $OCH_3$ or morpholine.

For example, $R^{701}$ is H or F.

For example, $R^{701}$ is tetrahydropyranyl, phenyl, pyridyl, pyrimidyl, pyrazinyl, imidazolyl, or pyrazolyl, each of which is optionally substituted with methyl, methoxy, ethyl substituted with morpholine, or —$OCH_2CH_2OCH_3$.

For example, $R^{708}$ is morpholine, piperidine, piperazine, pyrrolidine, diazepane, or azetidine, each of which is optionally substituted with OH or $C_{1-6}$ alkyl.

For example, $R^{708}$ is morpholine

For example, $R^{708}$ is piperazine substituted with $C_{1-6}$ alkyl.

For example, $R^{708}$ is methyl, t-butyl or $C(CH_3)_2OH$.

In some embodiments, an EZH2 inhibitor that can be used in the strategies, treatment modalities, methods, combinations, and compositions described herein may have the following Formula III:

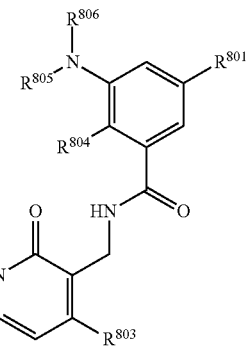

(III)

or a pharmaceutically acceptable salt thereof.

In this formula:

$R^{801}$ is $C_{1-6}$ alkyl, $C_{2-6}$ alkenyl, $C_{2-6}$ alkynyl, $C_{3-8}$ cycloalkyl, 4-7 membered heterocycloalkyl containing 1-3 heteroatoms, phenyl or 5- or 6-membered heteroaryl, each of which is substituted with O—$C_{1-6}$ alkyl-$R_x$ or NH—$C_{1-6}$ alkyl-$R_x$, wherein $R_x$ is hydroxyl, O—$C_{1-3}$ alkyl or NH—$C_{1-3}$ alkyl, and $R_x$ is optionally further substituted with O—$C_{1-3}$ alkyl or NH—$C_{1-3}$ alkyl except when $R_x$ is hydroxyl; or $R^{801}$ is phenyl substituted with -$Q_2$-$T_2$, wherein $Q_2$ is a bond or $C_1$-$C_3$ alkyl linker optionally substituted with halo, cyano, hydroxyl or $C_1$-$C_6$ alkoxy, and $T_2$ is optionally substituted 4- to 12-membered heterocycloalkyl; and $R^{801}$ is optionally further substituted;

each of $R^{802}$ and $R^{803}$, independently is H, halo, $C_{1-4}$ alkyl, $C_{1-6}$ alkoxyl or $C_6$-$C_{10}$ aryloxy, each optionally substituted with one or more halo;

each of $R^{804}$ and $R^{805}$, independently is $C_{1-4}$ alkyl; and $R^{806}$ is -$Q_x$-$T_x$, wherein $Q_x$ is a bond or $C_{1-4}$ alkyl linker, $T_x$ is H, optionally substituted $C_{1-4}$ alkyl, optionally substituted $C_3$-$C_8$ cycloalkyl or optionally substituted 4- to 14-membered heterocycloalkyl.

For example, each of $Q_x$ and $Q_2$ independently is a bond or methyl linker, and each of $T_x$ and $T_2$ independently is tetrahydropyranyl, piperidinyl substituted by 1, 2, or 3 $C_{1-4}$ alkyl groups, or cyclohexyl substituted by $N(C_{1-4}$ alkyl$)_2$ wherein one or both of the $C_{1-4}$ alkyl is optionally substituted with $C_{1-6}$ alkoxy;

For example, $R^{806}$ is cyclohexyl substituted by $N(C_{1-4}$ alkyl$)_2$ or $R^{806}$ is tetrahydropyranyl.

For example, $R^{806}$ is

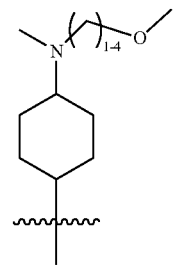

For example, $R^{801}$ is phenyl or 5- or 6-membered heteroaryl substituted with O—$C_{1-6}$ alkyl-$R_x$, or $R^{801}$ is phenyl substituted with $CH_2$-tetrahydropyranyl.-

For example, in some embodiments, a compound according to some aspects of the present disclosure is of Formula IVa or IVb:

(IVa)

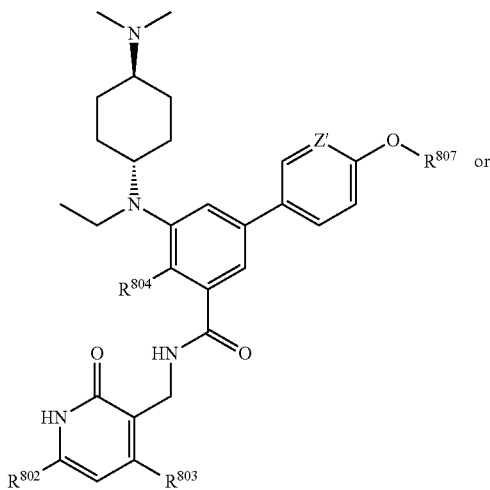

(IVb)

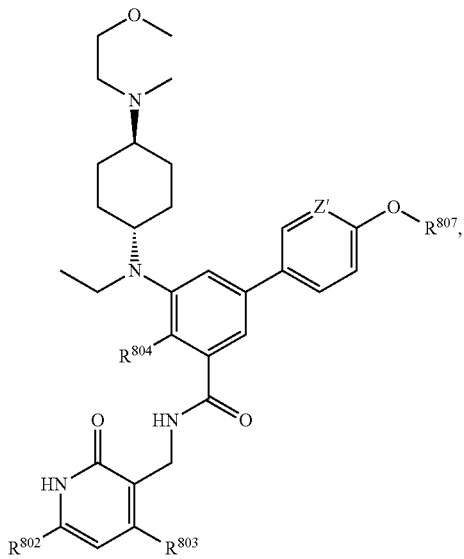

wherein Z' is CH or N, and $R^{807}$ is $C_{2-3}$ alkyl-$R_x$.

For example, $R^{807}$ is —$CH_2CH_2OH$, —$CH_2CH_2OCH_3$, or —$CH_2CH_2OCH_2CH_2OCH_3$.

For example, $R^{802}$ is methyl or isopropyl and $R^{803}$ is methyl or methoxyl.

For example, $R^{804}$ is methyl.

In some embodiments, a compound of the present disclosure may have the following Formula (V):

(V)

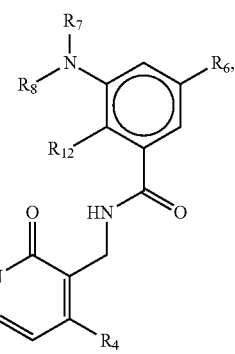

or a pharmaceutically acceptable salt or ester thereof.

In this formula:

$R_2$, $R_4$ and $R_{12}$ are each, independently $C_{1-6}$ alkyl;

$R_6$ is $C_6$-$C_{10}$ aryl or 5- or 6-membered heteroaryl, each of which is optionally substituted with one or more -$Q_2$-$T_2$, wherein $Q_2$ is a bond or $C_1$-$C_3$ alkyl linker optionally substituted with halo, cyano, hydroxyl or $C_1$-$C_6$ alkoxy, and $T_2$ is H, halo, cyano, —$OR_a$, —$NR_aR_b$, —$(NR_aR_bR_c)^+A^-$, —$C(O)R_a$, —$C(O)OR_a$, —$C(O)NR_aR_b$, —$NR_bC(O)R_a$, —$NR_bC(O)OR_a$, —$S(O)_2R_a$, —$S(O)_2NR_aR_b$, or $R_{S2}$, in which each of $R_a$, $R_b$, and $R_c$, independently is H or $R_{S3}$, $A^-$ is a pharmaceutically acceptable anion, each of $R_{S2}$ and $R_{S3}$, independently, is $C_1$-$C_6$ alkyl, $C_3$-$C_8$ cycloalkyl, $C_6$-$C_{10}$ aryl, 4 to 12-membered heterocycloalkyl, or 5- or 6-membered heteroaryl, or $R_a$ and $R_b$, together with the N atom to which they are attached, form a 4 to 12-membered heterocycloalkyl ring having 0 or 1 additional heteroatom, and each of $R_{S2}$, $R_{S3}$, and the 4 to 12-membered heterocycloalkyl ring formed by $R_a$ and $R_b$, is optionally substituted with one or more -$Q_3$-$T_3$, wherein $Q_3$ is a bond or $C_1$-$C_3$ alkyl linker each optionally substituted with halo, cyano, hydroxyl or $C_1$-$C_6$ alkoxy, and $T_3$ is selected from the group consisting of halo, cyano, $C_1$-$C_6$ alkyl, $C_3$-$C_8$ cycloalkyl, $C_6$-$C_{10}$ aryl, 4 to 12-membered heterocycloalkyl, 5- or 6-membered heteroaryl, $OR_d$, $COOR_d$, —$S(O)_2R_d$, —$NR_dR_e$, and —$C(O)NR_dR_e$, each of $R_d$ and $R_e$ independently being H or $C_1$-$C_6$ alkyl, or -$Q_3$-$T_3$ is oxo; or any two neighboring -$Q_2$-$T_2$, together with the atoms to which they are attached form a 5- or 6-membered ring optionally containing 1-4 heteroatoms selected from N, O and S and optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl;

$R_7$ is -$Q_4$-$T_4$, in which $Q_4$ is a bond, $C_1$-$C_4$ alkyl linker, or $C_2$-$C_4$ alkenyl linker, each linker optionally substituted with halo, cyano, hydroxyl or $C_1$-$C_6$ alkoxy, and $T_4$ is H, halo, cyano, $NR_fR_g$, —$OR_f$ —$C(O)R_f$ —$C(O)OR_f$ —$C(O)NR_fR_g$, —$C(O)NR_fOR_g$, —$NR_fC(O)R_g$, —S(O)₂R$_f$, or R$_{S4}$, in which each of R$_f$ and R$_g$, independently is H or R$_{S5}$, each of R$_{S4}$ and R$_{S5}$, independently is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 12-membered heterocycloalkyl, or 5- or 6-membered heteroaryl, and each of R$_{S4}$ and R$_{S5}$ is optionally substituted with one or more -Q$_5$-T$_5$, wherein Q$_5$ is a bond, C(O), C(O)NR$_k$, NR$_k$C(O), S(O)$_2$, or $C_1$-$C_3$ alkyl linker, R$_k$ being H or $C_1$-$C_6$ alkyl, and T$_5$ is H, halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, 5- or 6-membered heteroaryl, or S(O)$_q$R$_q$ in which q is 0, 1, or 2 and R$_q$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 12-membered heterocycloalkyl, or 5- or 6-membered heteroaryl, and T$_5$ is optionally substituted with one or more substituents selected from the group consisting of halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl except when T$_5$ is H, halo, hydroxyl, or cyano; or -Q$_5$-T$_5$ is oxo; and R$_8$ is H, halo, hydroxyl, COOH, cyano, R$_{S6}$, OR$_{S6}$, or COOR$_{S6}$, in which R$_{S6}$ is $C_1$-$C_6$ alkyl, $C_2$-$C_6$ alkenyl, $C_2$-$C_6$ alkynyl, $C_3$-$C_8$ cycloalkyl, 4 to 12-membered heterocycloalkyl, amino, mono-$C_1$-$C_6$ alkylamino, or di-$C_1$-$C_6$ alkylamino, and R$_{S6}$ is optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, and di-$C_1$-$C_6$ alkylamino; or R$_7$ and R$_8$, together with the N atom to which they are attached, form a 4 to 11-membered heterocycloalkyl ring having 0 to 2 additional heteroatoms, and the 4 to 11-membered heterocycloalkyl ring formed by R$_7$ and R$_8$ is optionally substituted with one or more -Q$_6$-T$_6$, wherein Q$_6$ is a bond, C(O), C(O)NR$_m$, NR$_m$C(O), S(O)$_2$, or $C_1$-$C_3$ alkyl linker, R$_m$ being H or $C_1$-$C_6$ alkyl, and T$_6$ is H, halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, 5- or 6-membered heteroaryl, or S(O)$_p$R$_p$ in which p is 0, 1, or 2 and R$_p$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 12-membered heterocycloalkyl, or 5- or 6-membered heteroaryl, and T$_6$ is optionally substituted with one or more substituents selected from the group consisting of halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl except when T$_6$ is H, halo, hydroxyl, or cyano; or -Q$_6$-T$_6$ is oxo.

For example, R$_6$ is $C_6$-$C_{10}$ aryl or 5- or 6-membered heteroaryl, each of which is optionally, independently substituted with one or more -Q$_2$-T$_2$, wherein Q$_2$ is a bond or $C_1$-$C_3$ alkyl linker, and T$_2$ is H, halo, cyano, —OR$_a$, —NR$_a$R$_b$, —(NR$_a$R$_b$R$_c$)$^+$A$^-$, —C(O)NR$_a$R$_b$, —NR$_a$C(O)R$_a$, —S(O)$_2$R$_a$, or R$_{S2}$, in which each of R$_a$ and R$_b$, independently is H or R$_{S3}$, each of R$_{S2}$ and R$_{S3}$, independently, is $C_1$-$C_6$ alkyl, or R$_a$ and R$_b$, together with the N atom to which they are attached, form a 4 to 7-membered heterocycloalkyl ring having 0 or 1 additional heteroatom, and each of R$_{S2}$, R$_{S3}$, and the 4 to 7-membered heterocycloalkyl ring formed by R$_a$ and R$_b$, is optionally, independently substituted with one or more -Q$_3$-T$_3$, wherein Q$_3$ is a bond or $C_1$-$C_3$ alkyl linker and T$_3$ is selected from the group consisting of halo, $C_1$-$C_6$ alkyl, 4 to 7-membered heterocycloalkyl, OR$_d$, —S(O)$_2$R$_d$, and —NR$_d$R$_e$, each of R$_d$ and R$_e$ independently being H or $C_1$-$C_6$ alkyl, or -Q$_3$-T$_3$ is oxo; or any two neighboring -Q$_2$-T$_2$, together with the atoms to which they are attached form a 5- or 6-membered ring optionally containing 1-4 heteroatoms selected from N, O and S.

In some embodiments, the compound is of Formula (VI):

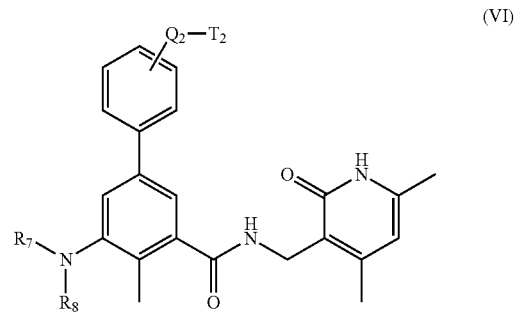

(VI)

or a pharmaceutically acceptable salt thereof, wherein Q$_2$ is a bond or methyl linker, T$_2$ is H, halo, —OR$_a$, —NR$_a$R$_b$, —(NR$_a$R$_b$R$_c$)$^+$A$^-$, or —S(O)$_2$NR$_a$R$_b$, R$_7$ is piperidinyl, tetrahydropyran, cyclopentyl, or cyclohexyl, each optionally substituted with one -Q$_5$-T$_5$ and R$_8$ is ethyl.

Some aspects of the present disclosure provide the compounds of Formula (VIa):

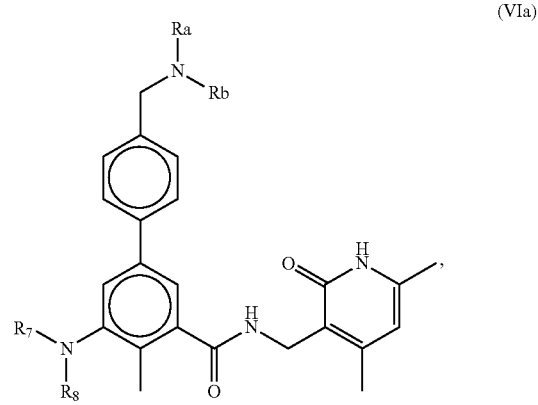

(VIa)

or a pharmaceutically acceptable salts or esters thereof, wherein R$_7$, R$_8$, R$_a$, and R$_b$ are defined herein.

The compounds of Formula (VIa) can include one or more of the following features:

For example, each of R$_a$ and R$_b$ independently is H or $C_1$-$C_6$ alkyl optionally substituted with one or more -Q$_3$-T$_3$.

For example, one of R$_a$ and R$_b$ is H.

For example, R$_a$ and R$_b$, together with the N atom to which they are attached, form a 4 to 7-membered heterocycloalkyl ring having 0 or 1 additional heteroatoms to the N atom (e.g., azetidinyl, pyrrolidinyl, imidazolidinyl, pyrazolidinyl, oxazolidinyl, isoxazolidinyl, triazolidinyl, piperidinyl, 1,2,3,6-tetrahydropyridinyl, piperazinyl, morpholinyl, 1,4-diazepanyl, 1,4-oxazepanyl, 2-oxa-5-azabicyclo[2.2.1]heptanyl, 2,5-diazabicyclo[2.2.1]heptanyl, and the like) and the ring is optionally substituted with one or more -$Q_3$-$T_3$.

For example, $R_a$ and $R_b$, together with the N atom to which they are attached, form azetidinyl, pyrrolidinyl, imidazolidinyl, pyrazolidinyl, oxazolidinyl, isoxazolidinyl, triazolidinyl, tetrahydrofuranyl, piperidinyl, 1,2,3,6-tetrahydropyridinyl, piperazinyl, or morpholinyl, and the ring is optionally substituted with one or more -$Q_3$-$T_3$.

For example, one or more -$Q_3$-$T_3$ are oxo.

For example, $Q_3$ is a bond or unsubstituted or substituted $C_1$-$C_3$ alkyl linker.

For example, $T_3$ is H, halo, 4 to 7-membered heterocycloalkyl, $C_1$-$C_3$ alkyl, $OR_d$, $COOR_d$, —$S(O)_2R_d$, or —$NR_dR_e$.

For example, each of $R_d$ and $R_e$ independently being H or $C_1$-$C_6$ alkyl.

For example, $R_7$ is $C_3$-$C_8$ cycloalkyl or 4 to 7-membered heterocycloalkyl, each optionally substituted with one or more -$Q_5$-$T_5$.

For example, $R_7$ is piperidinyl, tetrahydropyran, tetrahydro-2H-thiopyranyl, cyclopentyl, cyclohexyl, pyrrolidinyl, or cycloheptyl, each optionally substituted with one or more -$Q_5$-$T_5$.

For example, $R_7$ is cyclopentyl cyclohexyl or tetrahydro-2H-thiopyranyl, each of which is optionally substituted with one or more -$Q_5$-$T_5$.

For example, $Q_5$ is NHC(O) and $T_5$ is $C_1$-$C_6$ alkyl or $C_1$-$C_6$ alkoxy, each For example, one or more -$Q_5$-$T_5$ are oxo.

For example, $R_7$ is 1-oxide-tetrahydro-2H-thiopyranyl or 1,1-dioxide-tetrahydro-2H-thiopyranyl.

For example, $Q_5$ is a bond and $T_5$ is amino, mono-$C_1$-$C_6$ alkylamino, di-$C_1$-$C_6$ alkylamino.

For example, $Q_5$ is CO, $S(O)_2$, or NHC(O); and $T_5$ is $C_1$-$C_6$ alkyl, $C_1$-$C_6$ alkoxyl, $C_3$-$C_8$ cycloalkyl, or 4 to 7-membered heterocycloalkyl.

For example, $R_8$ is H or $C_1$-$C_6$ alkyl which is optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, and di-$C_1$-$C_6$ alkylamino.

For example, $R_8$ is H, methyl, or ethyl.

Other compounds of Formulae (I)-(VIa) suitable for use in the strategies, treatment modalities, methods, combinations, and compositions provided herein are described in U.S. Publication 20120264734, the contents of which are hereby incorporated by reference in their entireties. The compounds of Formulae (I)-(VIa) are suitable for administration as part of a combination therapy with one or more other therapeutic agents, e.g., with an immune checkpoint inhibitor as provided herein.

In some embodiments of the strategies, treatment modalities, methods, combinations, and compositions provided herein, the EZH2 inhibitor is Compound 44

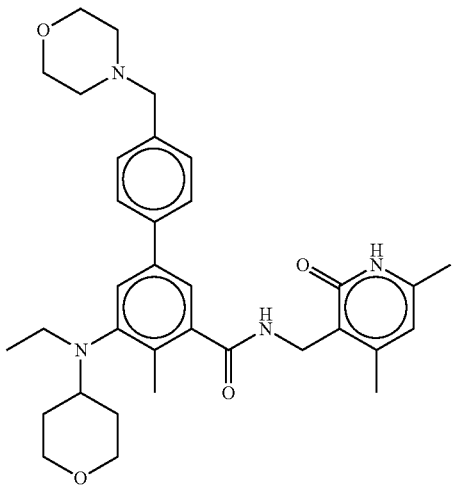

or a pharmaceutically acceptable salt thereof.

Compound 44 or a pharmaceutically acceptable salt thereof, as described herein, is potent in targeting both wild type and mutant EZH2. Compound 44 is orally bioavailable and has high selectivity to EZH2 compared with other histone methyltransferases (i.e. >20,000 fold selectivity by Ki). Importantly, Compound 44 has target methyl mark inhibition that results in the killing of genetically defined cancer cells in vitro. Animal models have also shown sustained in vivo efficacy following inhibition of target methyl mark.

In some embodiments, Compound 44 or a pharmaceutically acceptable salt thereof is administered to the subject at a dose of approximately 100 mg to approximately 3200 mg daily, such as about 100 mg BID to about 1600 mg BID (e.g., 100 mg BID, 200 mg BID, 400 mg BID, 800 mg BID, or 1600 mg BID), for treating a germinal center-derived lymphoma.

In some embodiments, Compound 44 or a pharmaceutically acceptable salt thereof is administered to a subject in combination (either simultaneously or sequentially) with an immune checkpoint inhibitor provided herein.

In some embodiments, a compound that can be used in the strategies, treatment modalities, methods, combinations, and compositions presented here is:

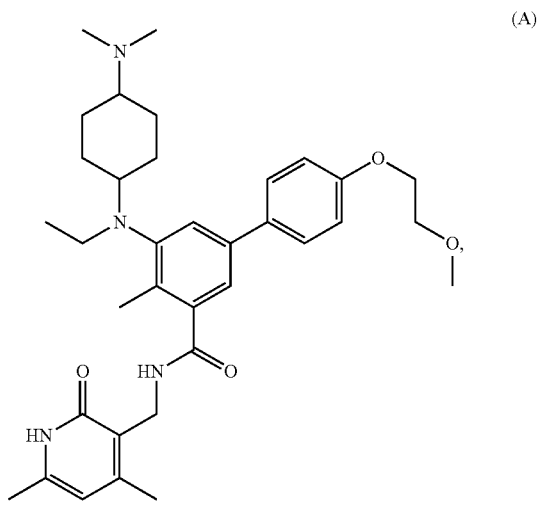

(A)

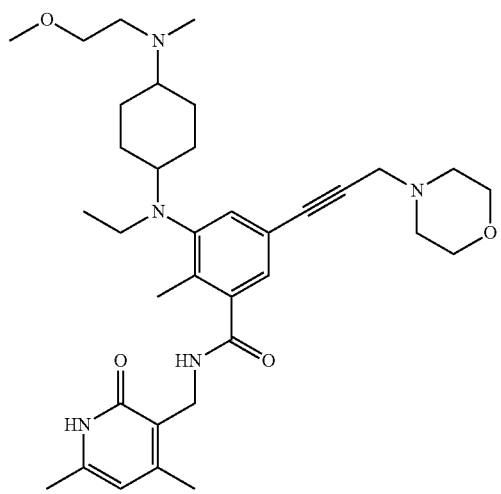

(B)

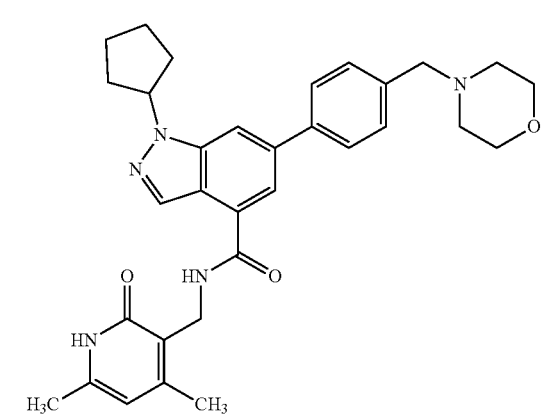

(E)

or stereoisomers thereof or pharmaceutically acceptable salts and solvates thereof.

In some embodiments, the EZH2 inhibitor may comprise, consist essentially of or consist of GSK-126, having the following formula:

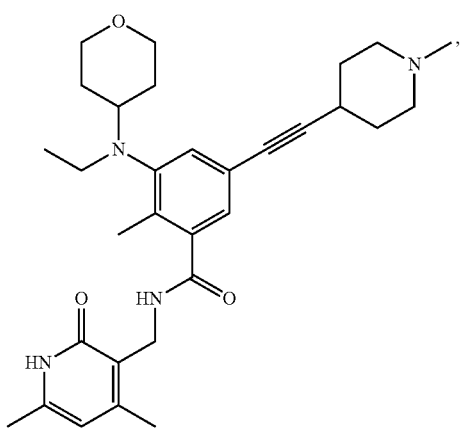

(C)

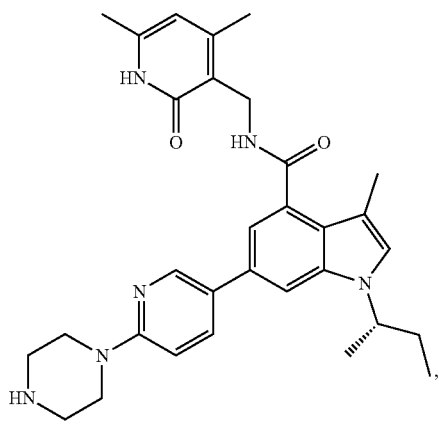 [SMILES: CC[C@H](C)n1cc(C)c2c(C(=O)NCc3c(C)cc(C)[nH]c3=O)cc(-c3ccc(N4CCNCC4)nc3)cc21]

stereoisomers thereof, pharmaceutically acceptable salts or solvates thereof. In some embodiments of the strategies, treatment modalities, methods, combinations, and compositions provided herein, the EZH2 inhibitor is an EZH2 inhibitor described in U.S. Pat. No. 8,536,179 (describing GSK-126 among other compounds and corresponding to WO 2011/140324), the entire contents of each of which are incorporated herein by reference.

In some embodiments of the strategies, treatment modalities, methods, combinations, and compositions provided herein, the EZH2 inhibitor is

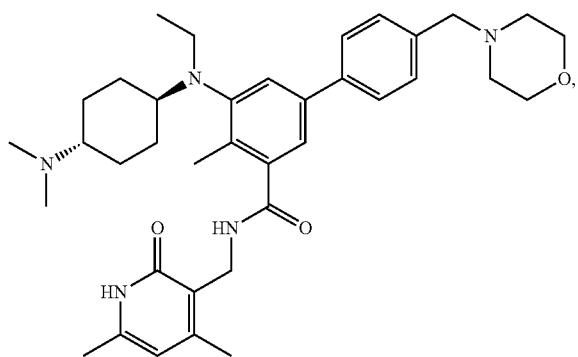

(D)

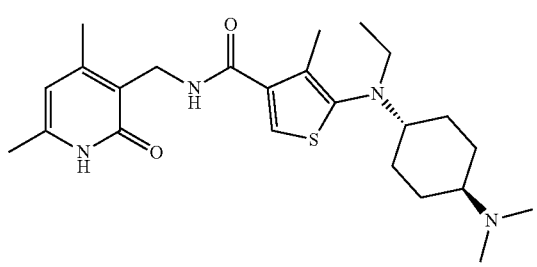

or stereoisomers thereof or pharmaceutically acceptable salts and solvates thereof.

In some embodiments of the strategies, treatment modalities, methods, combinations, and compositions provided herein, the EZH2 inhibitor is any of Compounds Ga-Gc:

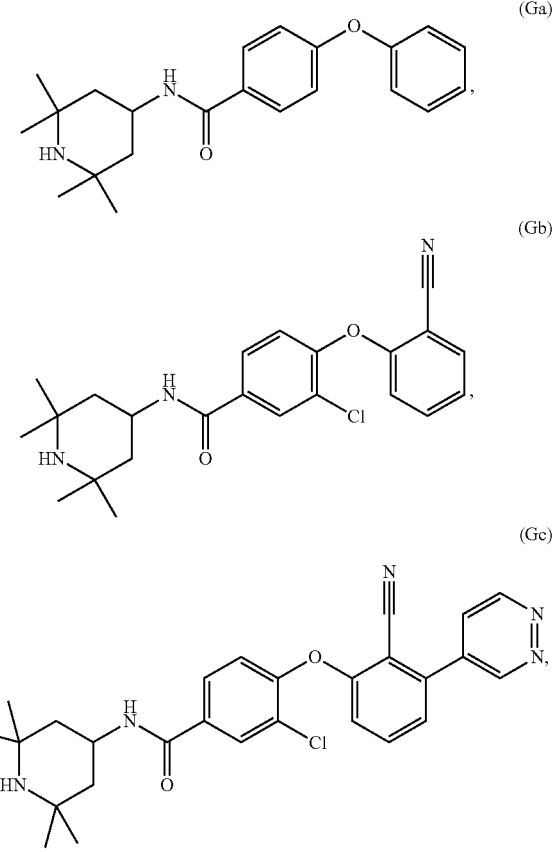

or a stereoisomer, pharmaceutically acceptable salt or solvate thereof.

In some embodiments of the strategies, treatment modalities, methods, combinations, and compositions provided herein, the EZH2 inhibitor may comprise, consist essentially of or consist of CPI-1205 or GSK343.

In some embodiments of the strategies, treatment modalities, methods, combinations, and compositions provided herein, the EZH2 inhibitor is an EZH2 inhibitor described in PCT/US2014/015706, published as WO 2014/124418, in PCT/US2013/025639, published as WO 2013/120104, and in U.S. Ser. No. 14/839,273, published as US 2015/0368229, the entire contents of each of which are incorporated herein by reference. In some embodiments of the strategies, treatment modalities, methods, combinations, and compositions provided herein, the EZH2 inhibitor is a compound of the formula:

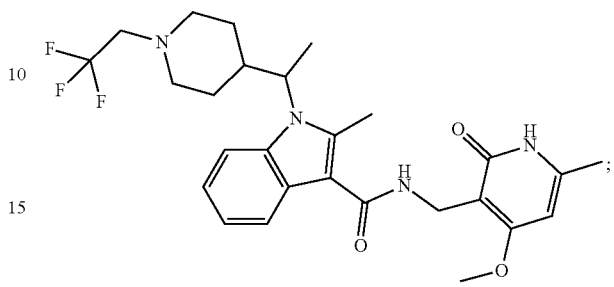

or a pharmaceutically acceptable salt thereof (see, for example US 2015/0368229, the contents of which are incorporated herein).

In some embodiments, the EZH2 inhibitor is a small molecule that is used as the compound itself, i.e., as the free base or "naked" molecule. In some embodiments, the EZH2 inhibitor is a salt thereof, e.g., a mono-HCl or tri-HCl salt, mono-HBr or tri-HBr salt of the naked molecule.

Representative compounds that are suitable for the strategies, treatment modalities, methods, combinations, and compositions provided herein include compounds listed in Table 1. In the table below, each occurrence of

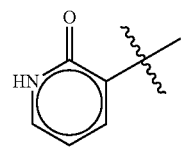

should be construed as

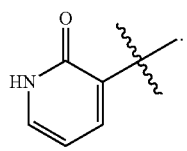

TABLE 1

| Compound Number | Structure | MS (M + 1)+ |
|---|---|---|
| 1 | 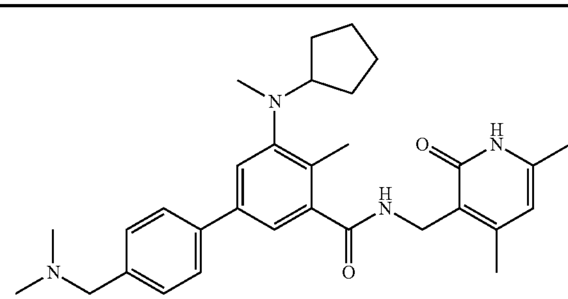 | 501.39 |

TABLE 1-continued
| Compound Number | Structure | MS (M + 1)+ |
|---|---|---|
| 2 | 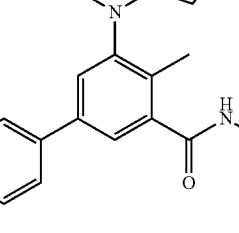 | 543.22 |
| 3 | 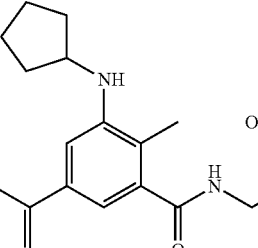 | 486.21 |
| 4 | 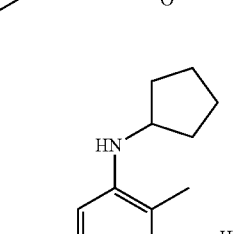 | 529.30 |
| 11 | 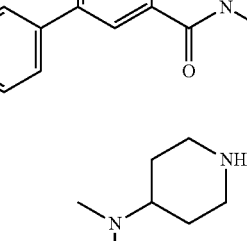 | 558.45 |
| 12 | 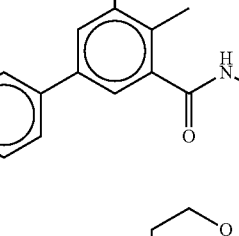 | 559.35 |

TABLE 1-continued

| Compound Number | Structure | MS (M + 1)+ |
|---|---|---|
| 13 | 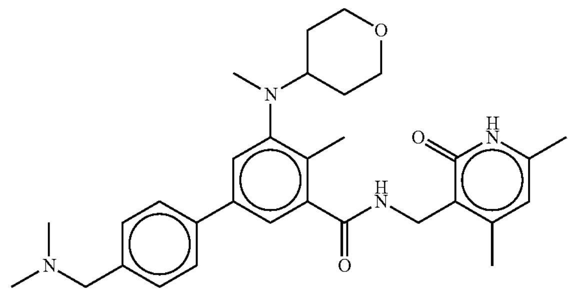 | 517.3 |
| 14 | 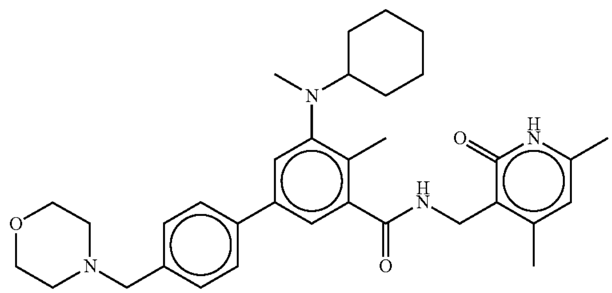 | 557.4 |
| 16 | 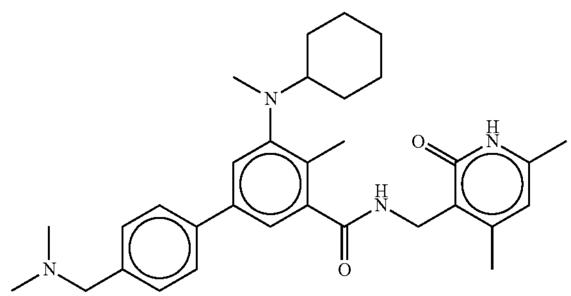 | 515.4 |
| 20 | 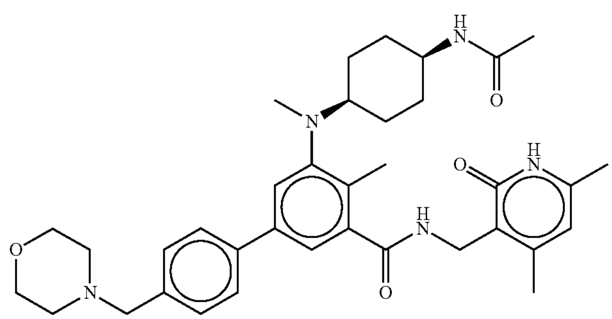 | 614.4 |
| 21 | 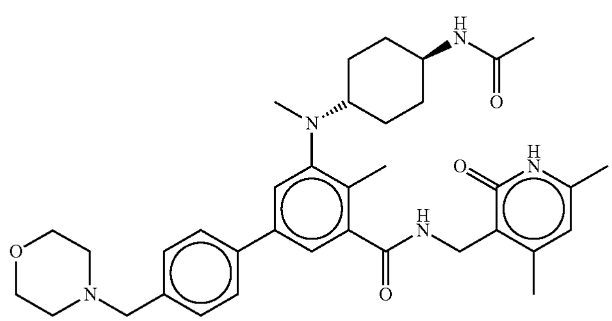 | 614.4 |

TABLE 1-continued

| Compound Number | Structure | MS (M + 1)+ |
|---|---|---|
| 27 | 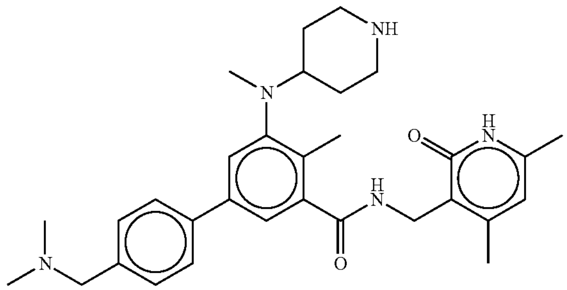 | 516.35 |
| 36 | 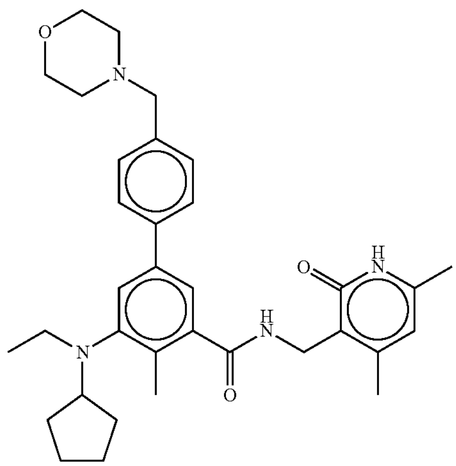 | 557.35 |
| 39 | 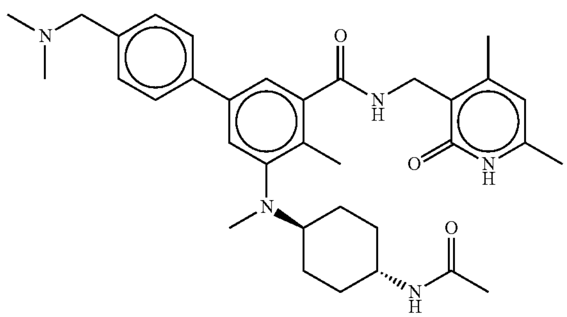 | 572.35 |
| 40 | 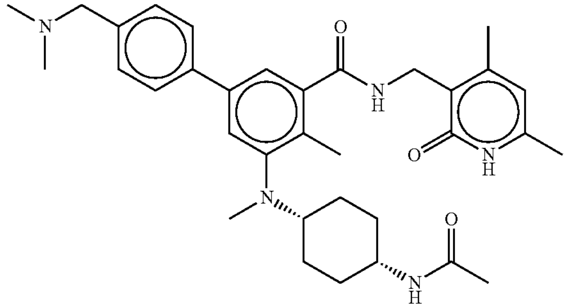 | 572.35 |

TABLE 1-continued

| Compound Number | Structure | MS (M + 1)+ |
|---|---|---|
| 42 | 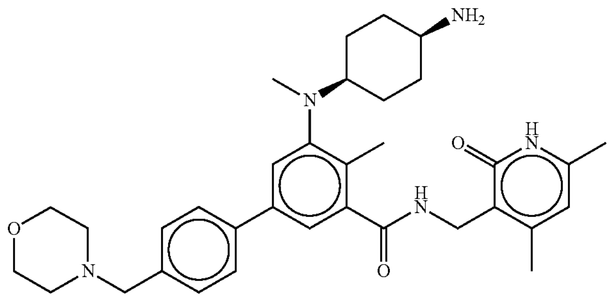 | 572.4 |
| 43 | 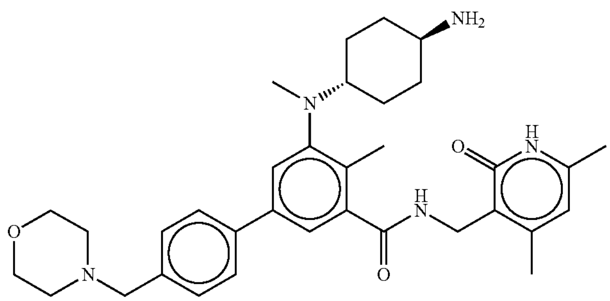 | 572.6 |
| 44 | 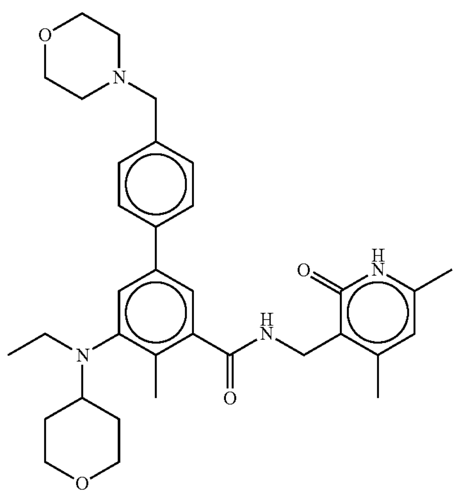 | 573.40 |
| 47 | 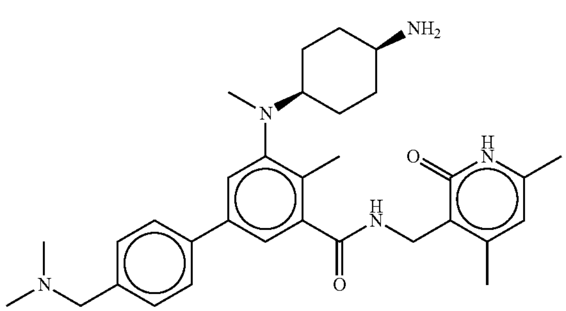 | 530.35 |

TABLE 1-continued

| Compound Number | Structure | MS (M + 1)+ |
|---|---|---|
| 59 | 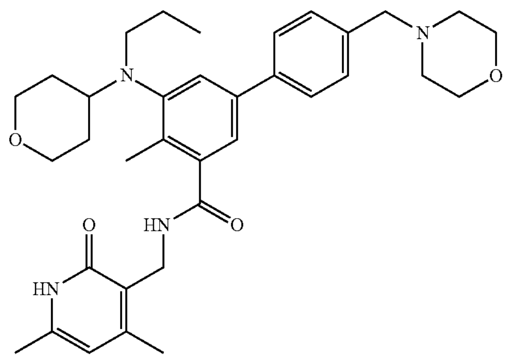 [SMILES: CCCN(c1cc(-c2ccc(CN3CCOCC3)cc2)cc(C(=O)NCc2c(C)cc(C)[nH]c2=O)c1C)C1CCOCC1] | 587.40 |
| 60 | 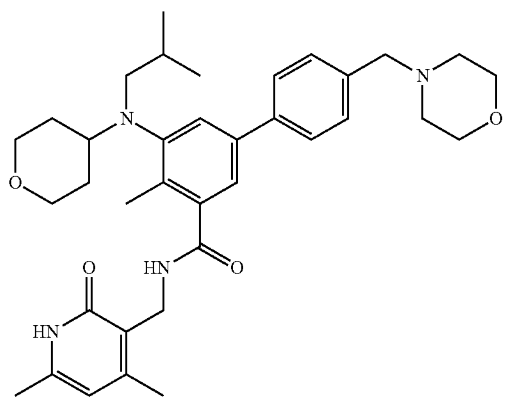 [SMILES: Cc1cc(C)c(CNC(=O)c2cc(-c3ccc(CN4CCOCC4)cc3)cc(N(CC(C)C)C3CCOCC3)c2C)c(=O)[nH]1] | 601.30 |
| 61 | 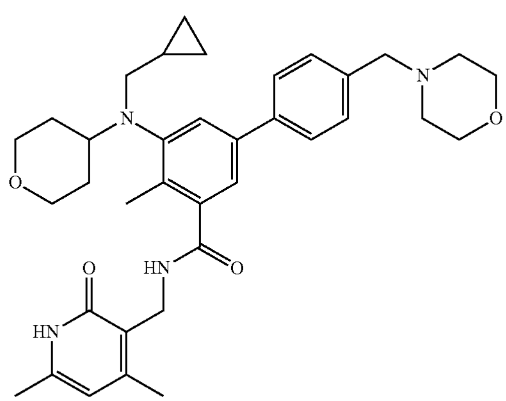 [SMILES: Cc1cc(C)c(CNC(=O)c2cc(-c3ccc(CN4CCOCC4)cc3)cc(N(CC3CC3)C3CCOCC3)c2C)c(=O)[nH]1] | 599.35 |
| 62 | 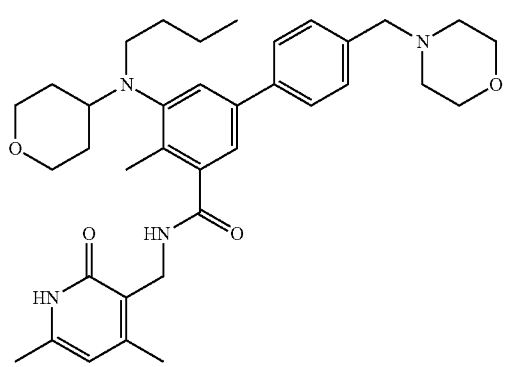 [SMILES: CCCCN(c1cc(-c2ccc(CN3CCOCC3)cc2)cc(C(=O)NCc2c(C)cc(C)[nH]c2=O)c1C)C1CCOCC1] | 601.35 |

TABLE 1-continued
| Compound Number | Structure | MS (M + 1)+ |
|---|---|---|
| 63 | 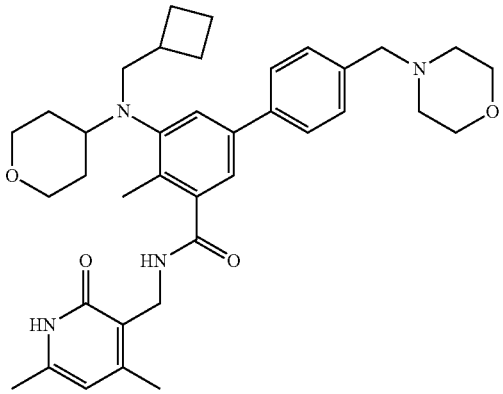 [SMILES: Cc1cc(C)c(CNC(=O)c2cc(-c3ccc(CN4CCOCC4)cc3)cc(N(CC3CCC3)C3CCOCC3)c2C)c(=O)[nH]1] | 613.35 |
| 65 | 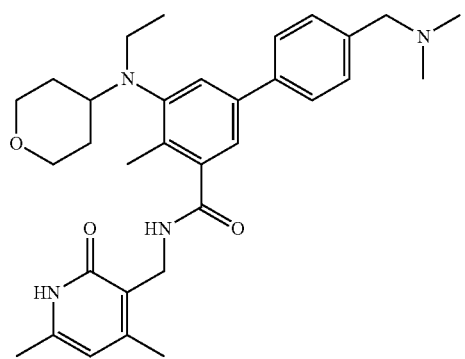 [SMILES: CCN(c1cc(-c2ccc(CN(C)C)cc2)cc(C(=O)NCc2c(C)cc(C)[nH]c2=O)c1C)C1CCOCC1] | 531.30 |
| 66 | 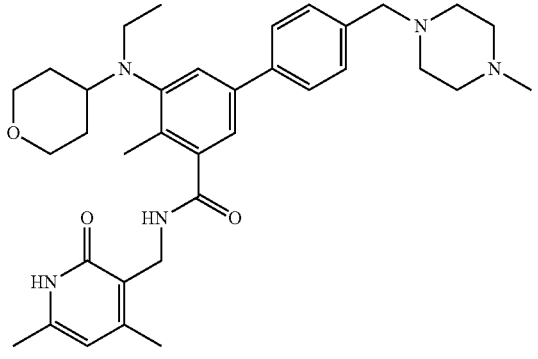 [SMILES: CCN(c1cc(-c2ccc(CN3CCN(C)CC3)cc2)cc(C(=O)NCc2c(C)cc(C)[nH]c2=O)c1C)C1CCOCC1] | 586.40 |
| 67 | 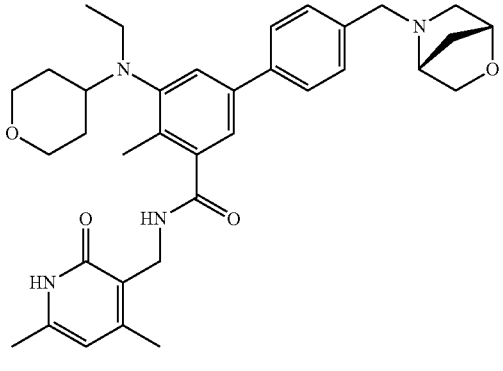 [SMILES: CCN(c1cc(-c2ccc(CN3C[C@H]4C[C@@H]3CO4)cc2)cc(C(=O)NCc2c(C)cc(C)[nH]c2=O)c1C)C1CCOCC1] | 585.25 |

TABLE 1-continued

| Compound Number | Structure | MS (M + 1)+ |
|---|---|---|
| 68 | 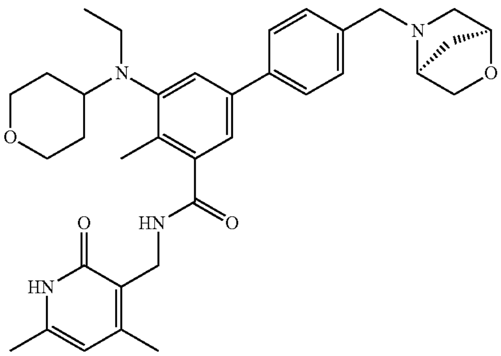 [SMILES: CCN(c1cc(-c2ccc(CN3C[C@@H]4C[C@H]3CO4)cc2)cc(C(=O)NCc2c(C)cc(C)[nH]c2=O)c1C)C1CCOCC1] | 585.35 |
| 69 | 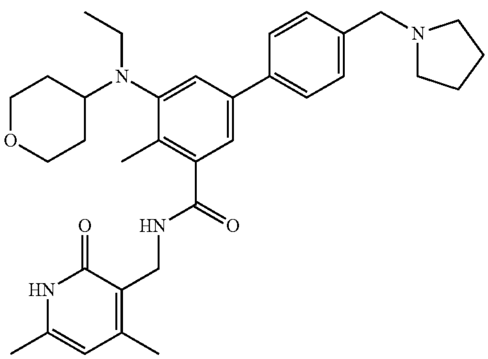 [SMILES: CCN(c1cc(-c2ccc(CN3CCCC3)cc2)cc(C(=O)NCc2c(C)cc(C)[nH]c2=O)c1C)C1CCOCC1] | 557.25 |
| 70 | 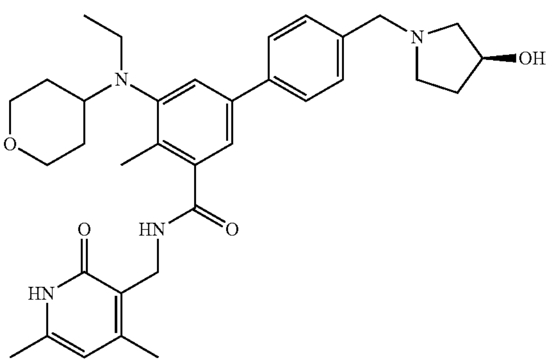 [SMILES: CCN(c1cc(-c2ccc(CN3CC[C@H](O)C3)cc2)cc(C(=O)NCc2c(C)cc(C)[nH]c2=O)c1C)C1CCOCC1] | 573.40 |
| 71 | 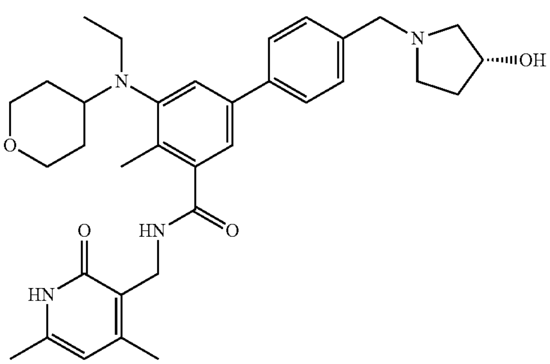 [SMILES: CCN(c1cc(-c2ccc(CN3CC[C@@H](O)C3)cc2)cc(C(=O)NCc2c(C)cc(C)[nH]c2=O)c1C)C1CCOCC1] | 573.40 |

TABLE 1-continued

| Compound Number | Structure | MS (M + 1)+ |
|---|---|---|
| 72 | 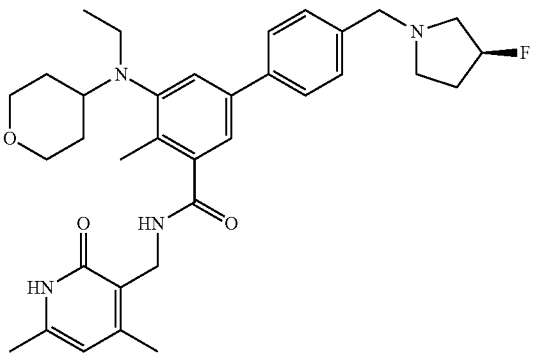 [SMILES: CCN(c1cc(-c2ccc(CN3CC[C@H](F)C3)cc2)cc(C(=O)NCc2c(C)cc(C)[nH]c2=O)c1C)C1CCOCC1] | 575.35 |
| 73 | 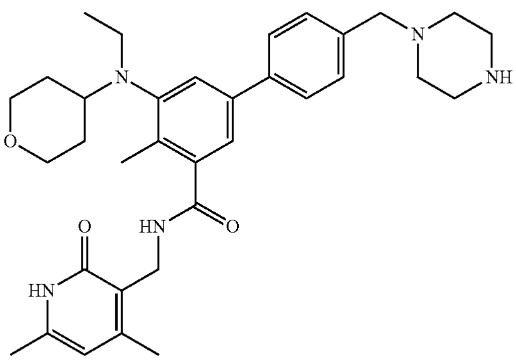 [SMILES: CCN(c1cc(-c2ccc(CN3CCNCC3)cc2)cc(C(=O)NCc2c(C)cc(C)[nH]c2=O)c1C)C1CCOCC1] | 572.10 |
| 74 | 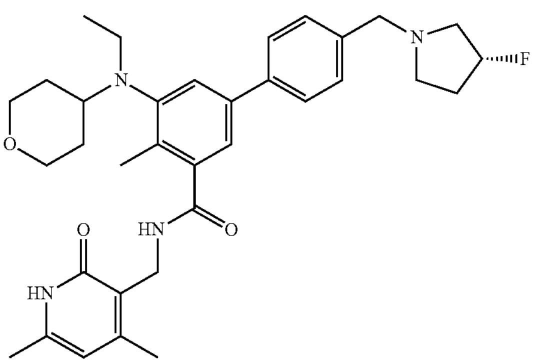 [SMILES: CCN(c1cc(-c2ccc(CN3CC[C@@H](F)C3)cc2)cc(C(=O)NCc2c(C)cc(C)[nH]c2=O)c1C)C1CCOCC1] | 575.35 |
| 75 | 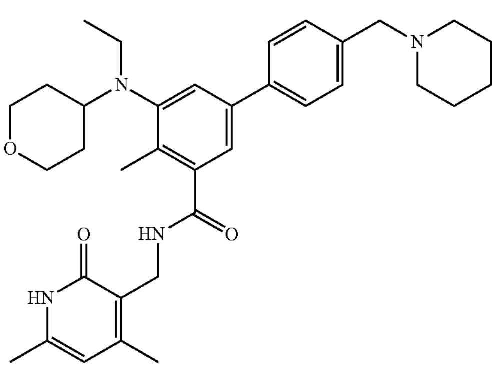 [SMILES: CCN(c1cc(-c2ccc(CN3CCCCC3)cc2)cc(C(=O)NCc2c(C)cc(C)[nH]c2=O)c1C)C1CCOCC1] | 571.25 |

TABLE 1-continued

| Compound Number | Structure | MS (M + 1)+ |
|---|---|---|
| 76 | 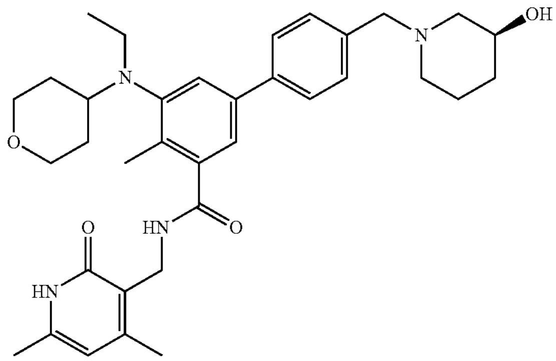 [SMILES: CCN(c1cc(-c2ccc(CN3CCC[C@H](O)C3)cc2)cc(C(=O)NCc2c(C)cc(C)[nH]c2=O)c1C)C1CCOCC1] | 587.40 |
| 77 | 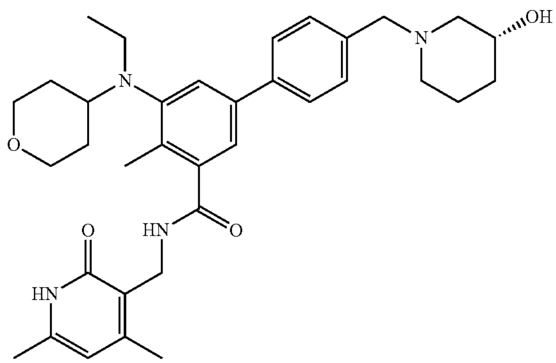 [SMILES: CCN(c1cc(-c2ccc(CN3CCC[C@@H](O)C3)cc2)cc(C(=O)NCc2c(C)cc(C)[nH]c2=O)c1C)C1CCOCC1] | 587.45 |
| 78 | 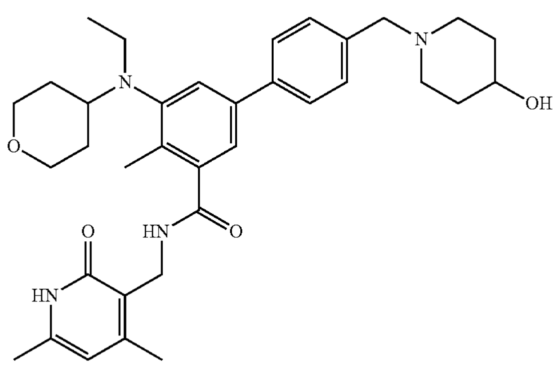 [SMILES: CCN(c1cc(-c2ccc(CN3CCC(O)CC3)cc2)cc(C(=O)NCc2c(C)cc(C)[nH]c2=O)c1C)C1CCOCC1] | 587.20 |
| 79 | 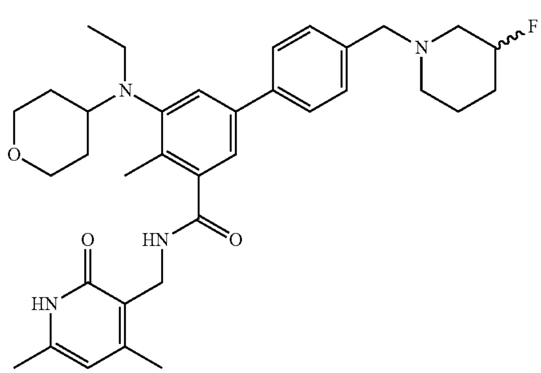 [SMILES: CCN(c1cc(-c2ccc(CN3CCCC(F)C3)cc2)cc(C(=O)NCc2c(C)cc(C)[nH]c2=O)c1C)C1CCOCC1] | 589.35 |

TABLE 1-continued

| Compound Number | Structure | MS (M + 1)+ |
|---|---|---|
| 80 | 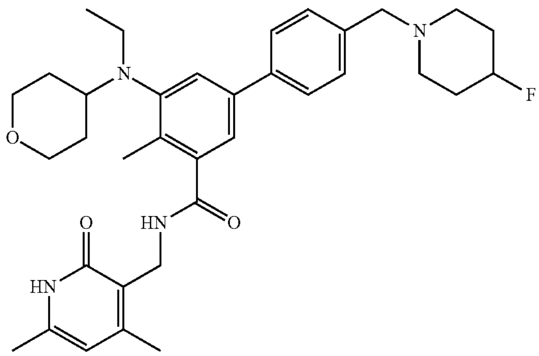 [SMILES: CCN(c1cc(-c2ccc(CN3CCC(F)CC3)cc2)cc(C(=O)NCc2c(C)cc(C)[nH]c2=O)c1C)C1CCOCC1] | 589.30 |
| 81 | 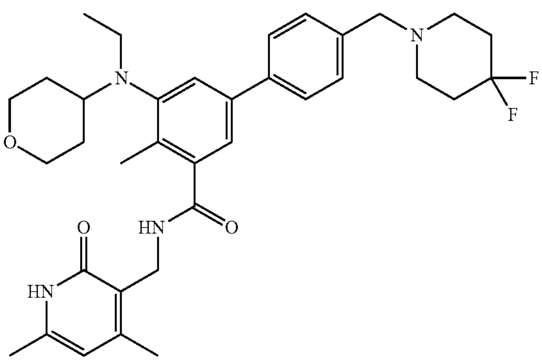 [SMILES: CCN(c1cc(-c2ccc(CN3CCC(F)(F)CC3)cc2)cc(C(=O)NCc2c(C)cc(C)[nH]c2=O)c1C)C1CCOCC1] | 607.35 |
| 82 | 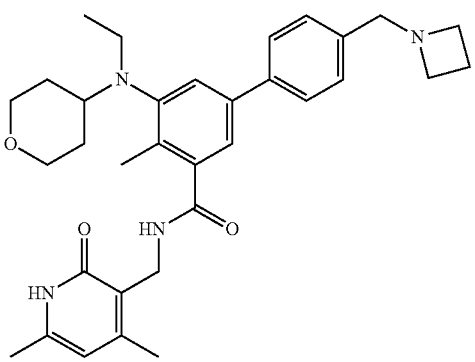 [SMILES: CCN(c1cc(-c2ccc(CN3CCC3)cc2)cc(C(=O)NCc2c(C)cc(C)[nH]c2=O)c1C)C1CCOCC1] | 543.40 |
| 83 | 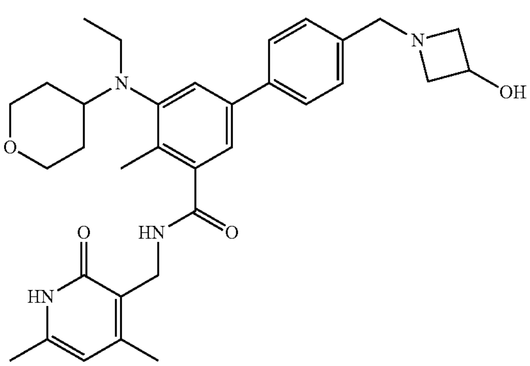 [SMILES: CCN(c1cc(-c2ccc(CN3CC(O)C3)cc2)cc(C(=O)NCc2c(C)cc(C)[nH]c2=O)c1C)C1CCOCC1] | 559.80 |

TABLE 1-continued
| Compound Number | Structure | MS (M + 1)+ |
|---|---|---|
| 84 | 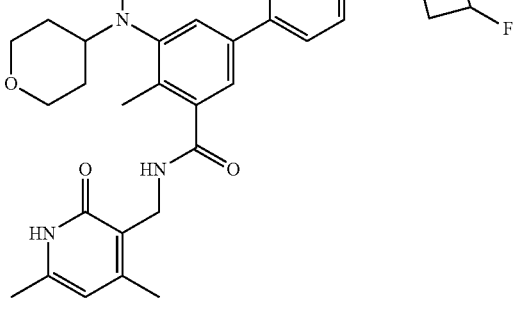 | 561.25 |
| 85 | 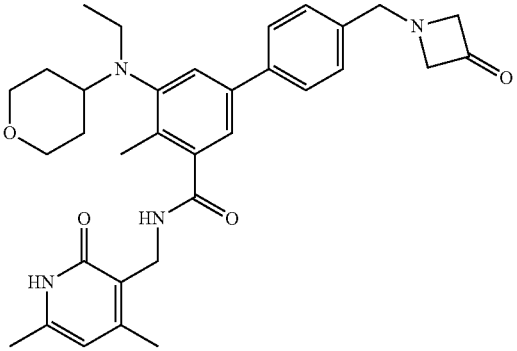 [SMILES: CCN(c1cc(-c2ccc(CN3CC(=O)C3)cc2)cc(C(=O)NCc2c(C)cc(C)[nH]c2=O)c1C)C1CCOCC1] | |
| 86 | 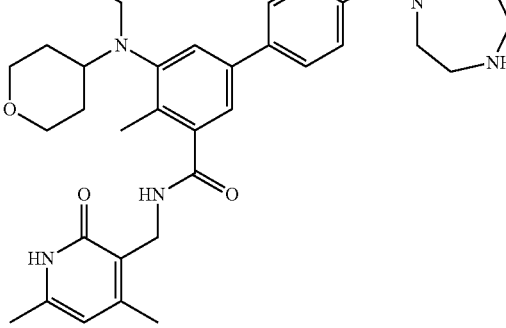 | 585.37 |
| 87 | 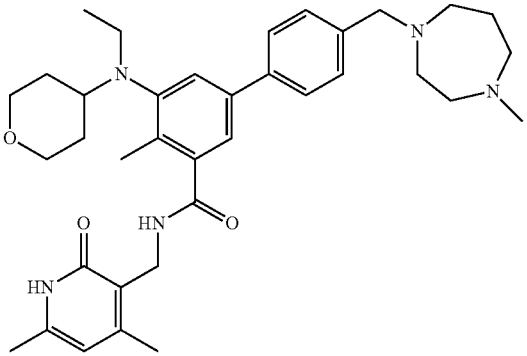 [SMILES: CCN(c1cc(-c2ccc(CN3CCCN(C)CC3)cc2)cc(C(=O)NCc2c(C)cc(C)[nH]c2=O)c1C)C1CCOCC1] | 600.30 |

TABLE 1-continued

| Compound Number | Structure | MS (M + 1)+ |
|---|---|---|
| 88 | 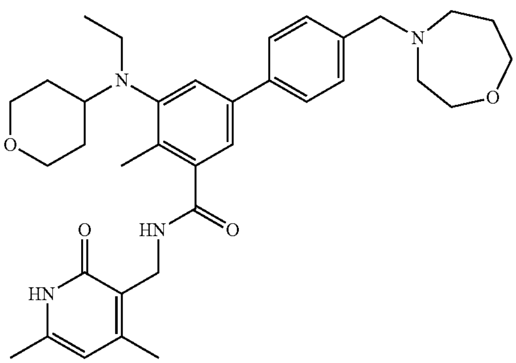 [SMILES: CCN(c1cc(-c2ccc(CN3CCCOCC3)cc2)cc(C(=O)NCc2c(C)cc(C)[nH]c2=O)c1C)C1CCOCC1] | 587.40 |
| 89 | 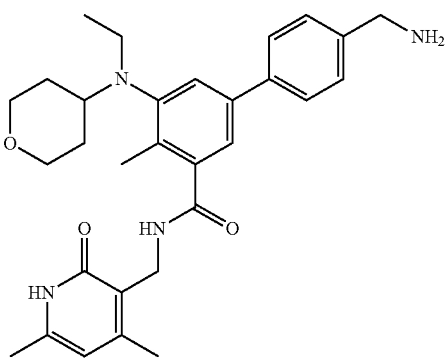 [SMILES: CCN(c1cc(-c2ccc(CN)cc2)cc(C(=O)NCc2c(C)cc(C)[nH]c2=O)c1C)C1CCOCC1] | 503.40 |
| 90 | 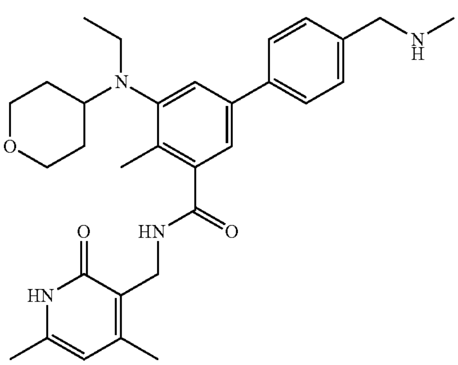 [SMILES: CCN(c1cc(-c2ccc(CNC)cc2)cc(C(=O)NCc2c(C)cc(C)[nH]c2=O)c1C)C1CCOCC1] | 517.30 |
| 91 | 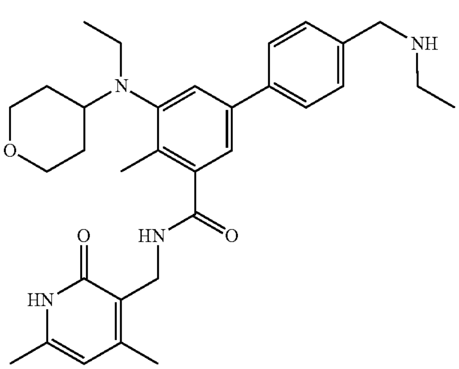 [SMILES: CCNCc1ccc(-c2cc(C(=O)NCc3c(C)cc(C)[nH]c3=O)c(C)c(N(CC)C3CCOCC3)c2)cc1] | 531.35 |

TABLE 1-continued

| Compound Number | Structure | MS (M + 1)+ |
|---|---|---|
| 92 | 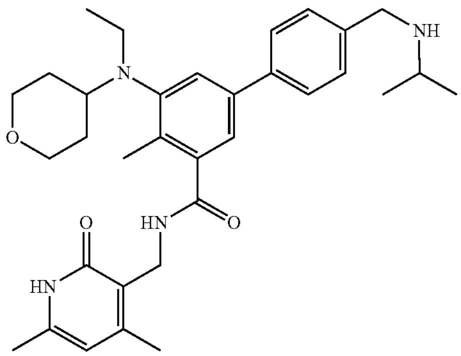 [SMILES: CCN(c1cc(-c2ccc(CNC(C)C)cc2)cc(C(=O)NCc2c(C)cc(C)[nH]c2=O)c1C)C1CCOCC1] | 545.40 |
| 93 | 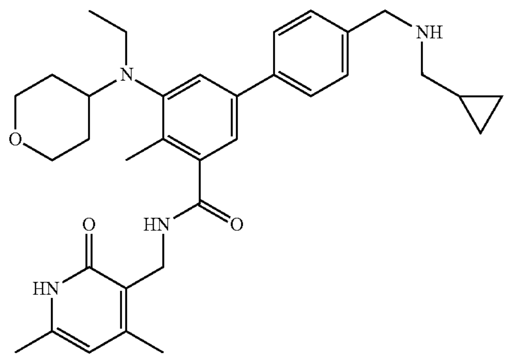 [SMILES: CCN(c1cc(-c2ccc(CNCC3CC3)cc2)cc(C(=O)NCc2c(C)cc(C)[nH]c2=O)c1C)C1CCOCC1] | 557.35 |
| 94 | 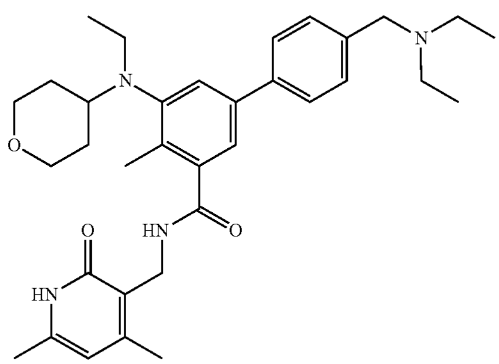 [SMILES: CCN(CC)Cc1ccc(-c2cc(C(=O)NCc3c(C)cc(C)[nH]c3=O)c(C)c(N(CC)C3CCOCC3)c2)cc1] | 559.20 |
| 95 | 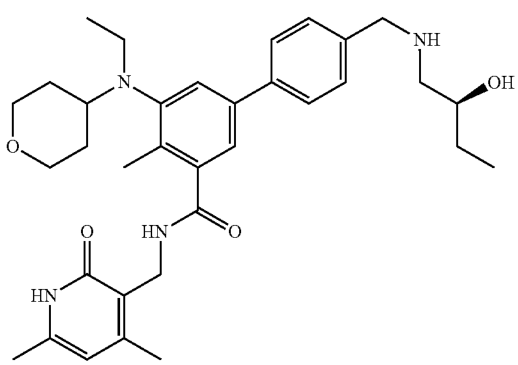 [SMILES: CC[C@H](O)CNCc1ccc(-c2cc(C(=O)NCc3c(C)cc(C)[nH]c3=O)c(C)c(N(CC)C3CCOCC3)c2)cc1] | 599.35 (M +Na) |

TABLE 1-continued

| Compound Number | Structure | MS (M + 1)+ |
|---|---|---|
| 96 | 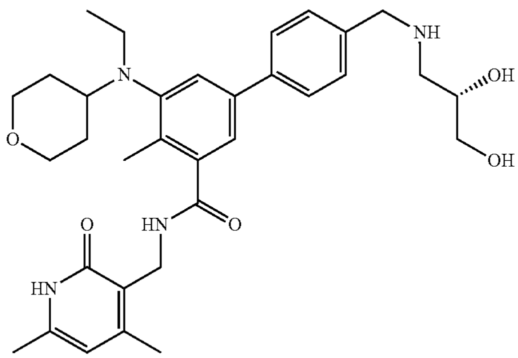 [SMILES: CCN(c1cc(-c2ccc(CNC[C@H](O)CO)cc2)cc(C(=O)NCc2c(C)cc(C)[nH]c2=O)c1C)C1CCOCC1] | 577.25 |
| 97 | 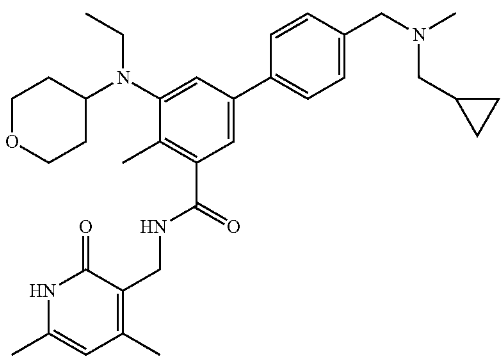 [SMILES: CCN(c1cc(-c2ccc(CN(C)CC3CC3)cc2)cc(C(=O)NCc2c(C)cc(C)[nH]c2=O)c1C)C1CCOCC1] | 571.40 |
| 98 | 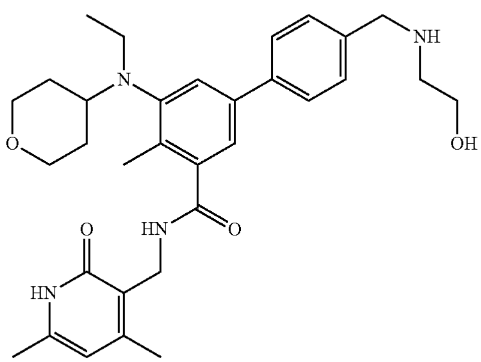 [SMILES: CCN(c1cc(-c2ccc(CNCCO)cc2)cc(C(=O)NCc2c(C)cc(C)[nH]c2=O)c1C)C1CCOCC1] | 547.35 |
| 99 | 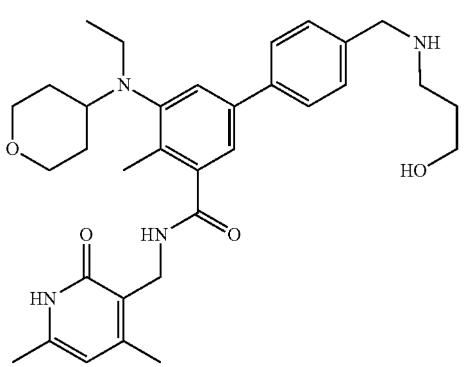 [SMILES: CCN(c1cc(-c2ccc(CNCCCO)cc2)cc(C(=O)NCc2c(C)cc(C)[nH]c2=O)c1C)C1CCOCC1] | 561.30 |

TABLE 1-continued

| Compound Number | Structure | MS (M + 1)+ |
|---|---|---|
| 100 | 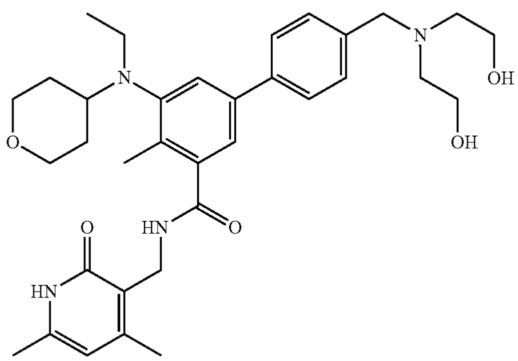 [SMILES: CCN(c1cc(-c2ccc(CN(CCO)CCO)cc2)cc(C(=O)NCc2c(C)cc(C)[nH]c2=O)c1C)C1CCOCC1] | 591.25 |
| 101 | 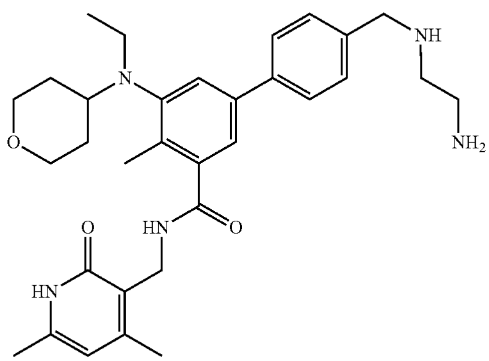 [SMILES: CCN(c1cc(-c2ccc(CNCCN)cc2)cc(C(=O)NCc2c(C)cc(C)[nH]c2=O)c1C)C1CCOCC1] | 546.35 |
| 102 | 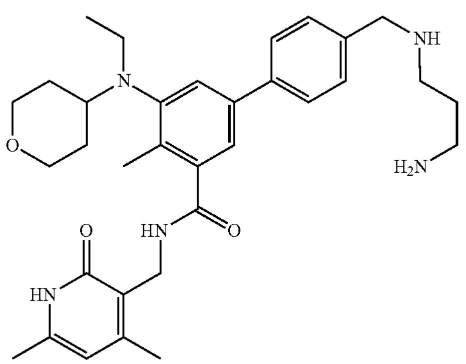 | 560.20 |
| 103 | 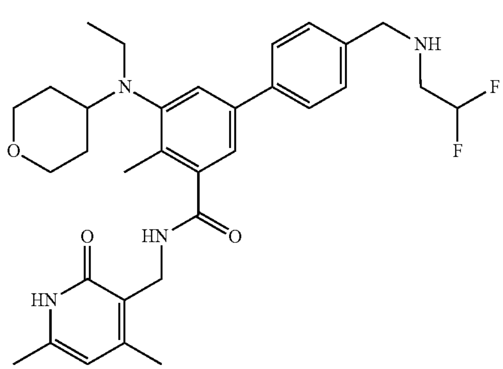 [SMILES: CCN(c1cc(-c2ccc(CNCC(F)F)cc2)cc(C(=O)NCc2c(C)cc(C)[nH]c2=O)c1C)C1CCOCC1] | 567.30 |

TABLE 1-continued

| Compound Number | Structure | MS (M + 1)+ |
|---|---|---|
| 104 | 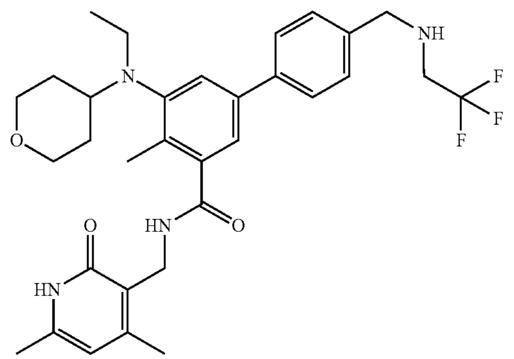 [SMILES: CCN(c1cc(-c2ccc(CNCC(F)(F)F)cc2)cc(C(=O)NCc2c(C)cc(C)[nH]c2=O)c1C)C1CCOCC1] | 585.25 |
| 105 | 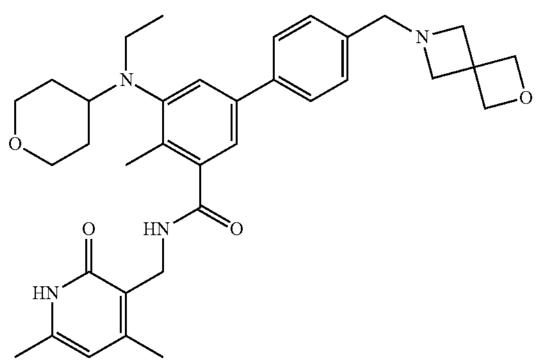 [SMILES: CCN(c1cc(-c2ccc(CN3CC4(COC4)C3)cc2)cc(C(=O)NCc2c(C)cc(C)[nH]c2=O)c1C)C1CCOCC1] | 585.40 |
| 107 | 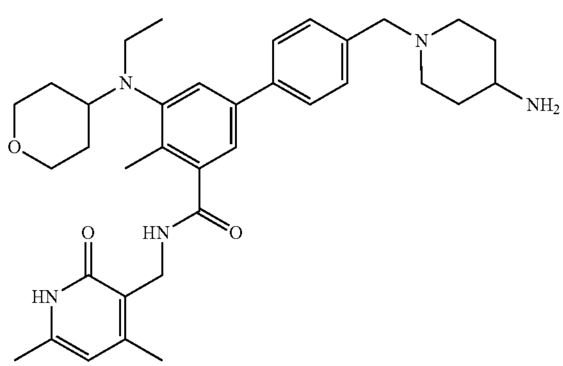 [SMILES: CCN(c1cc(-c2ccc(CN3CCC(N)CC3)cc2)cc(C(=O)NCc2c(C)cc(C)[nH]c2=O)c1C)C1CCOCC1] | |
| 108 | 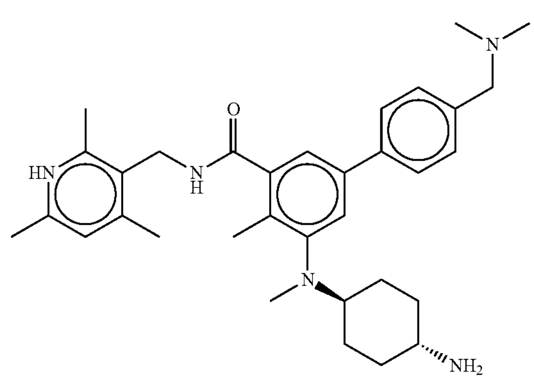 | 530.35 |

TABLE 1-continued

| Compound Number | Structure | MS (M + 1)+ |
|---|---|---|
| 114 | 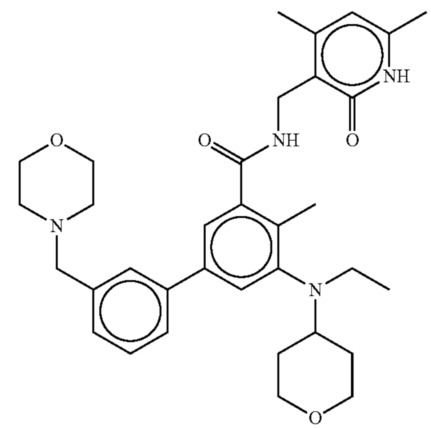 | 573.25 |
| 115 | 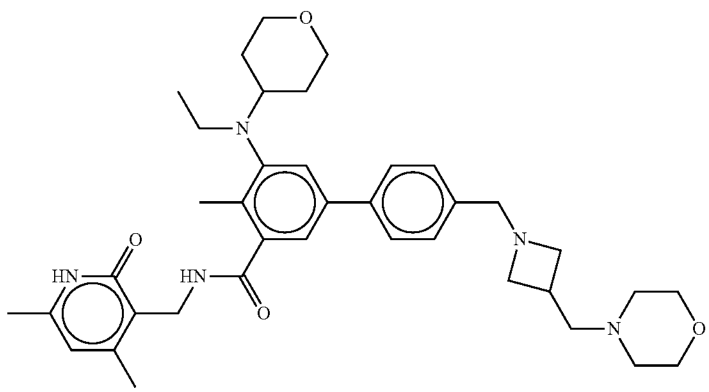 | 642.45 |
| 116 | 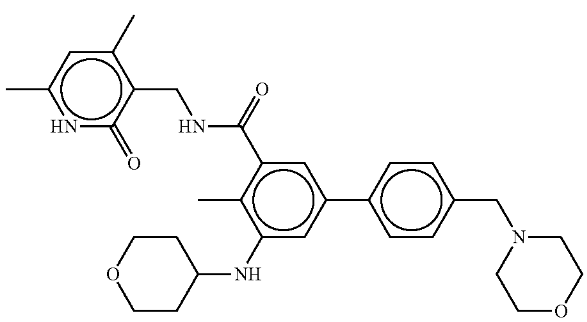 | 545.15 |
| 117 | 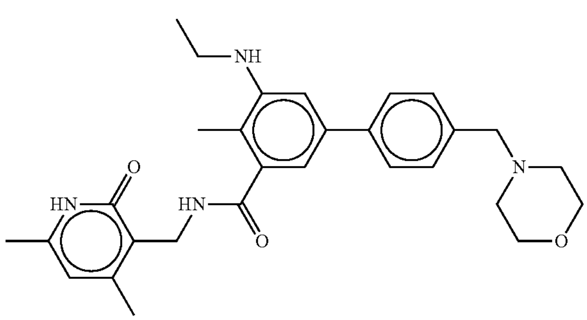 | 489.20 |

TABLE 1-continued

| Compound Number | Structure | MS (M + 1)+ |
|---|---|---|
| 119 | 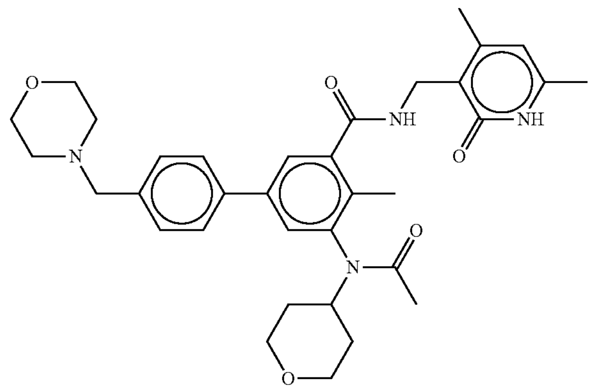 | 609.35 |
| 122 | 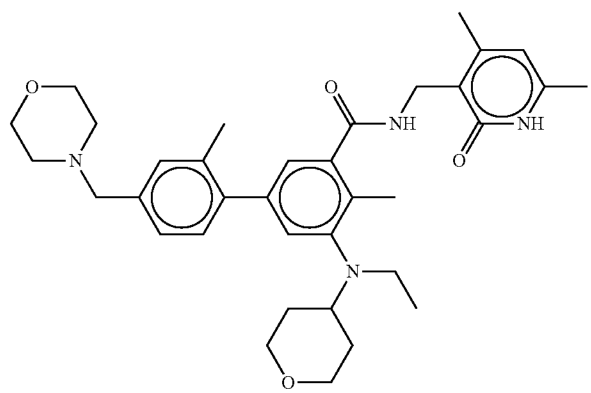 | 587.55 |
| 124 | 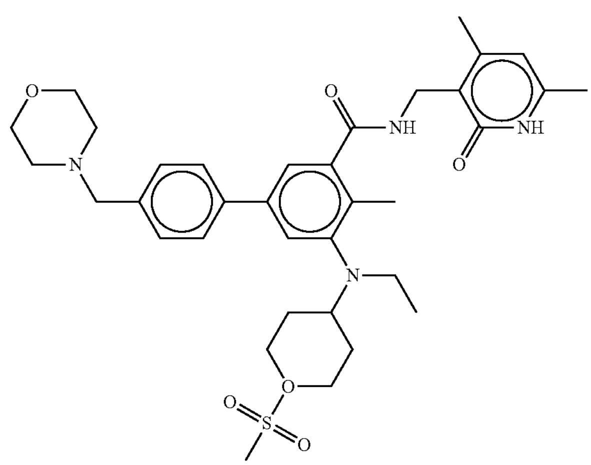 | 650.85 |

TABLE 1-continued

| Compound Number | Structure | MS (M + 1)+ |
|---|---|---|
| 125 | 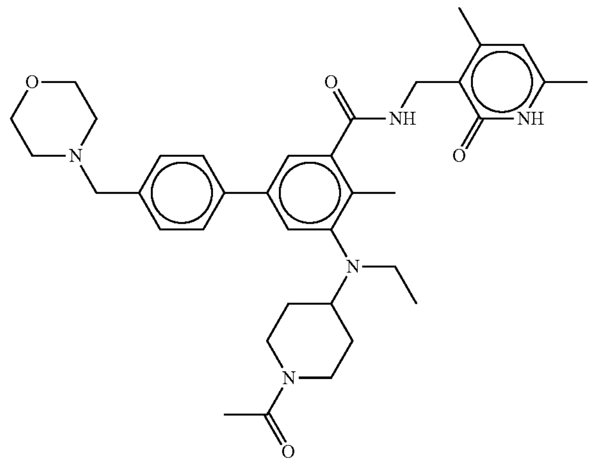 | 614.75 |
| 126 | 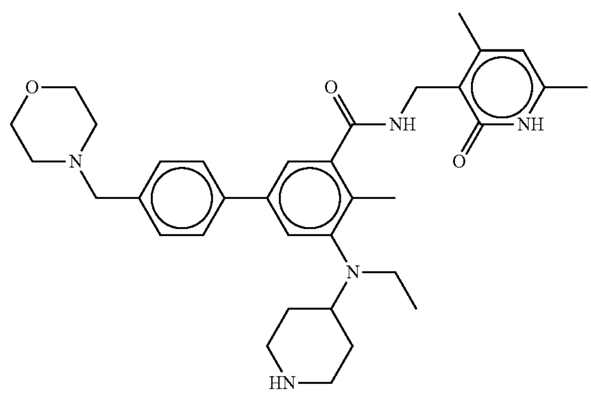 | 572.35 |
| 127 | 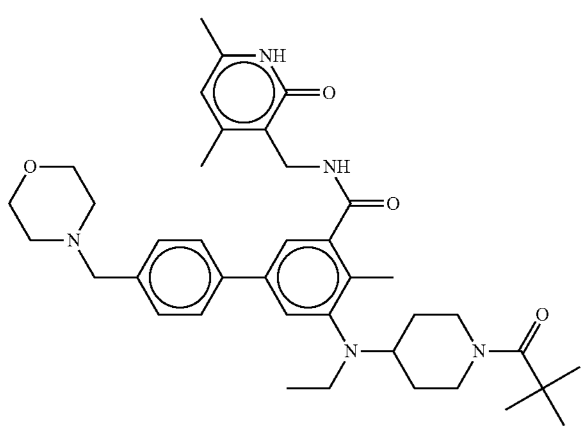 | 656.65 |

TABLE 1-continued

| Compound Number | Structure | MS (M + 1)+ |
|---|---|---|
| 128 | 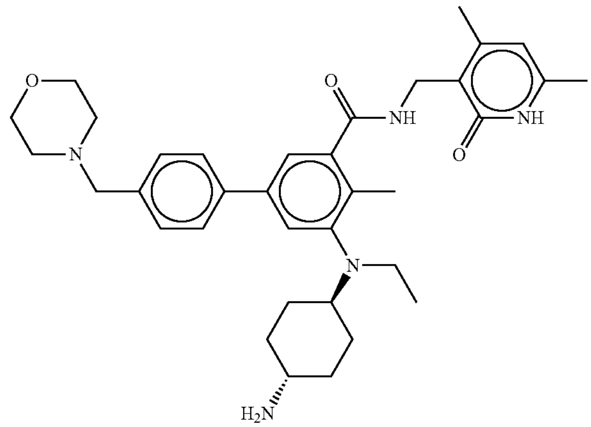 | 586.45 |
| 129 | 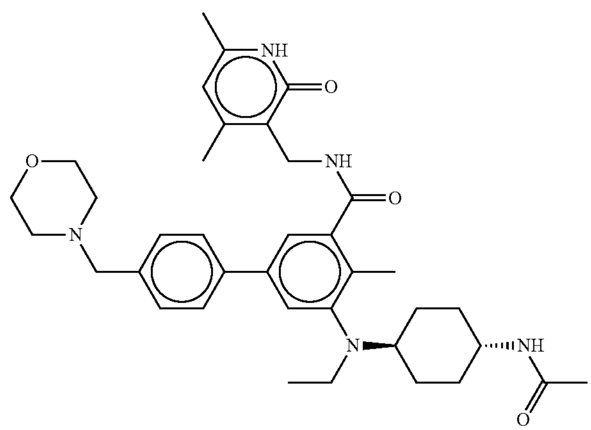 | 628.35 |
| 130 | 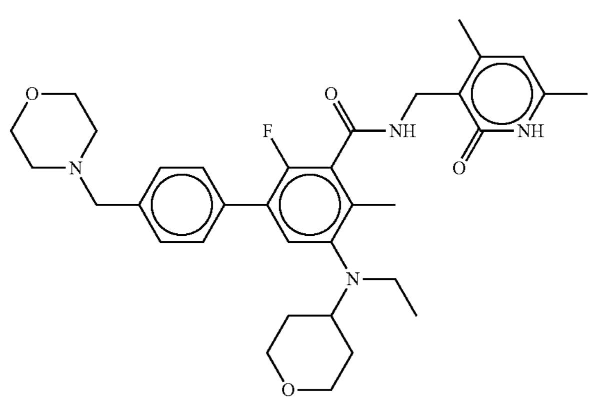 | 591.2 |

TABLE 1-continued

| Compound Number | Structure | MS (M + 1)+ |
|---|---|---|
| 131 | 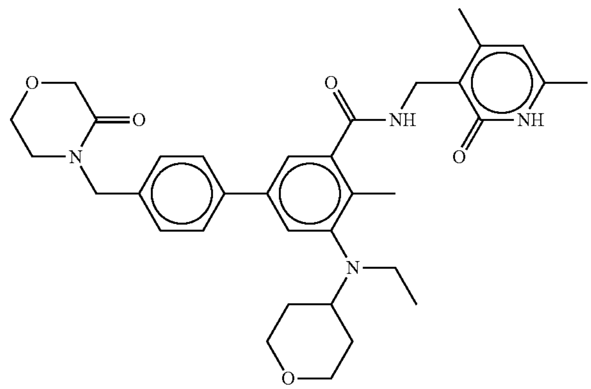 | 587.35 |
| 132 | 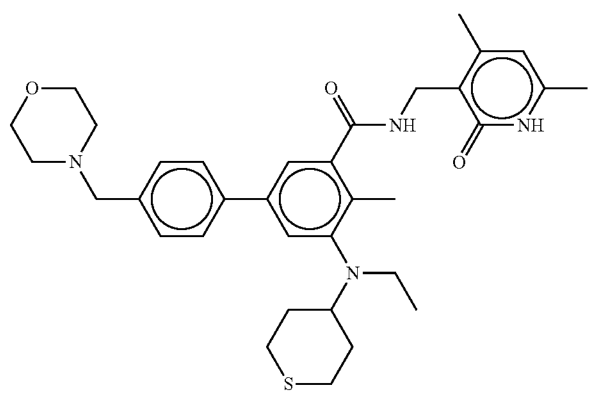 | 589.25 |
| 133 | 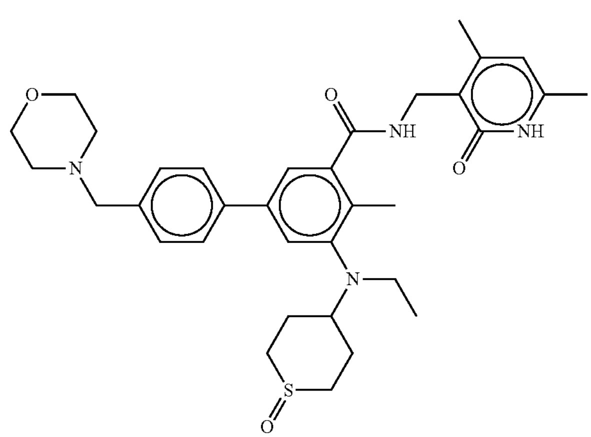 | 605.25 |

TABLE 1-continued

| Compound Number | Structure | MS (M + 1)+ |
|---|---|---|
| 135 | 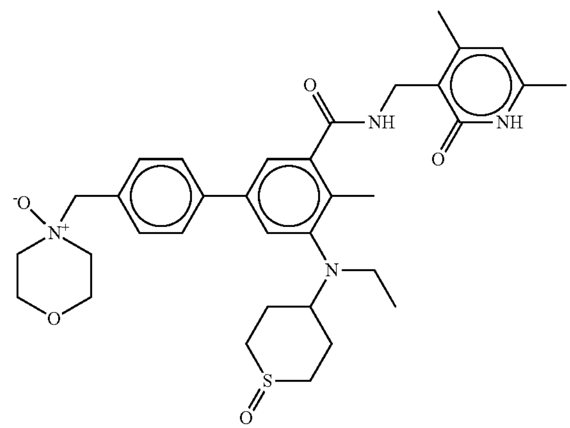 | 621.40 |
| 136 | 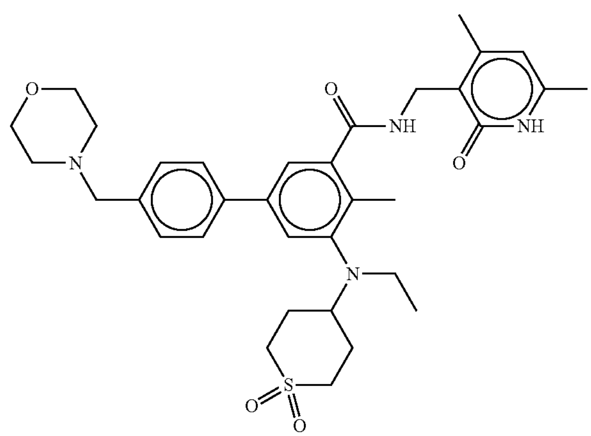 | 621.45 |
| 137 | 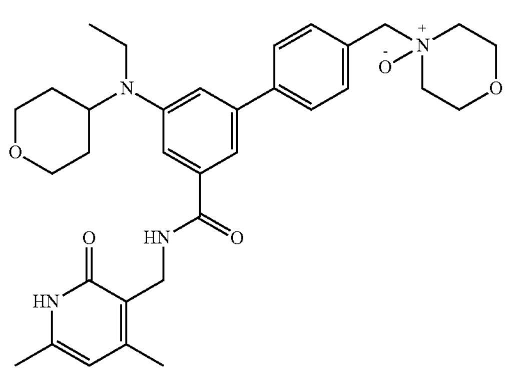 | 589.35 |

TABLE 1-continued

| Compound Number | Structure | MS (M + 1)+ |
|---|---|---|
| 138 | 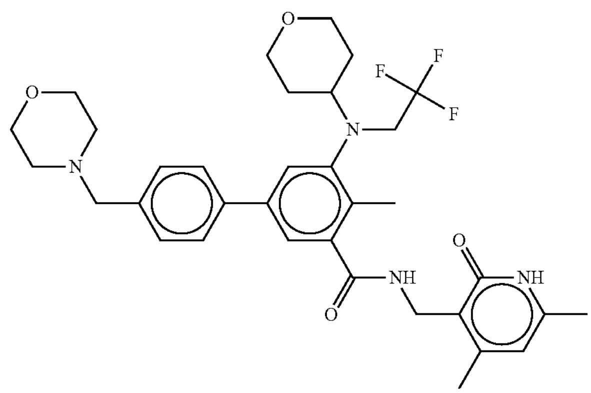 | 627.5 |
| 141 | 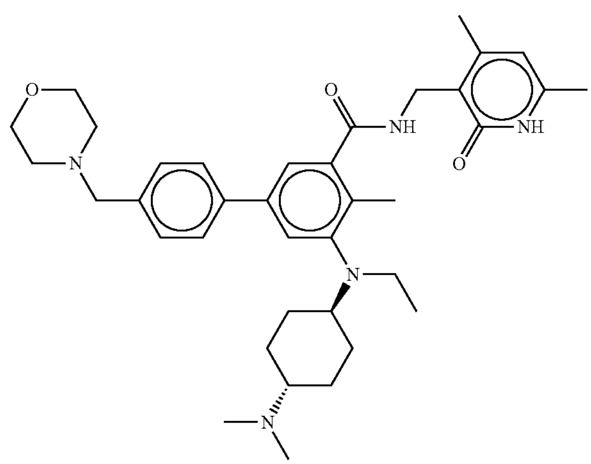 | 614.65 |
| 142 | 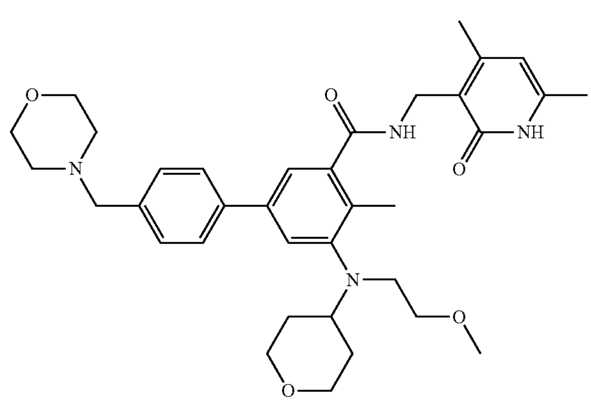 [SMILES: COCCN(c1cc(-c2ccc(CN3CCOCC3)cc2)cc(C(=O)NCc2c(C)cc(C)[nH]c2=O)c1C)C1CCOCC1] | 603.45 |

TABLE 1-continued

| Compound Number | Structure | MS (M + 1)+ |
|---|---|---|
| 143 | 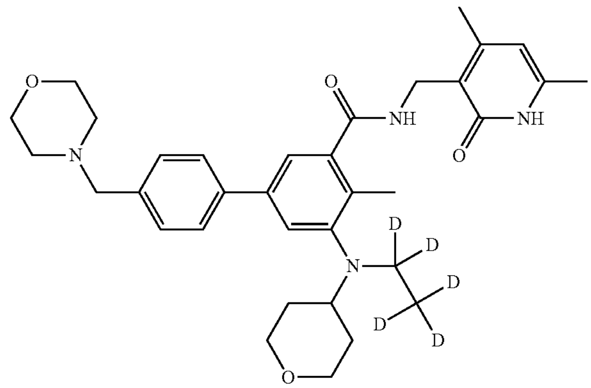 [SMILES: [2H]C([2H])([2H])C([2H])([2H])N(c1cc(-c2ccc(CN3CCOCC3)cc2)cc(C(=O)NCc2c(C)cc(C)[nH]c2=O)c1C)C1CCOCC1] | 578.35 |
| 144 | 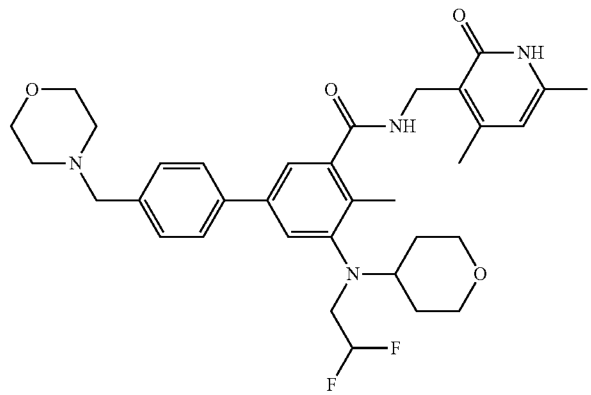 [SMILES: Cc1cc(C)c(CNC(=O)c2cc(-c3ccc(CN4CCOCC4)cc3)cc(N(CC(F)F)C3CCOCC3)c2C)c(=O)[nH]1] | 609.15 |
| 146 | 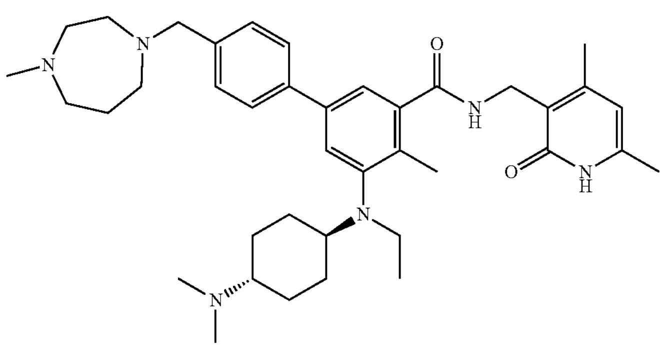 | 641.50 |
| 178 | 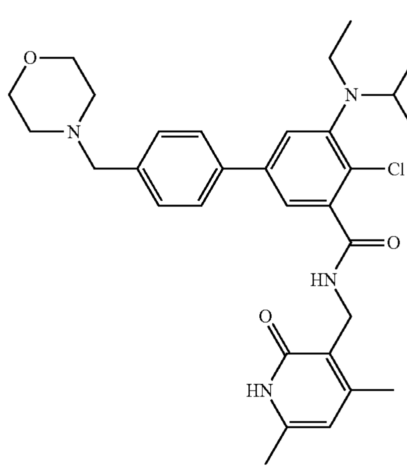 | 593.60 |

As used herein, "alkyl", "$C_1$, $C_2$, $C_3$, $C_4$, $C_5$ or $C_6$ alkyl" or "$C_1$-$C_6$ alkyl" is intended to include $C_1$, $C_2$, $C_3$, $C_4$, $C_5$ or $C_6$ straight chain (linear) saturated aliphatic hydrocarbon groups and $C_3$, $C_4$, $C_5$ or $C_6$ branched saturated aliphatic hydrocarbon groups. For example, $C_1$-$C_6$ alkyl is intended to include $C_1$, $C_2$, $C_3$, $C_4$, $C_5$ and $C_6$ alkyl groups. Examples of alkyl include, moieties having from one to six carbon atoms, such as, but not limited to, methyl, ethyl, n-propyl, i-propyl, n-butyl, s-butyl, t-butyl, n-pentyl, s-pentyl or n-hexyl.

In certain embodiments, a straight chain or branched alkyl has six or fewer carbon atoms (e.g., $C_1$-$C_6$ for straight chain, $C_3$-$C_6$ for branched chain), and in some embodiments, a straight chain or branched alkyl has four or fewer carbon atoms.

As used herein, the term "cycloalkyl" refers to a saturated or unsaturated nonaromatic hydrocarbon mono- or multi-ring (e.g., fused, bridged, or spiro rings) system having 3 to 30 carbon atoms (e.g., $C_3$-$C_{10}$). Examples of cycloalkyl include, but are not limited to, cyclopropyl, cyclobutyl, cyclopentyl, cyclohexyl, cycloheptyl, cyclooctyl, cyclopentenyl, cyclohexenyl, cycloheptenyl, and adamantyl. The term "heterocycloalkyl" refers to a saturated or unsaturated nonaromatic 3-8 membered monocyclic, 7-12 membered bicyclic (fused, bridged, or spiro rings), or 11-14 membered tricyclic ring system (fused, bridged, or spiro rings) having one or more heteroatoms (such as O, N, S, or Se), unless specified otherwise. Examples of heterocycloalkyl groups include, but are not limited to, piperidinyl, piperazinyl, pyrrolidinyl, dioxanyl, tetrahydrofuranyl, isoindolinyl, indolinyl, imidazolidinyl, pyrazolidinyl, oxazolidinyl, isoxazolidinyl, triazolidinyl, tetrahyrofuranyl, oxiranyl, azetidinyl, oxetanyl, thietanyl, 1,2,3,6-tetrahydropyridinyl, tetrahydropyranyl, dihydropyranyl, pyranyl, morpholinyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, 1,4-dioxa-8-azaspiro[4.5]decanyl and the like.

The term "optionally substituted alkyl" refers to unsubstituted alkyl or alkyl having designated substituents replacing one or more hydrogen atoms on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

An "arylalkyl" or an "aralkyl" moiety is an alkyl substituted with an aryl (e.g., phenylmethyl (benzyl)). An "alkylaryl" moiety is an aryl substituted with an alkyl (e.g., methylphenyl).

As used herein, "alkyl linker" is intended to include $C_1$, $C_2$, $C_3$, $C_4$, $C_5$ or $C_6$ straight chain (linear) saturated divalent aliphatic hydrocarbon groups and $C_3$, $C_4$, $C_5$ or $C_6$ branched saturated aliphatic hydrocarbon groups. For example, $C_1$-$C_6$ alkyl linker is intended to include $C_1$, $C_2$, $C_3$, $C_4$, $C_5$ and $C_6$ alkyl linker groups. Examples of alkyl linker include, moieties having from one to six carbon atoms, such as, but not limited to, methyl (—$CH_2$—), ethyl (—$CH_2CH_2$—), n-propyl (—$CH_2CH_2CH_2$—), i-propyl (—$CHCH_3CH_2$—), n-butyl (—$CH_2CH_2CH_2CH_2$—), s-butyl (—$CHCH_3CH_2CH_2$—), i-butyl (—$C(CH_3)_2CH_2$—), n-pentyl (—$CH_2CH_2CH_2CH_2CH_2$—), s-pentyl (—$CHCH_3CH_2CH_2CH_2$—) or n-hexyl (—$CH_2CH_2CH_2CH_2CH_2CH_2$—).

"Alkenyl" includes unsaturated aliphatic groups analogous in length and possible substitution to the alkyls described above, but that contain at least one double bond. For example, the term "alkenyl" includes straight chain alkenyl groups (e.g., ethenyl, propenyl, butenyl, pentenyl, hexenyl, heptenyl, octenyl, nonenyl, decenyl), and branched alkenyl groups. In certain embodiments, a straight chain or branched alkenyl group has six or fewer carbon atoms in its backbone (e.g., $C_2$-$C_6$ for straight chain, $C_3$-$C_6$ for branched chain). The term "$C_2$-$C_6$" includes alkenyl groups containing two to six carbon atoms. The term "$C_3$-$C_6$" includes alkenyl groups containing three to six carbon atoms.

The term "optionally substituted alkenyl" refers to unsubstituted alkenyl or alkenyl having designated substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, heterocyclyl, alkylaryl, or an aromatic or heteroaromatic moiety.

"Alkynyl" includes unsaturated aliphatic groups analogous in length and possible substitution to the alkyls described above, but which contain at least one triple bond. For example, "alkynyl" includes straight chain alkynyl groups (e.g., ethynyl, propynyl, butynyl, pentynyl, hexynyl, heptynyl, octynyl, nonynyl, decynyl), and branched alkynyl groups. In certain embodiments, a straight chain or branched alkynyl group has six or fewer carbon atoms in its backbone (e.g., $C_2$-$C_6$ for straight chain, $C_3$-$C_6$ for branched chain). The term "$C_2$-$C_6$" includes alkynyl groups containing two to six carbon atoms. The term "$C_3$-$C_6$" includes alkynyl groups containing three to six carbon atoms.

The term "optionally substituted alkynyl" refers to unsubstituted alkynyl or alkynyl having designated substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Other optionally substituted moieties (such as optionally substituted cycloalkyl, heterocycloalkyl, aryl, or heteroaryl) include both the unsubstituted moieties and the moieties having one or more of the designated substituents. For example, substituted heterocycloalkyl includes those substituted with one or more alkyl groups, such as 2,2,6,6-tetramethyl-piperidinyl and 2,2,6,6-tetramethyl-1,2,3,6-tetrahydropyridinyl.

"Aryl" includes groups with aromaticity, including "conjugated," or multicyclic systems with at least one aromatic ring and do not contain any heteroatom in the ring structure. Examples include phenyl, benzyl, 1,2,3,4-tetrahydronaphthalenyl, etc.

"Heteroaryl" groups are aryl groups, as defined above, except having from one to four heteroatoms in the ring structure, and may also be referred to as "aryl heterocycles" or "heteroaromatics." As used herein, the term "heteroaryl" is intended to include a stable 5-, 6-, or 7-membered monocyclic or 7-, 8-, 9-, 10-, 11- or 12-membered bicyclic aromatic heterocyclic ring which consists of carbon atoms and one or more heteroatoms, e.g., 1 or 1-2 or 1-3 or 1-4 or 1-5 or 1-6 heteroatoms, or e.g., 1, 2, 3, 4, 5, or 6 heteroatoms, independently selected from the group consisting of nitrogen, oxygen and sulfur. The nitrogen atom may be substituted or unsubstituted (i.e., N or NR wherein R is H or other substituents, as defined). The nitrogen and sulfur heteroatoms may optionally be oxidized (i.e., N→O and $S(O)_p$, where p=1 or 2). It is to be noted that total number of S and O atoms in the aromatic heterocycle is not more than 1.

Examples of heteroaryl groups include pyrrole, furan, thiophene, thiazole, isothiazole, imidazole, triazole, tetrazole, pyrazole, oxazole, isoxazole, pyridine, pyrazine, pyridazine, pyrimidine, and the like.

Furthermore, the terms "aryl" and "heteroaryl" include multicyclic aryl and heteroaryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, naphthrydine, indole, benzofuran, purine, benzofuran, deazapurine, indolizine.

In the case of multicyclic aromatic rings, only one of the rings needs to be aromatic (e.g., 2,3-dihydroindole), although all of the rings may be aromatic (e.g., quinoline). The second ring can also be fused or bridged.

The cycloalkyl, heterocycloalkyl, aryl, or heteroaryl ring can be substituted at one or more ring positions (e.g., the ring-forming carbon or heteroatom such as N) with such substituents as described above, for example, alkyl, alkenyl, alkynyl, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl and heteroaryl groups can also be fused or bridged with alicyclic or heterocyclic rings, which are not aromatic so as to form a multicyclic system (e.g., tetralin, methylenedioxyphenyl).

As used herein, "carbocycle" or "carbocyclic ring" is intended to include any stable monocyclic, bicyclic or tricyclic ring having the specified number of carbons, any of which may be saturated, unsaturated, or aromatic. Carbocycle includes cycloalkyl and aryl. For example, a $C_3$-$C_{14}$ carbocycle is intended to include a monocyclic, bicyclic or tricyclic ring having 3, 4, 5, 6, 7, 8, 9, 10, 11, 12, 13 or 14 carbon atoms. Examples of carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, fluorenyl, phenyl, naphthyl, indanyl, adamantyl and tetrahydronaphthyl. Bridged rings are also included in the definition of carbocycle, including, for example, [3.3.0]bicyclooctane, [4.3.0]bicyclononane, [4.4.0]bicyclodecane and [2.2.2]bicyclooctane. A bridged ring occurs when one or more carbon atoms link two non-adjacent carbon atoms. In some embodiments, bridge rings are one or two carbon atoms. It is noted that a bridge always converts a monocyclic ring into a tricyclic ring. When a ring is bridged, the substituents recited for the ring may also be present on the bridge. Fused (e.g., naphthyl, tetrahydronaphthyl) and spiro rings are also included.

As used herein, "heterocycle" or "heterocyclic group" includes any ring structure (saturated, unsaturated, or aromatic) which contains at least one ring heteroatom (e.g., N, O or S). Heterocycle includes heterocycloalkyl and heteroaryl. Examples of heterocycles include, but are not limited to, morpholine, pyrrolidine, tetrahydrothiophene, piperidine, piperazine, oxetane, pyran, tetrahydropyran, azetidine, and tetrahydrofuran.

Examples of heterocyclic groups include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2,4-oxadiazol5(4H)-one, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl and xanthenyl.

The term "substituted," as used herein, means that any one or more hydrogen atoms on the designated atom is replaced with a selection from the indicated groups, provided that the designated atom's normal valency is not exceeded, and that the substitution results in a stable compound. When a substituent is oxo or keto (i.e., =O), then 2 hydrogen atoms on the atom are replaced. Keto substituents are not present on aromatic moieties. Ring double bonds, as used herein, are double bonds that are formed between two adjacent ring atoms (e.g., C=C, C=N or N=N). "Stable compound" and "stable structure" are meant to indicate a compound that is sufficiently robust to survive isolation to a useful degree of purity from a reaction mixture, and formulation into an efficacious therapeutic agent.

When a bond to a substituent is shown to cross a bond connecting two atoms in a ring, then such substituent may be bonded to any atom in the ring. When a substituent is listed without indicating the atom via which such substituent is bonded to the rest of the compound of a given formula, then such substituent may be bonded via any atom in such formula. Combinations of substituents and/or variables are permissible, but only if such combinations result in stable compounds.

When any variable (e.g., $R_1$) occurs more than one time in any constituent or formula for a compound, its definition at each occurrence is independent of its definition at every other occurrence. Thus, for example, if a group is shown to be substituted with 0-2 $R_1$ moieties, then the group may optionally be substituted with up to two $R_1$ moieties and $R_1$ at each occurrence is selected independently from the definition of $R_1$. Also, combinations of substituents and/or variables are permissible, but only if such combinations result in stable compounds.

The term "hydroxy" or "hydroxyl" includes groups with an —OH or —O—.

As used herein, "halo" or "halogen" refers to fluoro, chloro, bromo and iodo. The term "perhalogenated" generally refers to a moiety wherein all hydrogen atoms are replaced by halogen atoms. The term "haloalkyl" or "haloalkoxyl" refers to an alkyl or alkoxyl substituted with one or more halogen atoms.

The term "carbonyl" includes compounds and moieties which contain a carbon connected with a double bond to an oxygen atom. Examples of moieties containing a carbonyl include, but are not limited to, aldehydes, ketones, carboxylic acids, amides, esters, anhydrides, etc.

The term "carboxyl" refers to —COOH or its $C_1$-$C_6$ alkyl ester.

"Acyl" includes moieties that contain the acyl radical (R—C(O)—) or a carbonyl group. "Substituted acyl" includes acyl groups where one or more of the hydrogen atoms are replaced by, for example, alkyl groups, alkynyl groups, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

"Aroyl" includes moieties with an aryl or heteroaromatic moiety bound to a carbonyl group. Examples of aroyl groups include phenylcarboxy, naphthyl carboxy, etc.

"Alkoxyalkyl," "alkylaminoalkyl," and "thioalkoxyalkyl" include alkyl groups, as described above, wherein oxygen, nitrogen, or sulfur atoms replace one or more hydrocarbon backbone carbon atoms.

The term "alkoxy" or "alkoxyl" includes substituted and unsubstituted alkyl, alkenyl and alkynyl groups covalently linked to an oxygen atom. Examples of alkoxy groups or alkoxyl radicals include, but are not limited to, methoxy, ethoxy, isopropyloxy, propoxy, butoxy and pentoxy groups. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy and trichloromethoxy.

The term "ether" or "alkoxy" includes compounds or moieties which contain an oxygen bonded to two carbon atoms or heteroatoms. For example, the term includes "alkoxyalkyl," which refers to an alkyl, alkenyl, or alkynyl group covalently bonded to an oxygen atom which is covalently bonded to an alkyl group.

The term "ester" includes compounds or moieties which contain a carbon or a heteroatom bound to an oxygen atom which is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc.

The term "thioalkyl" includes compounds or moieties which contain an alkyl group connected with a sulfur atom. The thioalkyl groups can be substituted with groups such as alkyl, alkenyl, alkynyl, halogen, hydroxyl, alkylcarbonyloxy, arylcarbonyloxy, alkoxycarbonyloxy, aryloxycarbonyloxy, carboxylate, carboxyacid, alkylcarbonyl, arylcarbonyl, alkoxycarbonyl, aminocarbonyl, alkylaminocarbonyl, dialkylaminocarbonyl, alkylthiocarbonyl, alkoxyl, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties.

The term "thiocarbonyl" or "thiocarboxy" includes compounds and moieties which contain a carbon connected with a double bond to a sulfur atom.

The term "thioether" includes moieties which contain a sulfur atom bonded to two carbon atoms or heteroatoms. Examples of thioethers include, but are not limited to alkthioalkyls, alkthioalkenyls, and alkthioalkynyls. The term "alkthioalkyls" include moieties with an alkyl, alkenyl, or alkynyl group bonded to a sulfur atom which is bonded to an alkyl group. Similarly, the term "alkthioalkenyls" refers to moieties wherein an alkyl, alkenyl or alkynyl group is bonded to a sulfur atom which is covalently bonded to an alkenyl group; and alkthioalkynyls" refers to moieties wherein an alkyl, alkenyl or alkynyl group is bonded to a sulfur atom which is covalently bonded to an alkynyl group.

As used herein, "amine" or "amino" refers to unsubstituted or substituted —$NH_2$. "Alkylamino" includes groups of compounds wherein nitrogen of —$NH_2$ is bound to at least one alkyl group. Examples of alkylamino groups include benzylamino, methylamino, ethylamino, phenethylamino, etc. "Dialkylamino" includes groups wherein the nitrogen of —$NH_2$ is bound to at least two additional alkyl groups. Examples of dialkylamino groups include, but are not limited to, dimethylamino and diethylamino. "Arylamino" and "diarylamino" include groups wherein the nitrogen is bound to at least one or two aryl groups, respectively. "Aminoaryl" and "aminoaryloxy" refer to aryl and aryloxy substituted with amino. "Alkylarylamino," "alkylaminoaryl" or "arylaminoalkyl" refers to an amino group which is bound to at least one alkyl group and at least one aryl group. "Alkaminoalkyl" refers to an alkyl, alkenyl, or alkynyl group bound to a nitrogen atom which is also bound to an alkyl group. "Acylamino" includes groups wherein nitrogen is bound to an acyl group. Examples of acylamino include, but are not limited to, alkylcarbonylamino, arylcarbonylamino, carbamoyl and ureido groups.

The term "amide" or "aminocarboxy" includes compounds or moieties that contain a nitrogen atom that is bound to the carbon of a carbonyl or a thiocarbonyl group. The term includes "alkaminocarboxy" groups that include alkyl, alkenyl or alkynyl groups bound to an amino group which is bound to the carbon of a carbonyl or thiocarbonyl group. It also includes "arylaminocarboxy" groups that include aryl or heteroaryl moieties bound to an amino group that is bound to the carbon of a carbonyl or thiocarbonyl group. The terms "alkylaminocarboxy", "alkenylaminocarboxy", "alkynylaminocarboxy" and "arylaminocarboxy" include moieties wherein alkyl, alkenyl, alkynyl and aryl moieties, respectively, are bound to a nitrogen atom which is in turn bound to the carbon of a carbonyl group. Amides can be substituted with substituents such as straight chain alkyl, branched alkyl, cycloalkyl, aryl, heteroaryl or heterocycle. Substituents on amide groups may be further substituted.

Compounds of the present disclosure that contain nitrogens can be converted to N-oxides by treatment with an oxidizing agent (e.g., 3-chloroperoxybenzoic acid (mCPBA) and/or hydrogen peroxides) to afford other compounds of the present disclosure. Thus, all shown and claimed nitrogen-containing compounds are considered, when allowed by valency and structure, to include both the compound as shown and its N-oxide derivative (which can be designated as N→O or N$^+$—O$^-$). Furthermore, in other instances, the nitrogens in the compounds of the present disclosure can be converted to N-hydroxy or N-alkoxy compounds. For example, N-hydroxy compounds can be prepared by oxidation of the parent amine by an oxidizing agent such as m-CPBA. All shown and claimed nitrogen-containing compounds are also considered, when allowed by valency and structure, to cover both the compound as shown and its N-hydroxy (i.e., N—OH) and N-alkoxy (i.e., N—OR, wherein R is substituted or unsubstituted $C_1$-$C_6$ alkyl, $C_1$-$C_6$ alkenyl, $C_1$-$C_6$ alkynyl, 3-14-membered carbocycle or 3-14-membered heterocycle) derivatives.

"Isomerism" means compounds that have identical molecular formulae but differ in the sequence of bonding of their atoms or in the arrangement of their atoms in space. Isomers that differ in the arrangement of their atoms in space are termed "stereoisomers." Stereoisomers that are not mirror images of one another are termed "diastereoisomers," and stereoisomers that are non-superimposable mirror images of each other are termed "enantiomers" or sometimes optical isomers. A mixture containing equal amounts of individual enantiomeric forms of opposite chirality is termed a "racemic mixture."

A carbon atom bonded to four nonidentical substituents is termed a "chiral center."

"Chiral isomer" means a compound with at least one chiral center. Compounds with more than one chiral center may exist either as an individual diastereomer or as a mixture of diastereomers, termed "diastereomeric mixture." When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the Sequence Rule of Cahn, Ingold and Prelog. (Cahn et al., *Angew. Chem. Inter. Edit.* 1966, 5, 385; errata 511; Cahn et al., *Angew. Chem.* 1966, 78, 413; Cahn and Ingold, *J. Chem. Soc.* 1951 (London), 612; Cahn et al., *Experientia* 1956, 12, 81; Cahn, *J. Chem. Educ.* 1964, 41, 116).

"Geometric isomer" means the diastereomers that owe their existence to hindered rotation about double bonds or a cycloalkyl linker (e.g., 1,3-cyclobutyl). These configurations are differentiated in their names by the prefixes cis and trans, or Z and E, which indicate that the groups are on the same or opposite side of the double bond in the molecule according to the Cahn-Ingold-Prelog rules.

It is to be understood that the small molecule EZH2 inhibitors provided herein may be depicted as different chiral isomers or geometric isomers. It should also be understood that when compounds have chiral isomeric or geometric isomeric forms, all isomeric forms are intended to be included in the scope of the present disclosure, and the naming of the compounds does not exclude any isomeric forms.

Furthermore, the structures and other compounds discussed in this disclosure include all atropic isomers thereof "Atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques, it has been possible to separate mixtures of two atropic isomers in select cases.

"Tautomer" is one of two or more structural isomers that exist in equilibrium and is readily converted from one isomeric form to another. This conversion results in the formal migration of a hydrogen atom accompanied by a switch of adjacent conjugated double bonds. Tautomers exist as a mixture of a tautomeric set in solution. In solutions where tautomerization is possible, a chemical equilibrium of the tautomers will be reached. The exact ratio of the tautomers depends on several factors, including temperature, solvent and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs. Ring-chain tautomerism arises as a result of the aldehyde group (—CHO) in a sugar chain molecule reacting with one of the hydroxy groups (—OH) in the same molecule to give it a cyclic (ring-shaped) form as exhibited by glucose.

Common tautomeric pairs are: ketone-enol, amide-nitrile, lactam-lactim, amide-imidic acid tautomerism in heterocyclic rings (e.g., in nucleobases such as guanine, thymine and cytosine), imine-enamine and enamine-enamine. An example of keto-enol equilibria is between pyridin-2(1H)-ones and the corresponding pyridin-2-ols, as shown below.

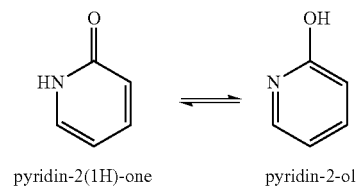 [SMILES: O=c1cccc[nH]1 ; Oc1ccccn1]

pyridin-2(1H)-one      pyridin-2-ol

It is to be understood that the compounds of the present disclosure may be depicted as different tautomers. It should also be understood that when compounds have tautomeric forms, all tautomeric forms are intended to be included in the scope of the present disclosure, and the naming of the compounds does not exclude any tautomer form.

The EZH2 inhibitors of Formulae (I)-(VIa) disclosed herein include the compounds themselves, as well as their salts and their solvates, if applicable. A salt, for example, can be formed between an anion and a positively charged group (e.g., amino) on an aryl- or heteroaryl-substituted benzene compound. Suitable anions include chloride, bromide, iodide, sulfate, bisulfate, sulfamate, nitrate, phosphate, citrate, methanesulfonate, trifluoroacetate, glutamate, glucuronate, glutarate, malate, maleate, succinate, fumarate, tartrate, tosylate, salicylate, lactate, naphthalenesulfonate, and acetate (e.g., trifluoroacetate). The term "pharmaceutically acceptable anion" refers to an anion suitable for forming a pharmaceutically acceptable salt. Likewise, a salt can also be formed between a cation and a negatively charged group (e.g., carboxylate) on an aryl- or heteroaryl-substituted benzene compound. Suitable cations include sodium ion, potassium ion, magnesium ion, calcium ion, and an ammonium cation such as tetramethylammonium ion. The aryl- or heteroaryl-substituted benzene compounds also include those salts containing quaternary nitrogen atoms. In the salt form, it is understood that the ratio of the compound to the cation or anion of the salt can be 1:1, or any ration other than 1:1, e.g., 3:1, 2:1, 1:2, or 1:3.

Additionally, the EZH2 inhibitory compounds of the present disclosure, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

"Solvate" means solvent addition forms that contain either stoichiometric or non-stoichiometric amounts of solvent. Some compounds have a tendency to trap a fixed molar ratio of solvent molecules in the crystalline solid state, thus forming a solvate. If the solvent is water the solvate formed is a hydrate; and if the solvent is alcohol, the solvate formed is an alcoholate. Hydrates are formed by the combination of one or more molecules of water with one molecule of the substance in which the water retains its molecular state as $H_2O$.

As used herein, the term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar or comparable in function and appearance, but not in structure or origin to the reference compound.

As used herein, the term "derivative" refers to compounds that have a common core structure, and are substituted with various groups as described herein. For example, all of the compounds represented by Formula (I) are aryl- or heteroaryl-substituted benzene compounds, and have Formula (I) as a common core.

Some embodiments of the present disclosure embrace some or all isotopes of atoms occurring in the present EZH2 inhibitory compounds. Isotopes include those atoms having the same atomic number but different mass numbers. By way of general example and without limitation, isotopes of hydrogen include tritium and deuterium, and isotopes of carbon include C-13 and C-14.

In certain aspects of the disclosure an inhibitor of EZH2 "selectively inhibits" histone methyltransferase activity of the mutant EZH2 when it inhibits histone methyltransferase activity of the mutant EZH2 more effectively than it inhibits histone methyltransferase activity of wild-type EZH2. For example, in some embodiments the selective inhibitor has an IC50 for the mutant EZH2 that is at least 40 percent lower than the IC50 for wild-type EZH2. In some embodiments, the selective inhibitor has an IC50 for the mutant EZH2 that is at least 50 percent lower than the IC50 for wild-type EZH2. In some embodiments, the selective inhibitor has an IC50 for the mutant EZH2 that is at least 60 percent lower than the IC50 for wild-type EZH2. In some embodiments, the selective inhibitor has an IC50 for the mutant EZH2 that is at least 70 percent lower than the IC50 for wild-type EZH2. In some embodiments, the selective inhibitor has an IC50 for the mutant EZH2 that is at least 80 percent lower than the IC50 for wild-type EZH2. In some embodiments, the selective inhibitor has an IC50 for the mutant EZH2 that is at least 90 percent lower than the IC50 for wild-type EZH2.

In some embodiments, the selective inhibitor of a mutant EZH2 exerts essentially no inhibitory effect on wild-type EZH2.

In certain aspects, the inhibitor (e.g. compound disclosed herein) inhibits conversion of H3-K27me2 to H3-K27me3. In some embodiments the inhibitor is said to inhibit trimethylation of H3-K27. Since conversion of H3-K27me1 to H3-K27me2 precedes conversion of H3-K27me2 to H3-K27me3, an inhibitor of conversion of H3-K27me1 to H3-K27me2 naturally also inhibits conversion of H3-K27me2 to H3-K27me3, i.e., it inhibits trimethylation of H3-K27. It is also possible to inhibit conversion of H3-K27me2 to H3-K27me3 without inhibition of conversion of H3-K27me1 to H3-K27me2. Inhibition of this type would also result in inhibition of trimethylation of H3-K27, albeit without inhibition of dimethylation of H3-K27.

In some embodiments the inhibitor (e.g. compound disclosed herein) inhibits conversion of H3-K27me1 to H3-K27me2 and the conversion of H3-K27me2 to H3-K27me3. Such inhibitor may directly inhibit the conversion of H3-K27me1 to H3-K27me2 alone. Alternatively, such inhibitor may directly inhibit both the conversion of H3-K27me1 to H3-K27me2 and the conversion of H3-K27me2 to H3-K27me3.

In certain aspects, the EZH2 inhibitor (e.g. compound disclosed herein) inhibits histone methyltransferase activity. Inhibition of histone methyltransferase activity can be detected using any suitable method. The inhibition can be measured, for example, either in terms of rate of histone methyltransferase activity or as product of histone methyltransferase activity.

In some embodiments, strategies, treatment modalities, methods, combinations, and compositions are provided that are characterized by a measurable inhibition of EZH2 activity, for example, a measureable EZH2 inhibition as compared to a suitable control. In some embodiments, EZH2 inhibition is at least 10 percent inhibition compared to a suitable control, e.g., an EZH2 activity observed or expected in an untreated control cell, tissue, or subject. In some embodiments, the rate of EZH2 enzymatic activity in the presence of the EZH2 inhibitor is less than or equal to 90 percent of the corresponding enzymatic activity in the absence of the EZH2 inhibitor. In some embodiments, EZH2 inhibition in the presence of the EZH2 inhibitor is at least 20, 25, 30, 40, 50, 60, 70, 75, 80, 90, or 95 percent inhibition as compared to a suitable control, e.g., to activity in the absence of the inhibitor. In some embodiments, inhibition is at least 99 percent inhibition compared to a suitable control. That is, the rate of enzymatic activity in the presence of the inhibitor is less than or equal to 1 percent of the corresponding activity in the absence of the inhibitor.

Immune Checkpoint Inhibitors

Immune checkpoint proteins inhibit the action of the immune cells (e.g., T cells) against certain cells. Immune checkpoint signaling plays an important role in balancing a subject's immune response against cells targeted by the immune system (e.g., infected or malignant cells), and cells that are not targeted by immune system effectors (e.g., healthy cells). Without wishing to be bound by any particular theory, it is believed that evasion of some cancer cells from immune system surveillance and destruction is mediated by aberrant immune checkpoint signaling, wherein cancer cells modulate or abolish the host's immune response by activating one or more immune checkpoint signaling pathways in the host's immune cells.

Various immune checkpoint signaling proteins have been identified, for example, and without limitation, CTLA4, PD-1, PD-L1, LAG3, B7-H3, and Tim3, and immune checkpoint inhibitors targeting such immune checkpoint proteins have been developed. Such immune checkpoint inhibitors decrease or abolish the activity of the immune checkpoint signaling pathway they target and can thus boost the subject's immune response, e.g., against pathologic cells that otherwise escape proper immune system surveillance. For example, some immune checkpoint inhibitors have been reported to effectively inhibit immune checkpoint signaling that prevented a T-cell mediated attack of an infected or cancerous cell. Accordingly, the immune checkpoint inhibitors described herein enable or support immune system surveillance and effector functions (e.g., in the form of a T-cell attack) targeted at malignant or infective cells. Some of the immune checkpoint inhibitors referred to herein include monoclonal antibodies that specifically bind and inhibit an activity of one or more checkpoint protein(s) on an immune cell (e.g. a T cell). Immune checkpoint inhibitors of the disclosure may be used to boost the subject's immune response against any type of cancer cell.

While any checkpoint protein may be targeted, exemplary immune checkpoint inhibitors of the disclosure may target, bind, and/or inhibit an activity of a protein including, but not limited to, CTLA4, PD-1, PD-L1, LAG3, B7-H3, Tim3 or any combination thereof. Immune checkpoint inhibitors that target, bind, and/or inhibit an activity of CTLA4 may comprise Ipilimumab, Ticilimumab, AGEN-1884 or a combination thereof. Immune checkpoint inhibitors that target, bind, and/or inhibit an activity of PD-1 and/or PD-L1 may comprise Nivolumab, Pembrolizumab, Atezolizumab, Durvalumab, Avelumab, BMS-936559, AMP-224, MEDI-0680, TSR-042, BGB-108, STI-1014, KY-1003, ALN-PDL, BGB-A317, KD-033, REGN-2810, PDR-001, SHR-1210, MGD-013, PF-06801591, CX-072 or a combination thereof. Immune checkpoint inhibitors that target, bind, and/or inhibit an activity of LAG3 may comprise IMP-731, LAG-525, BMS-986016, GSK-2831781 or a combination thereof. Immune checkpoint inhibitors that target, bind, and/or inhibit an activity of B7-H3 may comprise Enoblituzumab, 1241-8H9, DS-5573 or a combination thereof. Immune checkpoint inhibitors that target, bind, and/or inhibit an activity of Tim3 may comprise MBG-453.

Combination Therapy

Some aspects of this disclosure are based on the recognition that certain disorders, e.g., certain proliferative diseases, can be more effectively treated by a combination therapy approach (e.g., by administering an EZH2 inhibitor and an immune checkpoint inhibitor to the subject) as compared to treatment with only a single therapeutic agent. For example, in some embodiments, the present disclosure provides combination therapy strategies, treatment modalities, methods, combinations, and compositions that are useful for improving the clinical outcome and/or the prognosis of a subject having a proliferative disease, e.g., a cancer, as compared to monotherapeutic approaches. In some embodiments, the combination therapy approaches provided herein result in a shorter time period being required to achieve a desired clinical outcome (e.g., partial or complete disease remission, inhibition of tumor growth, stable disease), as compared to monotherapy. In some embodiments, the combination therapy approaches provided herein result in a better clinical outcome as compared to monotherapy (e.g., complete vs. partial remission, stable vs. progressive disease, lower recurrence risk).

In some embodiments, the present disclosure provides combination therapy strategies, treatment modalities, and methods, wherein a subject in need thereof is administered an EZH2 inhibitor and an immune checkpoint inhibitor. In some embodiments, the EZH2 inhibitor is an EZH2 inhibitor as provided herein, e.g., a small molecule EZH2 inhibitor provided by any of Formulae (I)-(IVa), or by any other structure described herein, and the immune checkpoint inhibitor is a monoclonal antibody, a peptide, or a small molecule as described herein. In some embodiments, the EZH2 inhibitor is tazemetostat, or a pharmaceutically acceptable salt thereof, and the immune checkpoint inhibitor is Ipilimumab, Ticilimumab, AGEN-1884, Nivolumab, Pembrolizumab, Atezolizumab, Durvalumab, Avelumab, BMS-936559, AMP-224, MEDI-0680, TSR-042, BGB-108, STI-1014, KY-1003, ALN-PDL, BGB-A317, KD-033, REGN-2810, PDR-001, SHR-1210, MGD-013, PF-06801591, CX-072, IMP-731, LAG-525, BMS-986016, GSK-2831781, Enoblituzumab, 1241-8H9, DS-5573, or a combination thereof.

In some embodiments, combination therapy strategies, treatment modalities, and methods for the treatment of proliferative diseases are provided, wherein the EZH2 inhibitor is tazemetostat, or a pharmaceutically acceptable salt thereof, and the immune checkpoint inhibitor is Ipilimumab. For example, in some embodiments, a method is provided that comprises administering to a subject in need thereof, e.g., a subject having or being diagnosed with a proliferative disease (e.g., a cancer), a therapeutically effective amount of tazemetostat, or a pharmaceutically acceptable salt thereof, and a therapeutically effective amount of Ipilimumab.

In some embodiments, combination therapy strategies, treatment modalities, and methods for the treatment of proliferative diseases are provided, wherein the EZH2 inhibitor is tazemetostat, or a pharmaceutically acceptable salt thereof, and the immune checkpoint inhibitor is Ticilimumab. For example, in some embodiments, a method is provided that comprises administering to a subject in need thereof, e.g., a subject having or being diagnosed with a proliferative disease (e.g., a cancer), a therapeutically effective amount of tazemetostat, or a pharmaceutically acceptable salt thereof, and a therapeutically effective amount of Ticilimumab.

In some embodiments, combination therapy strategies, treatment modalities, and methods for the treatment of proliferative diseases are provided, wherein the EZH2 inhibitor is tazemetostat, or a pharmaceutically acceptable salt thereof, and the immune checkpoint inhibitor is AGEN-1884. For example, in some embodiments, a method is provided that comprises administering to a subject in need thereof, e.g., a subject having or being diagnosed with a proliferative disease (e.g., a cancer), a therapeutically effective amount of tazemetostat, or a pharmaceutically acceptable salt thereof, and a therapeutically effective amount of AGEN-1884.

In some embodiments, combination therapy strategies, treatment modalities, and methods for the treatment of proliferative diseases are provided, wherein the EZH2 inhibitor is tazemetostat, or a pharmaceutically acceptable salt thereof, and the immune checkpoint inhibitor is Nivolumab. For example, in some embodiments, a method is provided that comprises administering to a subject in need thereof, e.g., a subject having or being diagnosed with a proliferative disease (e.g., a cancer), a therapeutically effective amount of tazemetostat, or a pharmaceutically acceptable salt thereof, and a therapeutically effective amount of Nivolumab.

In some embodiments, combination therapy strategies, treatment modalities, and methods for the treatment of proliferative diseases are provided, wherein the EZH2 inhibitor is tazemetostat, or a pharmaceutically acceptable salt thereof, and the immune checkpoint inhibitor is Pembrolizumab. For example, in some embodiments, a method is provided that comprises administering to a subject in need thereof, e.g., a subject having or being diagnosed with a proliferative disease (e.g., a cancer), a therapeutically effective amount of tazemetostat, or a pharmaceutically acceptable salt thereof, and a therapeutically effective amount of Pembrolizumab.

In some embodiments, combination therapy strategies, treatment modalities, and methods for the treatment of proliferative diseases are provided, wherein the EZH2 inhibitor is tazemetostat, or a pharmaceutically acceptable salt thereof, and the immune checkpoint inhibitor is Atezolizumab. For example, in some embodiments, a method is provided that comprises administering to a subject in need thereof, e.g., a subject having or being diagnosed with a proliferative disease (e.g., a cancer), a therapeutically effective amount of tazemetostat, or a pharmaceutically acceptable salt thereof, and a therapeutically effective amount of Atezolizumab.

In some embodiments, combination therapy strategies, treatment modalities, and methods for the treatment of proliferative diseases are provided, wherein the EZH2 inhibitor is tazemetostat, or a pharmaceutically acceptable salt thereof, and the immune checkpoint inhibitor is Durvalumab. For example, in some embodiments, a method is provided that comprises administering to a subject in need thereof, e.g., a subject having or being diagnosed with a proliferative disease (e.g., a cancer), a therapeutically effective amount of tazemetostat, or a pharmaceutically acceptable salt thereof, and a therapeutically effective amount of Durvalumab.

In some embodiments, combination therapy strategies, treatment modalities, and methods for the treatment of proliferative diseases are provided, wherein the EZH2 inhibitor is tazemetostat, or a pharmaceutically acceptable salt thereof, and the immune checkpoint inhibitor is Avelumab. For example, in some embodiments, a method is provided that comprises administering to a subject in need thereof, e.g., a subject having or being diagnosed with a proliferative disease (e.g., a cancer), a therapeutically effective amount of tazemetostat, or a pharmaceutically acceptable salt thereof, and a therapeutically effective amount of Avelumab.

In some embodiments, combination therapy strategies, treatment modalities, and methods for the treatment of proliferative diseases are provided, wherein the EZH2 inhibitor is tazemetostat, or a pharmaceutically acceptable salt thereof, and the immune checkpoint inhibitor is BMS-936559. For example, in some embodiments, a method is provided that comprises administering to a subject in need thereof, e.g., a subject having or being diagnosed with a proliferative disease (e.g., a cancer), a therapeutically effective amount of tazemetostat, or a pharmaceutically acceptable salt thereof, and a therapeutically effective amount of BMS-936559.

In some embodiments, combination therapy strategies, treatment modalities, and methods for the treatment of proliferative diseases are provided, wherein the EZH2 inhibitor is tazemetostat, or a pharmaceutically acceptable salt thereof, and the immune checkpoint inhibitor is AMP-224. For example, in some embodiments, a method is provided that comprises administering to a subject in need thereof, e.g., a subject having or being diagnosed with a proliferative disease (e.g., a cancer), a therapeutically effective amount of tazemetostat, or a pharmaceutically acceptable salt thereof, and a therapeutically effective amount of AMP-224.

In some embodiments, combination therapy strategies, treatment modalities, and methods for the treatment of proliferative diseases are provided, wherein the EZH2 inhibitor is tazemetostat, or a pharmaceutically acceptable salt thereof, and the immune checkpoint inhibitor is MEDI-0680. For example, in some embodiments, a method is provided that comprises administering to a subject in need thereof, e.g., a subject having or being diagnosed with a proliferative disease (e.g., a cancer), a therapeutically effective amount of tazemetostat, or a pharmaceutically acceptable salt thereof, and a therapeutically effective amount of MEDI-0680.

In some embodiments, combination therapy strategies, treatment modalities, and methods for the treatment of proliferative diseases are provided, wherein the EZH2 inhibitor is tazemetostat, or a pharmaceutically acceptable salt thereof, and the immune checkpoint inhibitor is Enoblituzumab. For example, in some embodiments, a method is provided that comprises administering to a subject in need thereof, e.g., a subject having or being diagnosed with a proliferative disease (e.g., a cancer), a therapeutically effective amount of tazemetostat, or a pharmaceutically acceptable salt thereof, and a therapeutically effective amount of Enoblituzumab.

In some embodiments, the method further includes monitoring the methylation status in a target cell or tissue in the subject, e.g., by methods described herein or otherwise known to those in the art, and/or monitoring the immune response status in the subject, e.g., by methods described herein or otherwise known in the art.

Pharmaceutical Formulations

In some embodiments, the EZH2 inhibitor and the immune checkpoint inhibitor are provided in separate pharmaceutical formulations, and administered to the subject independently, e.g., sequentially. In some embodiments, the EZH2 inhibitor is formulated for oral administration and the immune response inhibitor is formulated for parenteral administration.

The disclosure also provides pharmaceutical compositions and combinations comprising a compound of Formulae (I)-(VIa) or pharmaceutically acceptable salts thereof, and one or more other therapeutic agents disclosed herein, e.g., one or more immune checkpoint inhibitors, mixed with pharmaceutically suitable carriers or excipient(s) at doses to treat or prevent a disease or condition as described herein. In one aspect, the disclosure also provides pharmaceutical compositions comprising any compound of Table I or pharmaceutically acceptable salts thereof, and one or more therapeutic agents, mixed with pharmaceutically suitable carriers or excipient (s) at doses to treat or prevent a disease or condition as described herein. In another aspect, the disclosure also provides pharmaceutical compositions comprising Compound 44

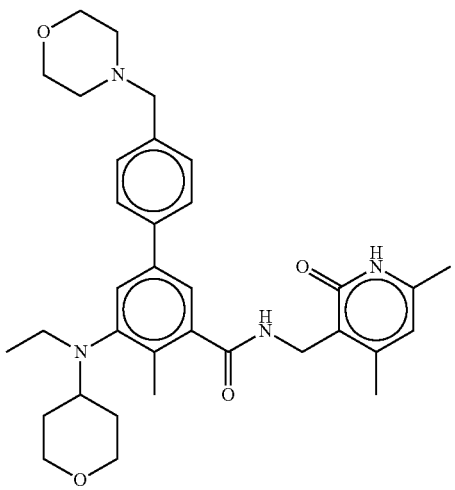

or pharmaceutically acceptable salts thereof, and one or more therapeutic agents, mixed with pharmaceutically suitable carriers or excipient(s) at doses to treat or prevent a disease or condition as described herein. The pharmaceutical compositions of the disclosure can also be administered in combination with other therapeutic agents or therapeutic modalities simultaneously, sequentially, or in alternation.

Mixtures or combinations of compositions of the disclosure can also be administered to the patient as a simple mixture or in suitable formulated pharmaceutical compositions. For example, one aspect of the disclosure relates to a pharmaceutical composition or combination comprising a therapeutically effective dose of an EZH2 inhibitor of Formulae (I)-(VIa), or a pharmaceutically acceptable salt, hydrate, enantiomer or stereoisomer thereof, one or more other therapeutic agents, and a pharmaceutically acceptable diluent or carrier.

A "pharmaceutical composition" is a formulation containing the compounds of the disclosure in a form suitable for administration to a subject. A compound of Formulae (I)-(VIa) and one or more other therapeutic agents described herein each can be formulated individually or in multiple pharmaceutical compositions in any combinations of the active ingredients. Accordingly, one or more administration routes can be properly elected based on the dosage form of each pharmaceutical composition. Alternatively, a compound of Formulae (I)-(VIa) and one or more other therapeutic agents described herein can be formulated as one pharmaceutical composition.

In some embodiments, the pharmaceutical composition is in bulk or in unit dosage form. The unit dosage form is any of a variety of forms, including, for example, a capsule, an IV bag, a tablet, a single pump on an aerosol inhaler or a vial. The quantity of active ingredient (e.g., a formulation of the disclosed compound or salt, hydrate, solvate or isomer thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this disclosure include powders, sprays, ointments, pastes, creams, lotions, gels, solutions, patches and inhalants. In some embodiments, the active compound is mixed under sterile conditions with a pharmaceutically acceptable carrier, and with any preservatives, buffers, or propellants that are required.

As used herein, the phrase "pharmaceutically acceptable" refers to those compounds, anions, cations, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

A pharmaceutical composition of the disclosure is formulated to be compatible with its intended route of administration. Examples of routes of administration include parenteral, e.g., intravenous, intradermal, subcutaneous, oral (e.g., inhalation), transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

A composition of the disclosure, e.g., a formulation comprising an EZH2 inhibitor and/or an immune checkpoint inhibitor can be administered to a subject in many of the well-known methods currently used for chemotherapeutic treatment. For example, for treatment of cancers, a formulation comprising an EZH2 inhibitor and/or an immune checkpoint inhibitor be injected directly into tumors, injected into the blood stream or body cavities or taken orally or applied through the skin with patches. The dose chosen for the EZH2 inhibitor and for the immune checkpoint inhibitor should be sufficient to constitute effective treatment but not so high as to cause unacceptable side effects. The state of the disease condition (e.g., cancer, precancer, and the like) and the health of the patient should preferably be closely monitored during and for a reasonable period after treatment.

The term "therapeutically effective amount", as used herein, refers to an amount of a pharmaceutical agent to treat, ameliorate, or prevent an identified disease or condition, or to exhibit a detectable therapeutic or inhibitory effect. Exemplary, non-limiting effective amounts and effective dosage ranges of EZH2 inhibitors and immune response inhibitors are provided herein. The effect can be detected by any assay method known in the art. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician. In a preferred aspect, the disease or condition to be treated is cancer. In another aspect, the disease or condition to be treated is a cell proliferative disorder.

In certain embodiments the therapeutically effective amount of each pharmaceutical agent used in combination will be lower when used in combination in comparison to monotherapy with each agent alone. Such lower therapeutically effective amount could afford for lower toxicity of the therapeutic regimen.

For many of the compounds described herein, e.g., various EZH2 inhibitors and various immune checkpoint inhibitors, a therapeutically effective amount or an effective dosage range has been reported. In some embodiments, an effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are preferred. The dosage may vary within this range depending upon the dosage form employed, sensitivity of the patient, and the route of administration.

Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

The pharmaceutical compositions containing active compounds of the disclosure may be manufactured in a manner that is generally known, e.g., by means of conventional mixing, dissolving, granulating, dragee-making, levigating, emulsifying, encapsulating, entrapping, or lyophilizing processes. Pharmaceutical compositions may be formulated in a conventional manner using one or more pharmaceutically acceptable carriers comprising excipients and/or auxiliaries that facilitate processing of the active compounds into preparations that can be used pharmaceutically. Of course, the appropriate formulation is dependent upon the route of administration chosen.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol and sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible pharmaceutically acceptable carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The active compounds can be prepared with pharmaceutically acceptable carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the disclosure are dictated by and directly dependent on the unique characteristics of the active compound and the particular therapeutic effect to be achieved.

In some embodiments of therapeutic applications, the dosages of the EZH2 inhibitors and/or the immune checkpoint inhibitors described herein, e.g., compositions comprising a compound of Formulae (I)-(VIa), tazemetostat, and/or an immune checkpoint inhibitor, or the pharmaceutical compositions used in accordance with the disclosure, vary depending on the specific agent(s) used, the age, weight, and clinical condition of the recipient patient, and the experience and judgment of the clinician or practitioner administering the therapy, among other factors affecting the selected dosage. Generally, the dose of the active ingredient(s) should be sufficient to result in slowing, and preferably regressing, the growth of the tumors and also preferably causing complete regression of the cancer. In some embodiments, dosages can range from about 0.01 mg/kg per day to about 5000 mg/kg per day. In preferred aspects, dosages can range from about 1 mg/kg per day to about 1000 mg/kg per day. In an aspect, the dose will be in the range of about 0.1 mg/day to about 50 g/day; about 0.1 mg/day to about 25 g/day; about 0.1 mg/day to about 10 g/day; about 0.1 mg to about 3 g/day; or about 0.1 mg to about 1 g/day, in single, divided, or continuous doses (which dose may be adjusted for the patient's weight in kg, body surface area in $m^2$, and age in years). Additional suitable dosages are provided elsewhere herein. For example, regression of a tumor in a patient may be measured with reference to the diameter of a tumor. Decrease in the diameter of a tumor indicates regression. Regression is also indicated by failure of tumors to reoccur after treatment has stopped. As used herein, the term "dosage effective manner" refers to amount of an active compound to produce the desired biological effect in a subject or cell.

As used herein, "pharmaceutically acceptable salts" refer to derivatives of the compounds of the disclosure, e.g., of the small molecule EZH2 inhibitors described herein, wherein the parent compound is modified by making acid or base salts thereof. Examples of pharmaceutically acceptable salts, e.g., of the EZH2 inhibitors provided herein, include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, 1,2-ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, toluene sulfonic, and the commonly occurring amine acids, e.g., glycine, alanine, phenylalanine, arginine, etc.

Other examples of pharmaceutically acceptable salts include hexanoic acid, cyclopentane propionic acid, pyruvic acid, malonic acid, 3-(4-hydroxybenzoyl)benzoic acid, cinnamic acid, 4-chlorobenzenesulfonic acid, 2-naphthalenesulfonic acid, 4-toluenesulfonic acid, camphorsulfonic acid, 4-methylbicyclo-[2.2.2]-oct-2-ene-1-carboxylic acid, 3-phenylpropionic acid, trimethylacetic acid, tertiary butylacetic acid, muconic acid, and the like. The disclosure also encompasses salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

It should be understood that all references to pharmaceutically acceptable salts include solvent addition forms (solvates), of the same salt.

The composition of the disclosure may also be prepared as esters, for example, pharmaceutically acceptable esters. For example, a carboxylic acid function group in a compound can be converted to its corresponding ester, e.g., a methyl, ethyl or other ester. Also, an alcohol group in a compound can be converted to its corresponding ester, e.g., acetate, propionate or other ester.

The composition, or pharmaceutically acceptable salts or solvates thereof, are administered orally, nasally, transdermally, pulmonary, inhalationally, buccally, sublingually, intraperitoneally, subcutaneously, intramuscularly, intravenously, rectally, intrapleurally, intrathecally and parenterally. In some embodiments, the compound is administered orally. One skilled in the art will recognize the advantages of certain routes of administration.

The dosage regimen utilizing the compounds is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Techniques for formulation and administration of the disclosed compounds of the disclosure can be found in *Remington: the Science and Practice of Pharmacy*, 19$^{th}$ edition, Mack Publishing Co., Easton, Pa. (1995). In some embodiments, the compounds described herein, and the pharmaceutically acceptable salts thereof, are used in pharmaceutical preparations in combination with a pharmaceutically acceptable carrier or diluent. Suitable pharmaceutically acceptable carriers include inert solid fillers or diluents and sterile aqueous or organic solutions. The compounds will be present in such pharmaceutical compositions in amounts sufficient to provide the desired dosage amount in the range described herein.

All percentages and ratios used herein, unless otherwise indicated, are by weight. Other features and advantages of the disclosure are apparent from the different examples. The provided examples illustrate different components and methodology useful in practicing the disclosure. The examples do not limit the claimed invention. Based on the present disclosure the skilled artisan can identify and employ other components and methodology useful for practicing the disclosure.

In some embodiments, a "subject in need thereof" is a subject having a disorder in which EZH2-mediated protein methylation plays a part, or a subject having an increased risk of developing such disorder relative to the population at large. In some embodiments, the subject has a disorder in which immune system evasion also plays a role, e.g., immune system evasion of cancer cells via immune checkpoint signaling. In some embodiments, a subject in need thereof has a proliferative disease, e.g., a cancer. A "subject" includes a mammal. The mammal can be e.g., any mammal, e.g., a human, primate, bird, mouse, rat, fowl, dog, cat, cow, horse, goat, camel, sheep or a pig. Preferably, the mammal is a human.

In some embodiments, the subject is a human subject who has been diagnosed with, has symptoms of, or is at risk of developing a cancer or a precancerous condition. In some embodiments, the subject expresses a mutant EZH2 protein. For example, a mutant EZH2 comprising one or more mutations, wherein the mutation is a substitution, a point mutation, a nonsense mutation, a missense mutation, a deletion, or an insertion or any other EZH2 mutation described herein. In some embodiments, the subject expresses a wild type EZH2 protein.

A subject in need thereof may have refractory or resistant cancer. "Refractory or resistant cancer" means cancer that does not respond to treatment, e.g., to treatment with a monotherapy, e.g., a monotherapy with an immune checkpoint inhibitor alone or with an EZH2 inhibitor alone. In some embodiments, the cancer may be refractory or resistant to the standard of care treatment for that particular type of cancer. The cancer may be resistant at the beginning of treatment or it may become resistant during treatment. In some embodiments, the subject in need thereof has cancer recurrence following remission on most recent therapy. In some embodiments, the subject in need thereof received and failed all known effective therapies for cancer treatment. In some embodiments, the subject in need thereof received at least one prior therapy. In certain embodiments the prior therapy is monotherapy. In certain embodiments the prior therapy is combination therapy.

In some embodiments, a subject in need thereof may have a secondary cancer as a result of a previous therapy. "Secondary cancer" means cancer that arises due to or as a result from previous carcinogenic therapies, such as chemotherapy.

The subject may also exhibit resistance to EZH2 histone methyltransferase inhibitors or any other therapeutic agent.

As used herein, the term "responsiveness" is interchangeable with terms "responsive", "sensitive", and "sensitivity", and it is meant that a subject is showing therapeutic responses when administered a composition of the disclosure, e.g., tumor cells or tumor tissues of the subject undergo apoptosis and/or necrosis, and/or display reduced growing, dividing, or proliferation. This term is also meant that a subject will or has a higher probability, relative to the population at large, of showing therapeutic responses when administered a composition of the disclosure, e.g., tumor cells or tumor tissues of the subject undergo apoptosis and/or necrosis, and/or display reduced growing, dividing, or proliferation.

The term "sample" refers to any biological sample derived from the subject, includes but is not limited to, cells, tissues samples, body fluids (including, but not limited to, mucus, blood, plasma, serum, urine, saliva, and semen), tumor cells, and tumor tissues. Preferably, the sample is selected from bone marrow, peripheral blood cells, blood, plasma and serum. Samples can be provided by the subject under treatment or testing. Alternatively samples can be obtained by the physician according to routine practice in the art.

As used herein, a "normal cell" is a cell that cannot be classified as part of a "cell proliferative disorder". A normal cell lacks unregulated or abnormal growth, or both, that can lead to the development of an unwanted condition or disease. Preferably, a normal cell possesses normally functioning cell cycle checkpoint control mechanisms.

As used herein, "contacting a cell" refers to a condition in which a compound or other composition of matter is in direct contact with a cell, or is close enough to induce a desired biological effect in a cell.

As used herein, "treating" or "treat" describes the management and care of a patient for the purpose of combating a disease, condition, or disorder and includes the administration of an EZH2 inhibitor and/or an immune checkpoint inhibitor, to alleviate the symptoms or complications of a disease, condition or disorder, or to eliminate the disease, condition or disorder.

Cancer

A "cancer cell" or "cancerous cell" is a cell manifesting a cell proliferative disorder that is a cancer. Any reproducible means of measurement may be used to identify cancer cells or precancerous cells. Cancer cells or precancerous cells can be identified by histological typing or grading of a tissue sample (e.g., a biopsy sample). Cancer cells or precancerous cells can be identified through the use of appropriate molecular markers.

Exemplary cancers suitable for the strategies, treatment modalities, methods, combinations, and compositions provided herein include, but are not limited to, adrenocortical carcinoma, AIDS-related cancers, AIDS-related lymphoma, anal cancer, anorectal cancer, cancer of the anal canal, appendix cancer, childhood cerebellar astrocytoma, childhood cerebral astrocytoma, basal cell carcinoma, skin cancer (non-melanoma), biliary cancer, extrahepatic bile duct cancer, intrahepatic bile duct cancer, bladder cancer, urinary bladder cancer, bone and joint cancer, osteosarcoma and malignant fibrous histiocytoma, brain cancer, brain tumor, brain stem glioma, cerebellar astrocytoma, cerebral astrocytoma/malignant glioma, ependymoma, medulloblastoma, supratentorial primitive neuroectodermal tumors, visual pathway and hypothalamic glioma, breast cancer, bronchial adenomas/carcinoids, carcinoid tumor, gastrointestinal, nervous system cancer, nervous system lymphoma, central nervous system cancer, central nervous system lymphoma, cervical cancer, childhood cancers, chronic lymphocytic leukemia, chronic myelogenous leukemia, chronic myeloproliferative disorders, colon cancer, colorectal cancer, cutaneous T-cell lymphoma, lymphoid neoplasm, mycosis fungoides, Sezary Syndrome, endometrial cancer, esophageal cancer, extracranial germ cell tumor, extragonadal germ cell tumor, extrahepatic bile duct cancer, eye cancer, intraocular melanoma, retinoblastoma, gallbladder cancer, gastric (stomach) cancer, gastrointestinal carcinoid tumor, gastrointestinal stromal tumor (GIST), germ cell tumor, ovarian germ cell tumor, gestational trophoblastic tumor glioma, head and neck cancer, hepatocellular (liver) cancer, Hodgkin lymphoma, hypopharyngeal cancer, intraocular melanoma, ocular cancer, islet cell tumors (endocrine pancreas), Kaposi Sarcoma, kidney cancer, renal cancer, kidney cancer, laryngeal cancer, acute lymphoblastic leukemia, acute myeloid leukemia, chronic lymphocytic leukemia, chronic myelogenous leukemia, hairy cell leukemia, lip and oral cavity cancer, liver cancer, lung cancer, non-small cell lung cancer, small cell lung cancer, AIDS-related lymphoma, non-Hodgkin lymphoma, primary central nervous system lymphoma, Waldenstrom macroglobulinemia, melanoma, intraocular (eye) melanoma, merkel cell carcinoma, mesothelioma malignant, mesothelioma, metastatic squamous neck cancer, mouth cancer, cancer of the tongue, multiple endocrine neoplasia syndrome, mycosis fungoides, myelodysplastic syndromes, myelodysplastic/myeloproliferative diseases, chronic myelogenous leukemia, acute myeloid leukemia, multiple myeloma, chronic myeloproliferative disorders, nasopharyngeal cancer, neuroblastoma, oral cancer, oral cavity cancer, oropharyngeal cancer, ovarian cancer, ovarian epithelial cancer, ovarian low malignant potential tumor, pancreatic cancer, islet cell pancreatic cancer, paranasal sinus and nasal cavity cancer, parathyroid cancer, penile cancer, pharyngeal cancer, pheochromocytoma, pineoblastoma and supratentorial primitive neuroectodermal tumors, pituitary tumor, plasma cell neoplasm/multiple myeloma, pleuropulmonary blastoma, prostate cancer, rectal cancer, renal pelvis and ureter, transitional cell cancer, retinoblastoma, rhabdomyosarcoma, salivary gland cancer, ewing family of sarcoma tumors, Kaposi Sarcoma, soft tissue sarcoma, synovial sarcoma, uterine cancer, uterine sarcoma, skin cancer (non-melanoma), skin cancer (melanoma), merkel cell skin carcinoma, small intestine cancer, soft tissue sarcoma, squamous cell carcinoma, stomach (gastric) cancer, supratentorial primitive neuroectodermal tumors, testicular cancer, throat cancer, thymoma, thymoma and thymic carcinoma, thyroid cancer, transitional cell cancer of the renal pelvis and ureter and other urinary organs, gestational trophoblastic tumor, urethral cancer, endometrial uterine cancer, uterine sarcoma, uterine corpus cancer, vaginal cancer, vulvar cancer, and Wilm's Tumor.

A "cell proliferative disorder of the hematologic system" is a cell proliferative disorder involving cells of the hematologic system. A cell proliferative disorder of the hematologic system suitable for the strategies, treatment modalities, methods, combinations, and compositions provided herein can include lymphoma, leukemia, myeloid neoplasms, mast cell neoplasms, myelodysplasia, benign monoclonal gammopathy, lymphomatoid granulomatosis, lymphomatoid papulosis, polycythemia vera, chronic myelocytic leukemia, agnogenic myeloid metaplasia, and essential thrombocythemia. A cell proliferative disorder of the hematologic system can include hyperplasia, dysplasia, and metaplasia of cells of the hematologic system. In some embodiments, the strategies, treatment modalities, methods, combinations, and compositions provided herein are used to treat a cancer selected from the group consisting of a hematologic cancer of the disclosure or a hematologic cell proliferative disorder of the disclosure. A hematologic cancer of the disclosure can include multiple myeloma, lymphoma (including Hodgkin's lymphoma, non-Hodgkin's lymphoma, childhood lymphomas, and lymphomas of lymphocytic and cutaneous origin), leukemia (including childhood leukemia, hairy-cell leukemia, acute lymphocytic leukemia, acute myelocytic leukemia, chronic lymphocytic leukemia, chronic myelocytic leukemia, chronic myelogenous leukemia, and mast cell leukemia), myeloid neoplasms and mast cell neoplasms.

A "cell proliferative disorder of the lung" suitable for the strategies, treatment modalities, methods, combinations, and compositions provided herein includes a cell proliferative disorder involving cells of the lung. Cell proliferative disorders of the lung can include all forms of cell proliferative disorders affecting lung cells. Cell proliferative disorders of the lung can include lung cancer, a precancer or precancerous condition of the lung, benign growths or lesions of the lung, and malignant growths or lesions of the lung, and metastatic lesions in tissue and organs in the body other than the lung. Cell proliferative disorders of the lung can include hyperplasia, metaplasia, and dysplasia of the lung. In some embodiments, the strategies, treatment modalities, methods, combinations, and compositions provided herein are used to treat lung cancer or cell proliferative disorders of the lung. Lung cancer can include all forms of cancer of the lung. Lung cancer can include malignant lung neoplasms, carcinoma in situ, typical carcinoid tumors, and atypical carcinoid tumors. Lung cancer can include small cell lung cancer ("SCLC"), non-small cell lung cancer ("NSCLC"), squamous cell carcinoma, adenocarcinoma, small cell carcinoma, large cell carcinoma, adenosquamous cell carcinoma, and mesothelioma. Lung cancer can include "scar carcinoma," bronchioloalveolar carcinoma, giant cell carcinoma, spindle cell carcinoma, and large cell neuroendocrine carcinoma. Lung cancer can include lung neoplasms having histologic and ultrastructural heterogeneity (e.g., mixed cell types).

Cell proliferative disorders of the lung can also include asbestos-induced hyperplasia, squamous metaplasia, and benign reactive mesothelial metaplasia. Cell proliferative disorders of the lung can include replacement of columnar epithelium with stratified squamous epithelium, and mucosal dysplasia. Individuals exposed to inhaled injurious environmental agents such as cigarette smoke and asbestos may be at increased risk for developing cell proliferative disorders of the lung. Prior lung diseases that may predispose individuals to development of cell proliferative disorders of the lung can include chronic interstitial lung disease, necrotizing pulmonary disease, scleroderma, rheumatoid disease, sarcoidosis, interstitial pneumonitis, tuberculosis, repeated pneumonias, idiopathic pulmonary fibrosis, granulomata, asbestosis, fibrosing alveolitis, and Hodgkin's disease.

A "cell proliferative disorder of the colon" is a cell proliferative disorder involving cells of the colon. In some embodiments, the cell proliferative disorder of the colon is colon cancer. In some embodiments, the strategies, treatment modalities, methods, combinations, and compositions provided herein are used to treat colon cancer or cell proliferative disorders of the colon. Colon cancer can include all forms of cancer of the colon. Colon cancer can include sporadic and hereditary colon cancers. Colon cancer can include malignant colon neoplasms, carcinoma in situ, typical carcinoid tumors, and atypical carcinoid tumors. Colon cancer can include adenocarcinoma, squamous cell carcinoma, and adenosquamous cell carcinoma. Colon cancer can be associated with a hereditary syndrome selected from the group consisting of hereditary nonpolyposis colorectal cancer, familial adenomatous polyposis, Gardner's syndrome, Peutz-Jeghers syndrome, Turcot's syndrome and juvenile polyposis. Colon cancer can be caused by a hereditary syndrome selected from the group consisting of hereditary nonpolyposis colorectal cancer, familial adenomatous polyposis, Gardner's syndrome, Peutz-Jeghers syndrome, Turcot's syndrome and juvenile polyposis.

Cell proliferative disorders of the colon can include all forms of cell proliferative disorders affecting colon cells. Cell proliferative disorders of the colon can include colon cancer, precancerous conditions of the colon, adenomatous polyps of the colon and metachronous lesions of the colon. A cell proliferative disorder of the colon can include adenoma. Cell proliferative disorders of the colon can be characterized by hyperplasia, metaplasia, and dysplasia of the colon. Prior colon diseases that may predispose individuals to development of cell proliferative disorders of the colon can include prior colon cancer. Current disease that may predispose individuals to development of cell proliferative disorders of the colon can include Crohn's disease and ulcerative colitis. A cell proliferative disorder of the colon can be associated with a mutation in a gene selected from the group consisting of p53, ras, FAP and DCC. An individual can have an elevated risk of developing a cell proliferative disorder of the colon due to the presence of a mutation in a gene selected from the group consisting of p53, ras, FAP and DCC.

A "cell proliferative disorder of the pancreas" is a cell proliferative disorder involving cells of the pancreas. Cell proliferative disorders of the pancreas can include all forms of cell proliferative disorders affecting pancreatic cells. Cell proliferative disorders of the pancreas can include pancreas cancer, a precancer or precancerous condition of the pancreas, hyperplasia of the pancreas, and dysplasia of the pancreas, benign growths or lesions of the pancreas, and malignant growths or lesions of the pancreas, and metastatic lesions in tissue and organs in the body other than the pancreas. Pancreatic cancer includes all forms of cancer of the pancreas. Pancreatic cancer can include ductal adenocarcinoma, adenosquamous carcinoma, pleomorphic giant cell carcinoma, mucinous adenocarcinoma, osteoclast-like giant cell carcinoma, mucinous cystadenocarcinoma, acinar carcinoma, unclassified large cell carcinoma, small cell carcinoma, pancreatoblastoma, papillary neoplasm, mucinous cystadenoma, papillary cystic neoplasm, and serous cystadenoma. Pancreatic cancer can also include pancreatic neoplasms having histologic and ultrastructural heterogeneity (e.g., mixed cell types).

A "cell proliferative disorder of the prostate" is a cell proliferative disorder involving cells of the prostate. Cell proliferative disorders of the prostate can include all forms of cell proliferative disorders affecting prostate cells. Cell proliferative disorders of the prostate can include prostate cancer, a precancer or precancerous condition of the prostate, benign growths or lesions of the prostate, malignant growths or lesions of the prostate and metastatic lesions in tissue and organs in the body other than the prostate. Cell proliferative disorders of the prostate can include hyperplasia, metaplasia, and dysplasia of the prostate.

A "cell proliferative disorder of the skin" is a cell proliferative disorder involving cells of the skin. Cell proliferative disorders of the skin can include all forms of cell proliferative disorders affecting skin cells. Cell proliferative disorders of the skin can include a precancer or precancerous condition of the skin, benign growths or lesions of the skin, melanoma, malignant melanoma and other malignant growths or lesions of the skin, and metastatic lesions in tissue and organs in the body other than the skin. Cell proliferative disorders of the skin can include hyperplasia, metaplasia, and dysplasia of the skin.

A "cell proliferative disorder of the ovary" is a cell proliferative disorder involving cells of the ovary. Cell proliferative disorders of the ovary can include all forms of cell proliferative disorders affecting cells of the ovary. Cell proliferative disorders of the ovary can include a precancer or precancerous condition of the ovary, benign growths or lesions of the ovary, ovarian cancer, malignant growths or lesions of the ovary, and metastatic lesions in tissue and organs in the body other than the ovary. Cell proliferative disorders of the skin can include hyperplasia, metaplasia, and dysplasia of cells of the ovary.

A "cell proliferative disorder of the breast" is a cell proliferative disorder involving cells of the breast. Cell proliferative disorders of the breast can include all forms of cell proliferative disorders affecting breast cells. Cell proliferative disorders of the breast can include breast cancer, a precancer or precancerous condition of the breast, benign growths or lesions of the breast, and malignant growths or lesions of the breast, and metastatic lesions in tissue and organs in the body other than the breast. Cell proliferative disorders of the breast can include hyperplasia, metaplasia, and dysplasia of the breast.

A cell proliferative disorder of the breast can be a precancerous condition of the breast. In some embodiments, the strategies, treatment modalities, methods, combinations, and compositions provided herein are used to treat a precancerous condition of the breast. A precancerous condition of the breast can include atypical hyperplasia of the breast, ductal carcinoma in situ (DCIS), intraductal carcinoma, lobular carcinoma in situ (LCIS), lobular neoplasia, and stage 0 or grade 0 growth or lesion of the breast (e.g., stage 0 or grade 0 breast cancer, or carcinoma in situ). A precancerous condition of the breast can be staged according to the TNM classification scheme as accepted by the American Joint Committee on Cancer (AJCC), where the primary tumor (T) has been assigned a stage of T0 or Tis; and where the regional lymph nodes (N) have been assigned a stage of N0; and where distant metastasis (M) has been assigned a stage of M0.

The cell proliferative disorder of the breast can be breast cancer. Preferably, compositions of the disclosure may be used to treat breast cancer. Breast cancer includes all forms of cancer of the breast. Breast cancer can include primary epithelial breast cancers. Breast cancer can include cancers in which the breast is involved by other tumors such as lymphoma, sarcoma or melanoma. Breast cancer can include carcinoma of the breast, ductal carcinoma of the breast, lobular carcinoma of the breast, undifferentiated carcinoma of the breast, cystosarcoma phyllodes of the breast, angiosarcoma of the breast, and primary lymphoma of the breast. Breast cancer can include Stage I, II, IIIA, IIIB, IIIC and IV breast cancer. Ductal carcinoma of the breast can include invasive carcinoma, invasive carcinoma in situ with predominant intraductal component, inflammatory breast cancer, and a ductal carcinoma of the breast with a histologic type selected from the group consisting of comedo, mucinous (colloid), medullary, medullary with lymphocytic infiltrate, papillary, scirrhous, and tubular. Lobular carcinoma of the breast can include invasive lobular carcinoma with predominant in situ component, invasive lobular carcinoma, and infiltrating lobular carcinoma. Breast cancer can include Paget's disease, Paget's disease with intraductal carcinoma, and Paget's disease with invasive ductal carcinoma. Breast cancer can include breast neoplasms having histologic and ultrastructural heterogeneity (e.g., mixed cell types).

In some embodiments, the strategies, treatment modalities, methods, combinations, and compositions provided herein are used to treat breast cancer. A breast cancer that is to be treated can include familial breast cancer. A breast cancer that is to be treated can include sporadic breast cancer. A breast cancer that is to be treated can arise in a male subject. A breast cancer that is to be treated can arise in a female subject. A breast cancer that is to be treated can arise in a premenopausal female subject or a postmenopausal female subject. A breast cancer that is to be treated can arise in a subject equal to or older than 30 years old, or a subject younger than 30 years old. A breast cancer that is to be treated has arisen in a subject equal to or older than 50 years old, or a subject younger than 50 years old. A breast cancer that is to be treated can arise in a subject equal to or older than 70 years old, or a subject younger than 70 years old.

A breast cancer that is to be treated can be typed to identify a familial or spontaneous mutation in BRCA1, BRCA2, or p53. A breast cancer that is to be treated can be typed as having a HER2/neu gene amplification, as overexpressing HER2/neu, or as having a low, intermediate or high level of HER2/neu expression. A breast cancer that is to be treated can be typed for a marker selected from the group consisting of estrogen receptor (ER), progesterone receptor (PR), human epidermal growth factor receptor-2, Ki-67, CA15-3, CA 27-29, and c-Met. A breast cancer that is to be treated can be typed as ER-unknown, ER-rich or ER-poor. A breast cancer that is to be treated can be typed as ER-negative or ER-positive. ER-typing of a breast cancer may be performed by any reproducible means. ER-typing of a breast cancer may be performed as set forth in Onkologie 27: 175-179 (2004). A breast cancer that is to be treated can be typed as PR-unknown, PR-rich, or PR-poor. A breast cancer that is to be treated can be typed as PR-negative or PR-positive. A breast cancer that is to be treated can be typed as receptor positive or receptor negative. A breast cancer that is to be treated can be typed as being associated with elevated blood levels of CA 15-3, or CA 27-29, or both.

A breast cancer that is to be treated can include a localized tumor of the breast. A breast cancer that is to be treated can include a tumor of the breast that is associated with a negative sentinel lymph node (SLN) biopsy. A breast cancer that is to be treated can include a tumor of the breast that is associated with a positive sentinel lymph node (SLN) biopsy. A breast cancer that is to be treated can include a tumor of the breast that is associated with one or more positive axillary lymph nodes, where the axillary lymph nodes have been staged by any applicable method. A breast cancer that is to be treated can include a tumor of the breast that has been typed as having nodal negative status (e.g., node-negative) or nodal positive status (e.g., node-positive). A breast cancer that is to be treated can include a tumor of the breast that has metastasized to other locations in the body. A breast cancer that is to be treated can be classified as having metastasized to a location selected from the group consisting of bone, lung, liver, or brain. A breast cancer that is to be treated can be classified according to a characteristic selected from the group consisting of metastatic, localized, regional, local-regional, locally advanced, distant, multicentric, bilateral, ipsilateral, contralateral, newly diagnosed, recurrent, and inoperable.

In some embodiments, the strategies, treatment modalities, methods, combinations, and compositions provided herein are used to treat or prevent a cell proliferative disorder of the breast, or to treat or prevent breast cancer, in a subject having an increased risk of developing breast cancer relative to the population at large. A subject with an increased risk of developing breast cancer relative to the population at large is a female subject with a family history or personal history of breast cancer. A subject with an increased risk of developing breast cancer relative to the population at large is a female subject having a germ-line or spontaneous mutation in BRCA1 or BRCA2, or both. A subject with an increased risk of developing breast cancer relative to the population at large is a female subject with a family history of breast cancer and a germ-line or spontaneous mutation in BRCA1 or BRCA2, or both. A subject with an increased risk of developing breast cancer relative to the population at large is a female who is greater than 30 years old, greater than 40 years old, greater than 50 years old, greater than 60 years old, greater than 70 years old, greater than 80 years old, or greater than 90 years old. A subject with an increased risk of developing breast cancer relative to the population at large is a subject with atypical hyperplasia of the breast, ductal carcinoma in situ (DCIS), intraductal carcinoma, lobular carcinoma in situ (LCIS), lobular neoplasia, or a stage 0 growth or lesion of the breast (e.g., stage 0 or grade 0 breast cancer, or carcinoma in situ).

A breast cancer that is to be treated can be histologically graded according to the Scarff-Bloom-Richardson system, wherein a breast tumor has been assigned a mitosis count score of 1, 2, or 3; a nuclear pleomorphism score of 1, 2, or 3; a tubule formation score of 1, 2, or 3; and a total Scarff-Bloom-Richardson score of between 3 and 9. A breast cancer that is to be treated can be assigned a tumor grade according to the International Consensus Panel on the Treatment of Breast Cancer selected from the group consisting of grade 1, grade 1-2, grade 2, grade 2-3, or grade 3.

A cancer that is to be treated can be staged according to the American Joint Committee on Cancer (AJCC) TNM classification system, where the tumor (T) has been assigned a stage of TX, $T_1$, T1mic, T1a, T1b, T1c, T2, T3, T4, T4a, T4b, T4c, or T4d; and where the regional lymph nodes (N) have been assigned a stage of NX, N0, N1, N2, N2a, N2b, N3, N3a, N3b, or N3c; and where distant metastasis (M) can be assigned a stage of MX, M0, or M1. A cancer that is to be treated can be staged according to an American Joint Committee on Cancer (AJCC) classification as Stage I, Stage IIA, Stage IIB, Stage IIIA, Stage IIIB, Stage IIIC, or Stage IV. A cancer that is to be treated can be assigned a grade according to an AJCC classification as Grade GX (e.g., grade cannot be assessed), Grade 1, Grade 2, Grade 3 or Grade 4. A cancer that is to be treated can be staged according to an AJCC pathologic classification (pN) of pNX, pN0, PN0 (I−), PN0 (I+), PN0 (mol−), PN0 (mol+), PN1, PN1 (mi), PN1a, PN1b, PN1c, pN2, pN2a, pN2b, pN3, pN3a, pN3b, or pN3c.

A cancer that is to be treated can include a tumor that has been determined to be less than or equal to about 2 centimeters in diameter. A cancer that is to be treated can include a tumor that has been determined to be from about 2 to about 5 centimeters in diameter. A cancer that is to be treated can include a tumor that has been determined to be greater than or equal to about 3 centimeters in diameter. A cancer that is to be treated can include a tumor that has been determined to be greater than 5 centimeters in diameter. A cancer that is to be treated can be classified by microscopic appearance as well differentiated, moderately differentiated, poorly differentiated, or undifferentiated. A cancer that is to be treated can be classified by microscopic appearance with respect to mitosis count (e.g., amount of cell division) or nuclear pleomorphism (e.g., change in cells). A cancer that is to be treated can be classified by microscopic appearance as being associated with areas of necrosis (e.g., areas of dying or degenerating cells). A cancer that is to be treated can be classified as having an abnormal karyotype, having an abnormal number of chromosomes, or having one or more chromosomes that are abnormal in appearance. A cancer that is to be treated can be classified as being aneuploid, triploid, tetraploid, or as having an altered ploidy. A cancer that is to be treated can be classified as having a chromosomal translocation, or a deletion or duplication of an entire chromosome, or a region of deletion, duplication or amplification of a portion of a chromosome.

A cancer that is to be treated can be evaluated by DNA cytometry, flow cytometry, or image cytometry. A cancer that is to be treated can be typed as having 10%, 20%, 30%, 40%, 50%, 60%, 70%, 80%, or 90% of cells in the synthesis stage of cell division (e.g., in S phase of cell division). A cancer that is to be treated can be typed as having a low S-phase fraction or a high S-phase fraction.

Any other disease in which epigenetic methylation, which is mediated by EZH2, plays a role may be treatable or preventable using compositions and methods described herein.

Treating cancer can result in a reduction in size of a tumor. A reduction in size of a tumor may also be referred to as "tumor regression". Preferably, after treatment with the strategies, treatment modalities, methods, combinations, and compositions provided herein, tumor size is reduced by 5% or greater relative to its size prior to treatment; more preferably, tumor size is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Size of a tumor may be measured by any reproducible means of measurement. The size of a tumor may be measured as a diameter of the tumor.

Treating cancer can result in a reduction in tumor volume. Preferably, after treatment with the strategies, treatment modalities, methods, combinations, and compositions provided herein, tumor volume is reduced by 5% or greater relative to its size prior to treatment; more preferably, tumor volume is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Tumor volume may be measured by any reproducible means of measurement.

In some embodiments, treating cancer results in a decrease in the number of tumors. Preferably, after treatment with the strategies, treatment modalities, methods, combinations, and compositions provided herein, tumor number is reduced by 5% or greater relative to number prior to treatment; more preferably, tumor number is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. Number of tumors may be measured by any reproducible means of measurement. The number of tumors may be measured by counting tumors visible to the naked eye or at a specified magnification. Preferably, the specified magnification is 2×, 3×, 4×, 5×, 10×, or 50×.

Treating cancer can result in a decrease in number of metastatic lesions in other tissues or organs distant from the primary tumor site. Preferably, after treatment with the strategies, treatment modalities, methods, combinations, and compositions provided herein, the number of metastatic lesions is reduced by 5% or greater relative to number prior to treatment; more preferably, the number of metastatic lesions is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. The number of metastatic lesions may be measured by any reproducible means of measurement. The number of metastatic lesions may be measured by counting metastatic lesions visible to the naked eye or at a specified magnification. Preferably, the specified magnification is 2×, 3×, 4×, 5×, 10×, or 50×.

Treating cancer can result in an increase in average survival time of a population of treated subjects in comparison to a population receiving carrier alone. Preferably, after treatment with the strategies, treatment modalities, methods, combinations, and compositions provided herein, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in an increase in average survival time of a population of treated subjects in comparison to a population of untreated subjects. Preferably, after treatment with the strategies, treatment modalities, methods, combinations, and compositions provided herein, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in increase in average survival time of a population of treated subjects in comparison to a population receiving monotherapy with a drug that is not a compound of the disclosure, or a pharmaceutically acceptable salt, solvate, analog or derivative thereof. Preferably, after treatment with the strategies, treatment modalities, methods, combinations, and compositions provided herein, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in a decrease in the mortality rate of a population of treated subjects in comparison to a population receiving carrier alone. Treating cancer can result in a decrease in the mortality rate of a population of treated subjects in comparison to an untreated population. Treating cancer can result in a decrease in the mortality rate of a population of treated subjects in comparison to a population receiving monotherapy with a drug that is not a compound of the disclosure, or a pharmaceutically acceptable salt, solvate, analog or derivative thereof. Preferably, after treatment with the strategies, treatment modalities, methods, combinations, and compositions provided herein, the mortality rate is decreased by more than 2%; more preferably, by more than 5%; more preferably, by more than 10%; and most preferably, by more than 25%. A decrease in the mortality rate of a population of treated subjects may be measured by any reproducible means. A decrease in the mortality rate of a population may be measured, for example, by calculating for a population the average number of disease-related deaths per unit time following initiation of treatment with an active compound. A decrease in the mortality rate of a population may also be measured, for example, by calculating for a population the average number of disease-related deaths per unit time following completion of a first round of treatment with an active compound.

Treating cancer can result in a decrease in tumor growth rate. Preferably, after treatment with the strategies, treatment modalities, methods, combinations, and compositions provided herein, after treatment, tumor growth rate is reduced by at least 5% relative to number prior to treatment; more preferably, tumor growth rate is reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Tumor growth rate may be measured by any reproducible means of measurement. Tumor growth rate can be measured according to a change in tumor diameter per unit time.

Treating cancer can result in a decrease in tumor regrowth. Preferably, after treatment with the strategies, treatment modalities, methods, combinations, and compositions provided herein, after treatment, tumor regrowth is less than 5%; more preferably, tumor regrowth is less than 10%; more preferably, less than 20%; more preferably, less than 30%; more preferably, less than 40%; more preferably, less than 50%; even more preferably, less than 50%; and most preferably, less than 75%. Tumor regrowth may be measured by any reproducible means of measurement. Tumor regrowth is measured, for example, by measuring an increase in the diameter of a tumor after a prior tumor shrinkage that followed treatment. A decrease in tumor regrowth is indicated by failure of tumors to reoccur after treatment has stopped.

Treating or preventing a cell proliferative disorder can result in a reduction in the rate of cellular proliferation. Preferably, after treatment with the strategies, treatment modalities, methods, combinations, and compositions provided herein, after treatment, the rate of cellular proliferation is reduced by at least 5%; more preferably, by at least 10%; more preferably, by at least 20%; more preferably, by at least 30%; more preferably, by at least 40%; more preferably, by at least 50%; even more preferably, by at least 50%; and most preferably, by at least 75%. The rate of cellular proliferation may be measured by any reproducible means of measurement. The rate of cellular proliferation is measured, for example, by measuring the number of dividing cells in a tissue sample per unit time.

Treating or preventing a cell proliferative disorder can result in a reduction in the proportion of proliferating cells. Preferably, after treatment with the strategies, treatment modalities, methods, combinations, and compositions provided herein, after treatment, the proportion of proliferating cells is reduced by at least 5%; more preferably, by at least 10%; more preferably, by at least 20%; more preferably, by at least 30%; more preferably, by at least 40%; more preferably, by at least 50%; even more preferably, by at least 50%; and most preferably, by at least 75%. The proportion of proliferating cells may be measured by any reproducible means of measurement. Preferably, the proportion of proliferating cells is measured, for example, by quantifying the number of dividing cells relative to the number of nondividing cells in a tissue sample. The proportion of proliferating cells can be equivalent to the mitotic index.

Treating or preventing a cell proliferative disorder can result in a decrease in size of an area or zone of cellular proliferation. Preferably, after treatment with the strategies, treatment modalities, methods, combinations, and compositions provided herein, after treatment, size of an area or zone of cellular proliferation is reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Size of an area or zone of cellular proliferation may be measured by any reproducible means of measurement. The size of an area or zone of cellular proliferation may be measured as a diameter or width of an area or zone of cellular proliferation.

Treating or preventing a cell proliferative disorder can result in a decrease in the number or proportion of cells having an abnormal appearance or morphology. Preferably, after treatment with the strategies, treatment modalities, methods, combinations, and compositions provided herein, after treatment, the number of cells having an abnormal morphology is reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. An abnormal cellular appearance or morphology may be measured by any reproducible means of measurement. An abnormal cellular morphology can be measured by microscopy, e.g., using an inverted tissue culture microscope. An abnormal cellular morphology can take the form of nuclear pleomorphism.

As used herein, the term "selectively" means tending to occur at a higher frequency in one population than in another population. The compared populations can be cell populations. Preferably, a compound of the disclosure, or a pharmaceutically acceptable salt or solvate thereof, acts selectively on a cancer or precancerous cell but not on a normal cell. Preferably, a compound of the disclosure, or a pharmaceutically acceptable salt or solvate thereof, acts selectively to modulate one molecular target (e.g., a target protein methyltransferase) but does not significantly modulate another molecular target (e.g., a non-target protein methyltransferase). The disclosure also provides a method for selectively inhibiting the activity of an enzyme, such as a protein methyltransferase. Preferably, an event occurs selectively in population A relative to population B if it occurs greater than two times more frequently in population A as compared to population B. An event occurs selectively if it occurs greater than five times more frequently in population A. An event occurs selectively if it occurs greater than ten times more frequently in population A; more preferably, greater than fifty times; even more preferably, greater than 100 times; and most preferably, greater than 1000 times more frequently in population A as compared to population B. For example, cell death would be said to occur selectively in cancer cells if it occurred greater than twice as frequently in cancer cells as compared to normal cells.

A composition of the disclosure, e.g., a composition comprising an EZH2 inhibitor of the disclosure can modulate the activity of a molecular target (e.g., a target protein methyltransferase). A composition of the disclosure, e.g., a composition comprising an immune checkpoint inhibitor of the disclosure can modulate the activity of a molecular target (e.g., a checkpoint protein in an immune cell or progenitor thereof). Modulating refers to stimulating or inhibiting an activity of a molecular target. Preferably, a compound of the disclosure, or a pharmaceutically acceptable salt or solvate thereof, modulates the activity of a molecular target if it stimulates or inhibits the activity of the molecular target by at least 2-fold relative to the activity of the molecular target under the same conditions but lacking only the presence of said compound. More preferably, a compound of the disclosure, or a pharmaceutically acceptable salt or solvate thereof, modulates the activity of a molecular target if it stimulates or inhibits the activity of the molecular target by at least 5-fold, at least 10-fold, at least 20-fold, at least 50-fold, at least 100-fold relative to the activity of the molecular target under the same conditions but lacking only the presence of said compound. The activity of a molecular target may be measured by any reproducible means. The activity of a molecular target may be measured in vitro or in vivo. For example, the activity of a molecular target may be measured in vitro by an enzymatic activity assay or a DNA binding assay, or the activity of a molecular target may be measured in vivo by assaying for expression of a reporter gene.

A composition of the disclosure does not significantly modulate the activity of a molecular target if the addition of the compound does not stimulate or inhibit the activity of the molecular target by greater than 10% relative to the activity of the molecular target under the same conditions but lacking only the presence of said compound.

As used herein, the term "isozyme selective" means preferential inhibition or stimulation of a first isoform of an enzyme in comparison to a second isoform of an enzyme (e.g., preferential inhibition or stimulation of a protein methyltransferase isozyme alpha in comparison to a protein methyltransferase isozyme beta). Preferably, a compound of the disclosure, or a pharmaceutically acceptable salt or solvate thereof, demonstrates a minimum of a fourfold differential, preferably a tenfold differential, more preferably a fifty fold differential, in the dosage required to achieve a biological effect. Preferably, a compound of the disclosure, or a pharmaceutically acceptable salt or solvate thereof, demonstrates this differential across the range of inhibition, and the differential is exemplified at the $IC_{50}$, i.e., a 50% inhibition, for a molecular target of interest.

Administering a compound of the disclosure, e.g., a composition comprising an EZH2 inhibitor, and one or more other therapeutic agents, to a cell or a subject in need thereof results in modulation (i.e., stimulation or inhibition) of an activity of an intracellular target (e.g., substrate). Several intracellular targets can be modulated with the compounds of the disclosure, including, but not limited to, protein methyltransferase.

Treating cancer or a cell proliferative disorder can result in cell death, and preferably, cell death results in a decrease of at least 10% in number of cells in a population. More preferably, cell death means a decrease of at least 20%; more preferably, a decrease of at least 30%; more preferably, a decrease of at least 40%; more preferably, a decrease of at least 50%; most preferably, a decrease of at least 75%. Number of cells in a population may be measured by any reproducible means. A number of cells in a population can be measured by fluorescence activated cell sorting (FACS), immunofluorescence microscopy and light microscopy. Methods of measuring cell death are as shown in Li et al., *Proc Natl Acad Sci USA.* 100(5): 2674-8, 2003. In an aspect, cell death occurs by apoptosis.

Preferably, the strategies, treatment modalities, methods, combinations, and compositions provided herein result in is no significantly cytotoxicity to normal cells. A therapeutically effective amount of an EZH2 inhibitor and/or an immune checkpoint inhibitor is not significantly cytotoxic to normal cells if administration of the compound in a therapeutically effective amount does not induce cell death in greater than 10% of normal cells. A therapeutically effective amount of an EZH2 inhibitor and/or an immune checkpoint inhibitor does not significantly affect the viability of normal cells if administration in a therapeutically effective amount does not induce cell death in greater than 10% of normal cells. In some embodiments, cell death occurs by apoptosis.

Contacting a cell with an EZH2 inhibitor and/or an immune checkpoint inhibitor, can induce or activate cell death selectively in cancer cells. Administering to a subject in need thereof an EZH2 inhibitor and/or an immune checkpoint inhibitor, can induce or activate cell death selectively in cancer cells. Contacting a cell with an EZH2 inhibitor and/or an immune checkpoint inhibitor, can induce cell death selectively in one or more cells affected by a cell proliferative disorder. Preferably, administering to a subject in need thereof an EZH2 inhibitor and/or an immune checkpoint inhibitor, induces cell death selectively in one or more cells affected by a cell proliferative disorder.

In some aspects, the disclosure relates to a method of treating or preventing cancer by administering an EZH2 inhibitor and/or an immune checkpoint inhibitor, to a subject in need thereof, where the administering results in one or more of the following: prevention of cancer cell proliferation by accumulation of cells in one or more phases of the cell cycle (e.g. G1, G1/S, G2/M), or induction of cell senescence, or promotion of tumor cell differentiation; promotion of cell death in cancer cells via cytotoxicity, necrosis or apoptosis, without a significant amount of cell death in normal cells, antitumor activity in animals with a therapeutic index of at least 2. As used herein, "therapeutic index" is the maximum tolerated dose divided by the efficacious dose.

One skilled in the art may refer to general reference texts for detailed descriptions of known techniques discussed herein or equivalent techniques. These texts include Ausubel et al., *Current Protocols in Molecular Biology*, John Wiley and Sons, Inc. (2005); Sambrook et al., *Molecular Cloning, A Laboratory Manual* ($3^{rd}$ edition), Cold Spring Harbor Press, Cold Spring Harbor, N.Y. (2000); Coligan et al., *Current Protocols in Immunology*, John Wiley & Sons, N.Y.; Enna et al., *Current Protocols in Pharmacology*, John Wiley & Sons, N.Y.; Fingl et al., *The Pharmacological Basis of Therapeutics* (1975), *Remington's Pharmaceutical Sciences*, Mack Publishing Co., Easton, Pa., $18^{th}$ edition (1990). These texts can, of course, also be referred to in making or using an aspect of the disclosure.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

The invention can be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

EXAMPLES

Example 1: Combination Therapy with Tazemetostat and Atezolizumab

A first subject diagnosed with locally advanced or metastatic urothelial carcinoma is treated with a combination of tazemetostat at an oral dose of 800 mg twice per day and atezolizumab (TECENTRIQ™) at a dose of 1200 mg as an intravenous infusion over 60 minutes every 3 weeks (see, accessdata.fda.gov/drugsatfda_docs/label/2016/ 761034s0001b1.pdf, the contents of which are incorporated herein for additional information about atezolizumab).

A second subject diagnosed with Diffuse Large B-Cell Lymphoma (DLBCL) is treated with a combination of tazemetostat at an oral dose of 800 mg twice per day and atezolizumab (TECENTRIQ™) at a dose of 1200 mg as an intravenous infusion over 60 minutes every 3 weeks.

A third subject diagnosed with Non-Hodgkin's Lymphoma is treated with a combination of tazemetostat at an oral dose of 800 mg twice per day and atezolizumab (TECENTRIQ™) at a dose of 1200 mg as an intravenous infusion over 60 minutes every 3 weeks.

Example 2: Combination Therapy with Tazemetostat and Nivolumab

A first subject diagnosed with melanoma is treated with a combination of tazemetostat at an oral dose of 800 mg twice per day and nivolumab (OPTIVO™) at a dose of 3 mg/kg as an intravenous infusion over 60 minutes every 2 weeks (see, accessdata.fda.gov/drugsatfda_docs/label/2014/ 125554lb1.pdf, the contents of which are incorporated herein for additional information about nivolumab).

A second subject, having a BRAF V600 mutation and diagnosed with melanoma, or another form of cancer, is treated with a combination of tazemetostat at an oral dose of 800 mg twice per day and nivolumab (OPTIVO™) at a dose of 3 mg/kg as an intravenous infusion over 60 minutes every 2 weeks, and further treated with a BRAF inhibitor.

Example 3: Combination Therapy with Tazemetostat and Pembrolizumab

A first subject diagnosed with melanoma and disease progression following ipilimumab, or another form of cancer is treated with a combination of tazemetostat at an oral dose of 800 mg twice per day and pembrolizumab (KEYTRUDA™) at a dose of 2 mg/kg as an intravenous infusion over 30 minutes every 3 weeks (see, accessdata.fda.gov/drugsatfda_docs/label/2014/125514lb1.pdf, the contents of which are incorporated herein for additional information about pembrolizumab).

A second subject has the BRAF V600 mutation and is diagnosed with unresectable or metastatic melanoma and disease progression following ipilimumab, or another form of cancer is treated with a combination of tazemetostat at an oral dose of 800 mg/kg twice per day and pembrolizumab (KEYTRUDA™) at a dose of 2 mg/kg as an intravenous infusion over 30 minutes every 3 weeks, and further treated with a BRAF inhibitor.

We claim:
1. A method for treating breast cancer, nervous system cancer, colorectal cancer, cervical cancer, or brain cancer in a subject, wherein the breast cancer, nervous system cancer, colorectal cancer, cervical cancer, or brain cancer is resistant to treatment with pembrolizumab as a monotherapy and wherein the breast cancer, nervous system cancer, colorectal cancer, cervical cancer, or brain cancer is resistant to treatment with the compound of Formula (IIa) or a pharmaceutically acceptable salt thereof, as a monotherapy, the method comprising administering to the subject:
(a) a compound of Formula (IIa) or a pharmaceutically acceptable salt thereof:

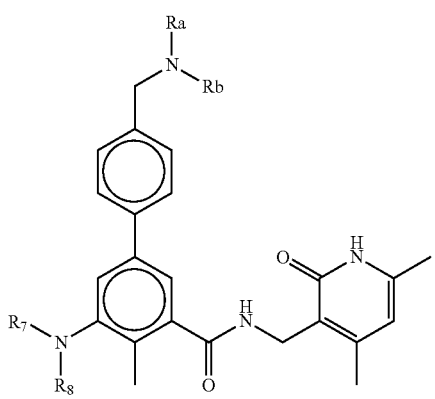

(IIa)

each of $R_a$ and $R_b$, independently is H or $R_{S3}$, $R_{S3}$ being $C_1$-$C_6$ alkyl, $C_3$-$C_8$ cycloalkyl, $C_6$-$C_{10}$ aryl, 4 to 12-membered heterocycloalkyl, or 5- or 6-membered heteroaryl, or $R_a$ and $R_b$, together with the N atom to which they are attached, form a 4 to 12-membered heterocycloalkyl ring having 0 or 1 additional heteroatom, and each of $R_{S3}$ and the 4 to 12-membered heterocycloalkyl ring formed by $R_a$ and $R_b$, is optionally substituted with one or more -$Q_3$-$T_3$, wherein $Q_3$ is a bond or $C_1$-$C_3$ alkyl linker each optionally substituted with halo, cyano, hydroxyl or $C_1$-$C_6$ alkoxy, and T3 is selected from the group consisting of halo, cyano, $C_1$-$C_6$ alkyl, $C_3$-$C_8$ cycloalkyl, $C_6$-$C_{10}$ aryl, 4 to 12-membered heterocycloalkyl, 5- or 6-membered heteroaryl, $OR_d$, $COOR_d$, —$S(O)_2R_d$, —$NR_dR_e$, and —$C(O)NR_dR_e$, each of $R_d$ and $R_e$ independently being H or $C_1$-$C_6$ alkyl, or -$Q_3$-$T_3$ is oxo;
$R_7$ is -$Q_4$-$T_4$, in which $Q_4$ is a bond, $C_1$-$C_4$ alkyl linker, or $C_2$-$C_4$ alkenyl linker, each linker optionally substituted with halo, cyano, hydroxyl or $C_1$-$C_6$ alkoxy, and $T_4$ is H, halo, cyano, $NR_fR_g$, —$OR_f$, —$C(O)R_f$, —$C(O)OR_f$, —$C(O)NR_fR_g$, —$C(O)NR_fOR_g$, —$NR_fC(O)R_g$, —$S(O)_2R_f$, or $R_{S4}$, in which each of $R_f$ and $R_g$, independently is H or $R_{S5}$, each of $R_{S4}$ and $R_{S5}$, independently is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 7-membered heterocycloalkyl, or 5- or 6-membered heteroaryl, and each of $R_{S4}$ and $R_{S5}$ is optionally substituted with one or more -$Q_5$-$T_5$, wherein $Q_5$ is a bond, C(O), C(O)$NR_k$, $NR_kC(O)$, $S(O)_2$, or $C_1$-$C_3$ alkyl linker, $R_k$ being H or $C_1$-$C_6$ alkyl, and $T_5$ is H, halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 7-membered heterocycloalkyl, 5- or 6-membered heteroaryl, or $S(O)_qR_q$ in which q is 0, 1, or 2 and $R_q$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 7-membered heterocycloalkyl, or 5- or 6-membered heteroaryl, and $T_5$ is optionally substituted with one or more substituents selected from the group consisting of halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 7-membered heterocycloalkyl, and 5- or 6-membered heteroaryl except when $T_5$ is H, halo, hydroxyl, or cyano; or -$Q_5$-$T_5$ is oxo; provided that $R_7$ is not H; and
$R_8$ is H, halo, hydroxyl, COOH, cyano, $R_{S6}$, $OR_{S6}$, or $COOR_{S6}$, in which $R_{S6}$ is $C_1$-$C_6$ alkyl, $C_2$-$C_6$ alkenyl, $C_2$-$C_6$ alkynyl, amino, mono-$C_1$-$C_6$ alkylamino, or di-$C_1$-$C_6$ alkylamino, and $R_{S6}$ is optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, and di-$C_1$-$C_6$ alkylamino; or $R_7$ and $R_8$, together with the N atom to which they are attached, form a 4 to 11-membered heterocycloalkyl ring which has 0 to 2 additional heteroatoms and is optionally substituted with one or more -$Q_6$-$T_6$, wherein $Q_6$ is a bond, C(O), C(O)$NR_m$, $NR_mC(O)$, $S(O)_2$, or $C_1$-$C_3$ alkyl linker, $R_m$ being H or $C_1$-$C_6$ alkyl, and $T_6$ is H, halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 7-membered heterocycloalkyl, 5- or 6-membered heteroaryl, or $S(O)_pR_p$ in which p is 0, 1, or 2 and $R_p$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 7-membered heterocycloalkyl, or 5- or 6-membered heteroaryl, and $T_6$ is optionally substituted with one or more substituents selected from the group consisting of halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 7-membered heterocycloalkyl, and 5- or 6-membered heteroaryl except when $T_6$ is H, halo, hydroxyl, or cyano; or -$Q_6$-$T_6$ is oxo; and
(b) pembrolizumab.
2. A method for treating breast cancer, nervous system cancer, colorectal cancer, cervical cancer, or brain cancer in a subject comprising administering to the subject a compound of Formula (IIa) or a pharmaceutically acceptable salt thereof:

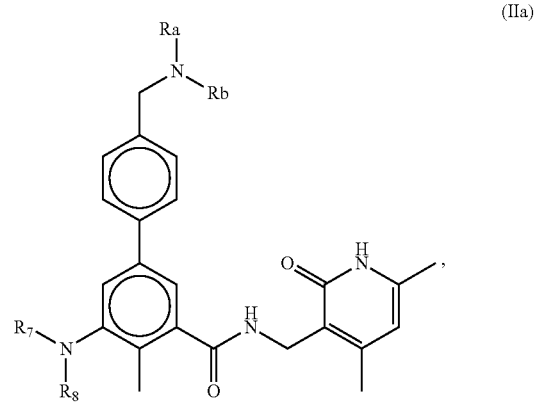

(IIa)

each of $R_a$ and $R_b$, independently is H or $R_{S3}$, $R_{S3}$ being $C_1$-$C_6$ alkyl, $C_3$-$C_8$ cycloalkyl, $C_6$-$C_{10}$ aryl, 4 to 12-membered heterocycloalkyl, or 5- or 6-membered heteroaryl, or $R_a$ and $R_b$, together with the N atom to which they are attached, form a 4 to 12-membered heterocycloalkyl ring having 0 or 1 additional heteroatom, and each of $R_{S3}$ and the 4 to 12-membered heterocycloalkyl ring formed by $R_a$ and $R_b$, is optionally substituted with one or more -$Q_3$-$T_3$, wherein $Q_3$ is a bond or $C_1$-$C_3$ alkyl linker each optionally substituted with halo, cyano, hydroxyl or $C_1$-$C_6$ alkoxy, and $T_3$ is selected from the group consisting of halo, cyano, $C_1$-$C_6$ alkyl, $C_3$-$C_8$ cycloalkyl, $C_6$-$C_{10}$ aryl, 4 to 12-membered heterocycloalkyl, 5- or 6-membered heteroaryl, $OR_d$, $COOR_d$, —$S(O)_2R_d$, —$NR_dR_e$, and —$C(O)NR_dR_e$, each of $R_d$ and $R_e$ independently being H or $C_1$-$C_6$ alkyl, or -$Q_3$-$T_3$ is oxo;

$R_7$ is -$Q_4$-$T_4$, in which $Q_4$ is a bond, $C_1$-$C_4$ alkyl linker, or $C_2$-$C_4$ alkenyl linker, each linker optionally substituted with halo, cyano, hydroxyl or $C_1$-$C_6$ alkoxy, and $T_4$ is H, halo, cyano, $NR_fR_g$, —$OR_f$, —$C(O)R_f$, —$C(O)OR_f$, —$C(O)NR_fR_g$, —$C(O)NR_fOR_g$, —$NR_fC(O)R_g$, —$S(O)_2R_f$, or $R_{S4}$, in which each of $R_f$ and $R_g$, independently is H or $R_{S5}$, each of $R_{S4}$ and $R_{S5}$, independently is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 7-membered heterocycloalkyl, or 5- or 6-membered heteroaryl, and each of $R_{S4}$ and $R_{S5}$ is optionally substituted with one or more -$Q_5$-$T_5$, wherein $Q_5$ is a bond, C(O), C(O)$NR_k$, $NR_kC(O)$, $S(O)_2$, or $C_1$-$C_3$ alkyl linker, $R_k$ being H or $C_1$-$C_6$ alkyl, and $T_5$ is H, halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 7-membered heterocycloalkyl, 5- or 6-membered heteroaryl, or $S(O)_qR_q$ in which q is 0, 1, or 2 and $R_q$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 7-membered heterocycloalkyl, or 5- or 6-membered heteroaryl, and $T_5$ is optionally substituted with one or more substituents selected from the group consisting of halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 7-membered heterocycloalkyl, and 5- or 6-membered heteroaryl except when $T_5$ is H, halo, hydroxyl, or cyano; or -$Q_5$-$T_5$ is oxo; provided that $R_7$ is not H; and $R_8$ is H, halo, hydroxyl, COOH, cyano, $R_{S6}$, $OR_{S6}$, or $COOR_{S6}$, in which $R_{S6}$ is $C_1$-$C_6$ alkyl, $C_2$-$C_6$ alkenyl, $C_2$-$C_6$ alkynyl, amino, mono-$C_1$-$C_6$ alkylamino, or di-$C_1$-$C_6$ alkylamino, and $R_{S6}$ is optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, and di-$C_1$-$C_6$ alkylamino; or $R_7$ and $R_8$, together with the N atom to which they are attached, form a 4 to 11-membered heterocycloalkyl ring which has 0 to 2 additional heteroatoms and is optionally substituted with one or more -$Q_6$-$T_6$, wherein $Q_6$ is a bond, C(O), C(O)$NR_m$, $NR_mC(O)$, $S(O)_2$, or $C_1$-$C_3$ alkyl linker, $R_m$ being H or $C_1$-$C_6$ alkyl, and $T_6$ is H, halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 7-membered heterocycloalkyl, 5- or $S(O)_pR_p$ in which p is 0, 1, or 2 and $R_p$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 7-membered heterocycloalkyl, or 5- or 6-membered heteroaryl, and $T_6$ is optionally substituted with one or more substituents selected from the group consisting of halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 7-membered heterocycloalkyl, and 5- or 6-membered heteroaryl except when $T_6$ is H, halo, hydroxyl, or cyano; or -$Q_6$-$T_6$ is oxo, wherein the subject has been receiving and will continue to receive pembrolizumab, wherein the breast cancer, nervous system cancer, colorectal cancer, cervical cancer, or brain cancer is resistant to treatment with pembrolizumab as a monotherapy and wherein the breast cancer, nervous system cancer, colorectal cancer, cervical cancer, or brain cancer is resistant to treatment with the compound of Formula (IIa) or a pharmaceutically acceptable salt thereof, as a monotherapy.

3. A method for treating breast cancer, nervous system cancer, colorectal cancer, cervical cancer, or brain cancer in a subject-comprising administering to the subject pembrolizumab, wherein the subject has been receiving and will continue to receive a compound of Formula (IIa) or a pharmaceutically acceptable salt thereof, wherein the breast cancer, nervous system cancer, colorectal cancer, cervical cancer, or brain cancer is resistant to treatment with pembrolizumab as a monotherapy and wherein the breast cancer, nervous system cancer, colorectal cancer, cervical cancer, or brain cancer is resistant to treatment with the compound of Formula (IIa) or a pharmaceutically acceptable salt thereof, as a monotherapy:

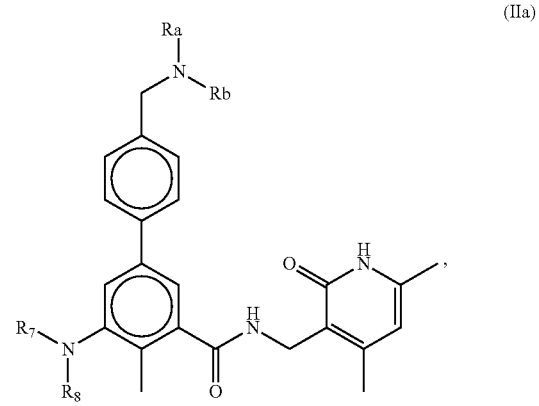

(IIa)

each of $R_a$ and $R_b$, independently is H or $R_{S3}$, $R_{S3}$ being $C_1$-$C_6$ alkyl, $C_3$-$C_8$ cycloalkyl, $C_6$-$C_{10}$ aryl, 4 to 12-membered heterocycloalkyl, or 5- or 6-membered heteroaryl, or $R_a$ and $R_b$, together with the N atom to which they are attached, form a 4 to 12-membered heterocycloalkyl ring having 0 or 1 additional heteroatom, and each of $R_{S3}$ and the 4 to 12-membered heterocycloalkyl ring formed by $R_a$ and $R_b$, is optionally substituted with one or more -$Q_3$-$T_3$, wherein $Q_3$ is a bond or $C_1$-$C_3$ alkyl linker each optionally substituted with halo, cyano, hydroxyl or $C_1$-$C_6$ alkoxy, and $T_3$ is selected from the group consisting of halo, cyano, $C_1$-$C_6$ alkyl, $C_3$-$C_8$ cycloalkyl, $C_6$-$C_{10}$ aryl, 4 to 12-membered heterocycloalkyl, 5- or 6-membered heteroaryl, $OR_d$, $COOR_d$, —$S(O)_2R_d$, —$NR_dR_e$, and —$C(O)NR_dR_e$, each of $R_d$ and $R_e$ independently being H or $C_1$-$C_6$ alkyl, or -$Q_3$-$T_3$ is oxo;

R₇ is -Q₄-T₄, in which Q₄ is a bond, C₁-C₄ alkyl linker, or C₂-C₄ alkenyl linker, each linker optionally substituted with halo, cyano, hydroxyl or C₁-C₆ alkoxy, and T₄ is H, halo, cyano, NR$_f$R$_g$, —OR$_f$, —C(O)R$_f$, —C(O)OR$_f$, —C(O)NR$_f$R$_g$, —C(O)NR$_f$OR$_g$, —NR$_f$C(O)R$_g$, —S(O)₂R$_f$, or R$_{S4}$, in which each of R$_f$ and R$_g$, independently is H or R$_{S5}$, each of R$_{S4}$ and R$_{S5}$, independently is C₁-C₆ alkyl, C₂-C₆ alkenyl, C₂-C₆ alkynyl, C₃-C₈ cycloalkyl, C₆-C₁₀ aryl, 4 to 7-membered heterocycloalkyl, or 5- or 6-membered heteroaryl, and each of R$_{S4}$ and R$_{S5}$ is optionally substituted with one or more -Q₅-T₅, wherein Q₅ is a bond, C(O), C(O)NR$_k$, NR$_k$C(O), S(O)₂, or C₁-C₃ alkyl linker, R$_k$ being H or C₁-C₆ alkyl, and T₅ is H, halo, C₁-C₆ alkyl, hydroxyl, cyano, C₁-C₆ alkoxyl, amino, mono-C₁-C₆ alkylamino, di-C₁-C₆ alkylamino, C₃-C₈ cycloalkyl, C₆-C₁₀ aryl, 4 to 7-membered heterocycloalkyl, 5- or 6-membered heteroaryl, or S(O)$_q$R$_q$ in which q is 0, 1, or 2 and R$_q$ is C₁-C₆ alkyl, C₂-C₆ alkenyl, C₂-C₆ alkynyl, C₃-C₈ cycloalkyl, C₆-C₁₀ aryl, 4 to 7-membered heterocycloalkyl, or 5- or 6-membered heteroaryl, and T₅ is optionally substituted with one or more substituents selected from the group consisting of halo, C₁-C₆ alkyl, hydroxyl, cyano, C₁-C₆ alkoxyl, amino, mono-C₁-C₆ alkylamino, di-C₁-C₆ alkylamino, C₃-C₈ cycloalkyl, C₆-C₁₀ aryl, 4 to 7-membered heterocycloalkyl, and 5- or 6-membered heteroaryl except when T₅ is H, halo, hydroxyl, or cyano; or -Q₅-T₅ is oxo; provided that R₇ is not H; and R₈ is H, halo, hydroxyl, COOH, cyano, R$_{S6}$, OR$_{S6}$, or COOR$_{S6}$, in which R$_{S6}$ is C₁-C₆ alkyl, C₂-C₆ alkenyl, C₂-C₆ alkynyl, amino, mono-C₁-C₆ alkylamino, or di-C₁-C₆ alkylamino, and R$_{S6}$ is optionally substituted with one or more substituents selected from the group consisting of halo, hydroxyl, COOH, C(O)O—C₁-C₆ alkyl, cyano, C₁-C₆ alkoxyl, amino, mono-C₁-C₆ alkylamino, and di-C₁-C₆ alkylamino; or R₇ and R₈, together with the N atom to which they are attached, form a 4 to 11-membered heterocycloalkyl ring which has 0 to 2 additional heteroatoms and is optionally substituted with one or more -Q₆-T₆, wherein Q₆ is a bond, C(O), C(O)NR$_m$, NR$_m$C(O), S(O)₂, or C₁-C₃ alkyl linker, R$_m$ being H or C₁-C₆ alkyl, and T₆ is H, halo, C₁-C₆ alkyl, hydroxyl, cyano, C₁-C₆ alkoxyl, amino, mono-C₁-C₆ alkylamino, di-C₁-C₆ alkylamino, C₃-C₈ cycloalkyl, C₆-C₁₀ aryl, 4 to 7-membered heterocycloalkyl, 5- or 6-membered heteroaryl, or S(O)$_p$R$_p$ in which p is 0, 1, or 2 and R$_p$ is C₁-C₆ alkyl, C₂-C₆ alkenyl, C₂-C₆ alkynyl, C₃-C₈ cycloalkyl, C₆-C₁₀ aryl, 4 to 7-membered heterocycloalkyl, or 5- or 6-membered heteroaryl, and T₆ is optionally substituted with one or more substituents selected from the group consisting of halo, C₁-C₆ alkyl, hydroxyl, cyano, C₁-C₆ alkoxyl, amino, mono-C₁-C₆ alkylamino, di-C₁-C₆ alkylamino, C₃-C₈ cycloalkyl, C₆-C₁₀ aryl, 4 to 7-membered heterocycloalkyl, and 5- or 6-membered heteroaryl except when T₆ is H, halo, hydroxyl, or cyano; or -Q₆-T₆ is oxo.

4. The method of claim 1, wherein the compound of Formula (IIa) is

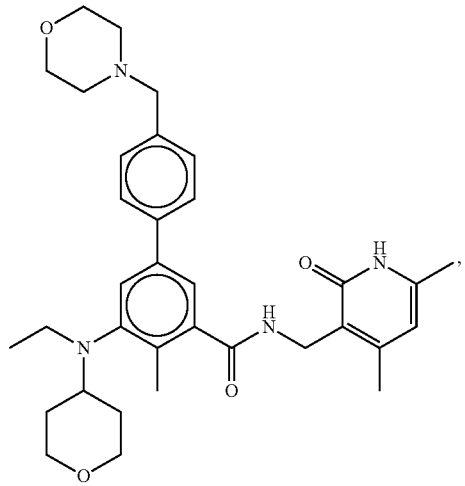

(tazemetostat, EPZ-6438)

or a pharmaceutically-acceptable salt thereof.

5. The method of claim 1, wherein the compound of Formula (IIa) and pembrolizumab are administered simultaneously or in temporal proximity.

6. The method of claim 1, wherein the compound of Formula (IIa) and pembrolizumab are administered sequentially.

7. The method of claim 6, wherein the compound of Formula (IIa) is administered before pembrolizumab.

8. The method of claim 6, wherein pembrolizumab is administered before the compound of Formula (IIa).

9. The method of claim 1, wherein the compound of Formula (IIa) and/or pembrolizumab is administered twice per day.

10. The method of claim 9, wherein the compound of Formula (IIa) is administered orally.

11. The method of claim 1, wherein the compound of Formula (IIa) is administered twice a day at a dosage of 800 mg, and pembrolizumab is administered once every three weeks at a dosage of 1200 mg.

12. The method of claim 11, wherein the compound of Formula (IIa) is administered orally and pembrolizumab is administered parenterally.

13. The method of claim 1, wherein the cancer comprises a stem cell, a progenitor cell, or an immune cell.

14. The method of claim 1, wherein the compound of Formula (IIa) and/or pembrolizumab is between 1 μg/kg and 1000 mg/kg, inclusive of the endpoints.

15. The method of claim 1, wherein the compound of Formula (IIa) and/or pembrolizumab is administered to the subject in a formulation volume between 1 μL and 500 mL, inclusive of the endpoints.

* * * * *